US006468770B1

(12) United States Patent
Keyes et al.

(10) Patent No.: US 6,468,770 B1
(45) Date of Patent: Oct. 22, 2002

(54) NUCLEIC ACIDS AND PROTEINS OF *D. MELANOGASTER* INSULIN-LIKE GENES AND USES THEREOF

(75) Inventors: Linda Nolan Keyes, San Carlos, CA (US); Stephen Kohl Doberstein, San Francisco, CA (US); Andrew Roy Buchman, Berkeley, CA (US); Bindu Priya Reddy, San Francisco, CA (US); David Andrew Ruddy, San Francisco, CA (US)

(73) Assignee: Exelixis Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/201,227

(22) Filed: Nov. 30, 1998

(51) Int. Cl.[7] .................. C12N 15/09; C12N 15/63; C12N 5/00; C12P 21/06; C07H 21/04
(52) U.S. Cl. ................. 435/69.4; 435/320.1; 435/69.1; 435/455; 435/471; 435/325; 536/23.1; 536/23.5; 536/23.51
(58) Field of Search ............... 536/23.1, 23.5, 536/23.51; 435/69.1, 69.4, 455, 320.1, 471, 325

(56) References Cited

U.S. PATENT DOCUMENTS 5,618,717 A * 4/1997 Wei .............................. 463/975
6,135,942 A   10/2000 Leptin ......................... 535/23.5

OTHER PUBLICATIONS

Ngo et. al.; Computational Complexity, Protein Structure Prediction, and the Levinthal Paradox, 1994. In The Protein Folding Problem and Tertiary Structure Prediction, Merz, K et al. (eds.), pp. 491–494.*
Rudinger; Characteristics of the amino acids as components of a peptide hormone sequence, 1976. In Peptide Hormones, Parsons, JA (ed.), pp. 1–7.*
GenBank Accession No. X17024: Mar. 31, 1995.*
GenBank Accession # GI 3626752, Nov. 18, 1998.

Duret et al. 1998. New insulin–like proteins with atypical disulfide bond pattern characterized in Caenorhabditis elegans by comparative sequence analysis and homology modeling. Genome Res. (4):348–53.
Kondo et al. 1996. Multiple gene copies for bombyxin, an insulin–related peptide of the silkmoth *Bombyx mori*: structural signs for gene rearrangement and duplication responsible for generation of multiple molecular forms of bombyxin. J Mol Biol. 259(5):926–37.
Lagueux et al. 1990. cDNAs from neurosecretory cells of brains of *Locusta migratoria* (Insecta, Orthoptera) encoding a novel member of the superfamily of insulins. Eur J Biochem. 187(1):249–54.
Smitt et al. 1988. Growth–controlling molluscan neurons produce the precursor of an insulin–related peptide. Nature;331(6156):535–8.

* cited by examiner

*Primary Examiner*—Dave T. Nguyen
*Assistant Examiner*—Quang Nguyen
(74) *Attorney, Agent, or Firm*—Pennie & Edmonds LLP

(57) ABSTRACT

The present invention relates to *D. melangaster* insulin-like genes and methods for identifying insulin-like genes. The methods provide nucleotide sequences of *D. melangaster* insulin-like genes, amino acid sequences of their encoded proteins, and derivatives (e.g., fragments) and analogs thereof. The invention further relates to fragments (and derivatives and analogs thereof) of insulin-like proteins which comprise one or more domains of an insulin-like protein. Antibodies to an insulin-like protein, and derivatives and analogs thereof, are provided. Methods of production of an insulin-like protein (e.g., by recombinant means), and derivatives and analogs thereof, are provided. Further, methods to identify the biological function of a *D. melangaster* insulin-like gene are provided, including various methods for the functional modification (e.g., overexpression, underexpression, mutation, knock-out) of one or more genes simultaneously. Still further, methods to identify a *D. melangaster* gene which modifies the function of, and/or functions in a signaling pathway with an insulin-like gene are provided. The invention further provides uses of Drosophila insulin-like nucliec acids and proteins, e.g., as media additives, and as pesticides.

12 Claims, 26 Drawing Sheets

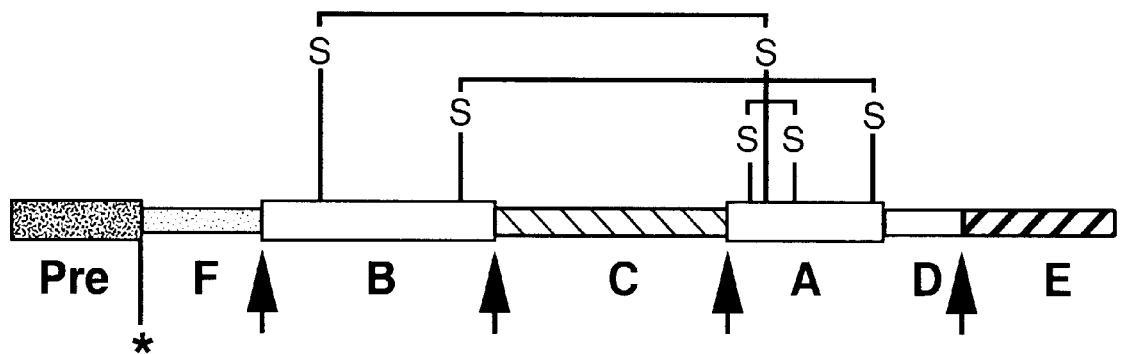
FIG._1

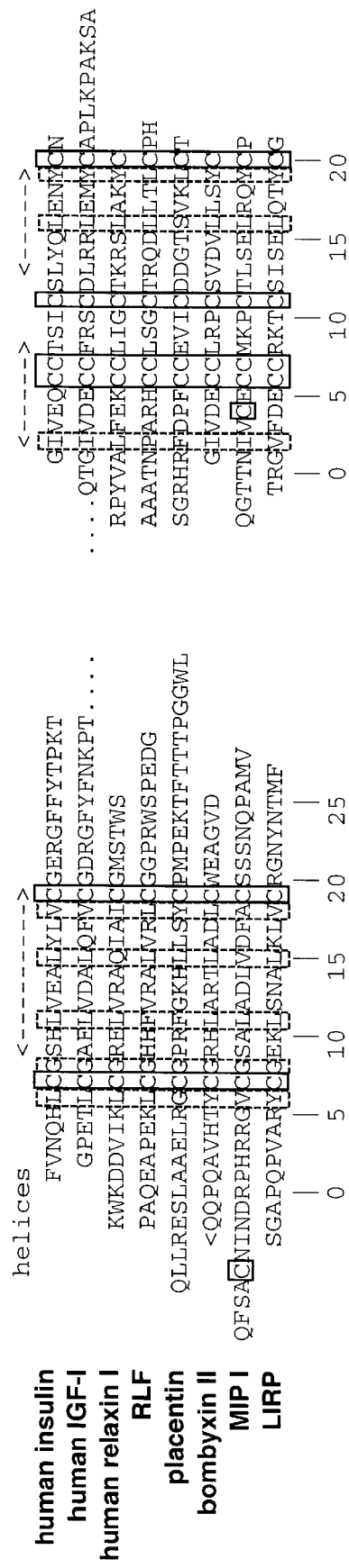
FIG._2

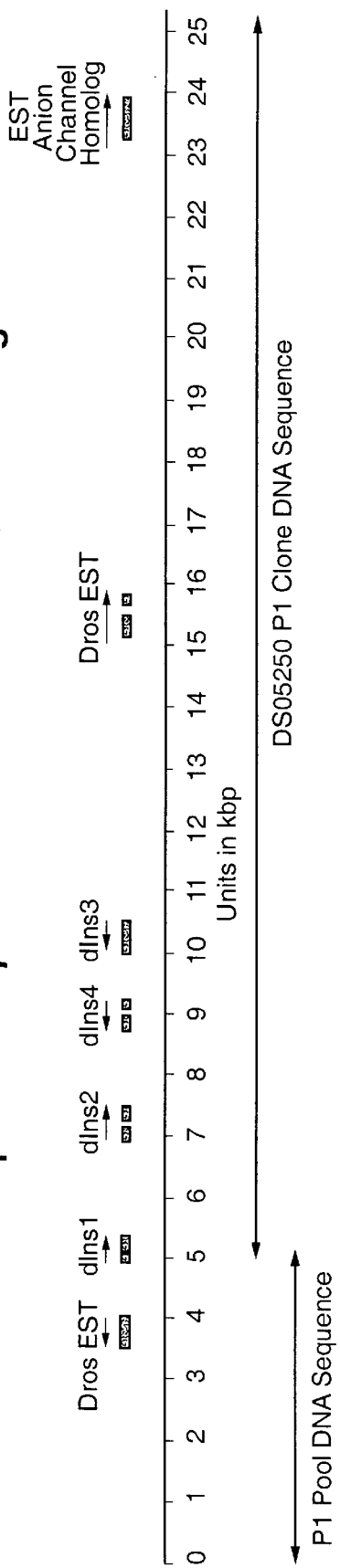
FIG._3

Drosophila Insulin-like Gene Cluster Genomic DNA Sequence

```
         10        20        30        40        50        60
GCTTCTGCTCGGAGAGCGGCTGACCCGAATGGGATAGGGCATCTCCTGTCCACAGGAACG
CGAAGACGAGCCTCTCGCCGACTGGGCTTACCCTATCCCGTAGAGGACAGGTGTCCTTGC 70        80        90       100       110       120
AACTCCCCATTATCGCCCTGCTTGGCCTTCATCGTCTTCACCGCCGATTCAATCAGTCTC
TTGAGGGGTAATAGCGGGACGAACCGGAAGTAGCAGAAGTGGCGGCTAAGTTAGTCAGAG 130       140       150       160       170       180
CAAGGACTATCGCAGTTGTAGTGTCCAAAGGGACCAGGTGGCTCCGATGCCGCACTATTG
GTTCCTGATAGCGTCAACATCACAGGTTTCCCTGGTCCACCGAGGCTACGGCGTGATAAC 190       200       210       220       230       240
GCATTGGAGCCGGAAACCGATCGTGCTAACTCCCAGCAGCTTCTGTATATGTCGCCCTGC
CGTAACCTCGGCCTTTGGCTAGCACGATTGAGGGTCGTCGAAGACATATACAGCGGGACG 250       260       270       280       290       300
GTGGAGTAGAGTGTGTCAAGGTGGAGGTCACTAATGTGCCAGAAGTAGCCTGTCAACAAA
CACCTCATCTCACACAGTTCCACCTCCAGTGATTACACGGTCTTCATCGGACAGTTGTTT 310       320       330       340       350       360
CAAGTAGAATCAAGTAAATGTGTTAGTTAAATACCCATAGATATATGTAAAAGTTGTTGT
GTTCATCTTAGTTCATTTACACAATCAATTTATGGGTATCTATATACATTTTCAACAACA 370       380       390       400       410       420
TTTATTTGCTAAGAAAAGTTTAATCTATATCCCAGTTTTACACACCAGATTTTTATGTCC
AAATAAACGATTCTTTTCAAATTAGATATAGGGTCAAAATGTGTGGTCTAAAAATACAGG 430       440       450       460       470       480
TGAGCAATTTCGTATGTATTTCCCCTTCGTAAAGTAAGGATCGAGATTAGACTTTGACTT
ACTCGTTAAAGCATACATAAAGGGGAAGCATTTCATTCCTAGCTCTAATCTGAAACTGAA 490       500       510       520       530       540
TGGTTAAGTCGGGCAATTCCTGGCCGGGAAAGGCCATTTCCTTTCGCGGGCATTTTCCC
ACCAATTCAGCCCGTTAAGGACCGGCCCTTTCCGGTAAAGGAAAGCGCCCCGTAAAGGG 550       560       570       580       590       600
GCCGGCTGGTCGAGCGACAAAAATAAGAAAAACCTGGTAGTTCAAATGGAAATCTCCTGC
CGGCCGACCAGCTCGCTGTTTTTATTCTTTTTGGACCATCAAGTTTACCTTTAGAGGACG 610       620       630       640       650       660
AGCTGACTGTTTGGTTGGTTGACTGACCTGGCCCGAATTTAACTTTCTACCTGGTCGCAA
TCGACTGACAAACCAACCAACTGACTGGACCGGGCTTAAATTGAAAGATGGACCAGCGTT 670       680       690       700       710       720
TACGTGAAGTCAAAAAGTCAATTAGCGAGTCAACATTTTGAGCGCCGGCCAACTCCAAGG
ATGCACTTCAGTTTTTCAGTTAATCGCTCAGTTGTAAAACTCGCGGCCGGTTGAGGTTCC
                                  ____DINS1 PUT. PROMOTER____>
```

FIG._4A

```
       730       740       750       760       770       780
ATCAGTATCATTTGGCATGCCCAGCGATCGGTTTGCCAAGAGCACGAGAAGTTCGAGATA
TAGTCATAGTAAACCGTACGGGTCGCTAGCCAAACGGTTCTCGTGCTCTTCAAGCTCTAT
            _____>

790       800       810       820       830       840
GGACCCAGAGATACCAGAGATAAAGGAGGCATACCTTTTATGCCCGGTGAGAGCACGGAC
CCTGGGTCTCTATGGTCTCTATTTCCTCCGTATGGAAAATACGGGCCACTCTCGTGCCTG 850       860       870       880       890       900
GGCGGAGTGAAAGATCGAGCAGGATGAGCCTGATTAGACTGGGACTGGCGCTGCTGCTCC
CCGCCTCACTTTCTAGCTCGTCCTACTCGGACTAATCTGACCCTGACCGCGACGACGAGG
                        M   S   L   I   R   L   G   L   A   L   L   L>
                        _____DINS1 CODING REGION (EXON 1)_____>

910       920       930       940       950       960
TGCTGGCCACCGTGTCGCAGTTACTGCAGCCGGTCCAGGGACGCCGAAAGATGTGCGGCG
ACGACCGGTGGCACAGCGTCAATGACGTCGGCCAGGTCCCTGCGGCTTTCTACACGCCGC
  L   L   A   T   V   S   Q   L   L   Q   P   V   Q   G   R   R   K   M   C   G>
  _____DINS1 CODING REGION (EXON 1)_____>

>End_of_DS05250_sequence
              |
       970       980       990      1000      1010      1020
AGGCTCTGATCCAGGCACTGGATGTGATTTGTGTTAATGGATTTACACGCCGTGTCAGGC
TCCGAGACTAGGTCCGTGACCTACACTAAACACAATTACCTAAATGTGCGGCACAGTCCG
  E   A   L   I   Q   A   L   D   V   I   C   V   N   G   F   T   R   R   V   R>
  _____DINS1 CODING REGION (EXON 1)_____>

1030      1040      1050      1060      1070      1080
GGAGCAGTGGTAAGTTTGGGTACTATGCATATTCGATTGGCTTCCATACATCTAACTTCT
CCTCGTCACCATTCAAACCCATGATACGTATAAGCTAACCGAAGGTATGTAGATTGAAGA
  R   S   S   A>
  _____>

1090      1100      1110      1120      1130      1140
TTTCGACAAGCGTCTAAGGATGCTAGAGTGCGAGACCTTATCCGTAAGCTACAGCAGCCG
AAAGCTGTTCGCAGATTCCTACGATCTCACGCTCTGGAATAGGCATTCGATGTCGTCGGC
          S   K   D   A   R   V   R   D   L   I   R   K   L   Q   Q   P>
          _____DINS1 CODING REGION (EXON-2)_____>

1150      1160      1170      1180      1190      1200
GATGAGGACATTGAACAGGAAACGGAAACGGGAAGGTTAAAGCAGAAGCATACGGATGCG
CTACTCCTGTAACTTGTCCTTTGCCTTTGCCCTTCCAATTTCGTCTTCGTATGCCTACGC
  D   E   D   I   E   Q   E   T   E   T   G   R   L   K   Q   K   H   T   D   A>
  _____DINS1 CODING REGION (EXON-2)_____>

1210      1220      1230      1240      1250      1260
GATACGGAGAAGGGTGTGCCACCGGCCGTCGGAAGTGGACGAAAGTTGCGACGCCATCGG
CTATGCCTCTTCCCACACGGTGGCCGGCAGCCTTCACCTGCTTTCAACGCTGCGGTAGCC
  D   T   E   K   G   V   P   P   A   V   G   S   G   R   K   L   R   R   H   R>
  _____DINS1 CODING REGION (EXON-2)_____>
```

FIG._4B

```
         1270       1280       1290       1300       1310       1320
    CGACGCATCGCCCACGAGTGTTGCAAGGAGGGCTGCACCTACGACGATATACTGGACTAC
    GCTGCGTAGCGGGTGCTCACAACGTTCCTCCCGACGTGGATGCTGCTATATGACCTGATG
      R  R  I  A  H  E  C  C  K  E  G  C  T  Y  D  D  I  L  D  Y>
    _____DINS1 CODING REGION (EXON-2)_____>

>dIns1_poly(A)_signal
                                         |
        1330       1340       1350       |   1360       1370       1380
    TGCGCCTGATGACCAGGATGGCAAAACAAAACAAATAAAAACCAGAAACCAGATCCCAAA
    ACGCGGACTACTGGTCCTACCGTTTTGTTTTGTTTATTTTTGGTCTTTGGTCTAGGGTTT
      C  A  *>
    _____>

1390       1400       1410       1420       1430       1440
    AACCAAGTACCAGATGAACACGACATGGCTGAGATTTTGTGTGGCGGCACGGGGAAAACA
    TTGGTTCATGGTCTACTTGTGCTGTACCGACTCTAAAACACACCGCCGTGCCCCTTTTGT 1450       1460       1470       1480       1490       1500
    CCCGACGACCGGCAGGCTATTTGCAATTCATTTTCCTACTACACTTAACCCCTAACTATA
    GGGCTGCTGGCCGTCCGATAAACGTTAAGTAAAAGGATGATGTGAATTGGGGATTGATAT 1510       1520       1530       1540       1550       1560
    AACGTAATCGTATTTCCAAATATTTCATTGTAAAATTTCTAGTGGAGGCAAATAAAGTTA
    TTGCATTAGCATAAAGGTTTATAAAGTAACATTTTAAAGATCACCTCCGTTTATTTCAAT 1570       1580       1590       1600       1610       1620
    CTCTCCAAGCAGCAGCAGAAACAAAAGAAGAGTCCATTGCTTTTTTCTACATTCTACGCC
    GAGAGGTTCGTCGTCGTCTTTGTTTTCTTCTCAGGTAACGAAAAAGATGTAAGATGCGG 1630       1640       1650       1660       1670       1680
    CTGCAGCATTCCAGCTGTGAGGCATGGGGAATCCCCTTGTTATTCAAACCACCCGAAGCC
    GACGTCGTAAGGTCGACACTCCGTACCCCTTAGGGGAACAATAAGTTTGGTGGGCTTCGG 1690       1700       1710       1720       1730       1740
    ACCCAAACCATCGAGCCACCCACAAGCAGCTGCCATTCAGCACCTCGAGTGCGGTGCCCT
    TGGGTTTGGTAGCTCGGTGGGTGTTCGTCGACGGTAAGTCGTGGAGCTCACGCCACGGGA 1750       1760       1770       1780       1790       1800
    TGTTTTCCGAGAACAATAATGAAAATATGAATTTTTAATTAGATGACGTTCTGATTTTA
    ACAAAAGGCTCTTGTTATTACTTTTTATACTTAAAAATTAATCTACTGCAAGACTAAAAT 1810       1820       1830       1840       1850       1860
    ATAAGCAAAACAAAAGGTGGAGACAAAACGAACTCGGTAATACACTCAGATTCGAATTTA
    TATTCGTTTTGTTTTCCACCTCTGTTTTGCTTGAGCCATTATGTGAGTCTAAGCTTAAAT 1870       1880       1890       1900       1910       1920
    CAGCTTCCTTTTTATCCATAATTTTTGTTATTATCGAAGGAGCGATATCAAAACTAGAAA
    GTCGAAGGAAAAATAGGTATTAAAAACAATAATAGCTTCCTCGCTATAGTTTTGATCTTT 1930       1940       1950       1960       1970       1980
    ACAACTTCCAATCAGTAGCGGGATTTTCCGAAGATAACACTCTATTCAACCGAAGGGTTT
    TGTTGAAGGTTAGTCATCGCCCTAAAAGGCTTCTATTGTGAGATAAGTTGGCTTCCCAAA
```

FIG._4C

```
      1990       2000       2010       2020       2030       2040
TGAAATGATAATAATTCCGTTCTTACAGGTAAAAATCTATACTAATACCTGTTTTTTTGC
ACTTTACTATTATTAAGGCAAGAATGTCCATTTTTAGATATGATTATGGACAAAAAAACG 2050       2060       2070       2080       2090       2100
GGACGGAAAAAAGGCTCAGTTGGCTTATCATTGGCAAAAGGGACTTGGGGAAACCATAAA
CCTGCCTTTTTTCCGAGTCAACCGAATAGTAACCGTTTTCCCTGAACCCCTTTGGTATTT 2110       2120       2130       2140       2150       2160
GTATCGAAGGTACTGAGCCAAGATAATGAGATAACAGAAGGCGACTTTATTGTTTTCCAC
CATAGCTTCCATGACTCGGTTCTATTACTCTATTGTCTTCCGCTGAAATAACAAAAGGTG 2170       2180       2190       2200       2210       2220
TCAAAAGCAATTGAATAAGTTGGCACTCGTTTTTAATTGAATGGGAATGAAATAAGCTCT
AGTTTTCGTTAACTTATTCAACCGTGAGCAAAAATTAACTTACCCTTACTTTATTCGAGA 2230       2240       2250       2260       2270       2280
AAAAGTGTTGTTAAAACGTAATGGCTTTTGTGTTAATTTAAAGAATTTAAGTAGTTTTGA
TTTTCACAACAATTTTGCATTACCGAAAACACAATTAAATTTCTTAAATTCATCAAAACT 2290       2300       2310       2320       2330       2340
AAGTATCATTATTCTTTAGGTAATTTTTATTACATTCCAAATTTAATAAATGACTAATTC
TTCATAGTAATAAGAAATCCATTAAAAATAATGTAAGGTTTAAATTATTTACTGATTAAG 2350       2360       2370       2380       2390       2400
GAAAAGTGTTTATTTAATCAATGAATATATTTCAAGTAAGTTTACTTTTAGTAGCTTGC
CTTTTTCACAAATAAATTAGTTACTTATATAAAGTTCATTCAAATGAAAATCATCGAACG 2410       2420       2430       2440       2450       2460
CAAATGTGAGTTTAAATATGTATGCATAGAACTATATAGTTAAACTGCTAAACTTTACAG
GTTTACACTCAAATTTATACATACGTATCTTGATATATCAATTTGACGATTTGAAATGTC 2470       2480       2490       2500       2510       2520
TTAAACTTTCTGAACCCACCAAAATGGATGAACATCCTCGTCTGCCGAAGGGAACTCGAT
AATTTGAAAGACTTGGGTGGTTTTACCTACTTGTAGGAGCAGACGGCTTCCCTTGAGCTA 2530       2540       2550       2560       2570       2580
GCACGTCATTTTGTTTTTCAACAATCCAGATCCGTGCGCTACTCCTTGGGCGAGAAAGTA
CGTGCAGTAAAACAAAAGTTGTTAGGTCTAGGCACGCGATGAGGAACCCGCTCTTTCAT 2590       2600       2610       2620       2630       2640
AACAAACGCCAGCTGATATGCGTCAGACCCCCCGGGCTCATCATCATCTCACCATTTCAG
TTGTTTGCGGTCGACTATACGCAGTCTGGGGGGCCCGAGTAGTAGTAGAGTGGTAAAGTC 2650       2660       2670       2680       2690       2700
ACATCCCATGCCAGCCCGAATCCTCACGAGAAACTAGACCAGACCAGGGCGAACTACATA
TGTAGGGTACGGTCGGGCTTAGGAGTGCTCTTTGATCTGGTCTGGTCCCGCTTGATGTAT 2710       2720       2730       2740       2750       2760
TGTGGATGATGCTAACTGACACTACGGCTGACTCATGCTGACAGTGCTCAGACGCTGGAT
ACACCTACTACGATTGACTGTGATGCCGACTGAGTACGACTGTCACGAGTCTGCGACCTA
```

FIG._4D

```
            2770       2780       2790       2800       2810       2820
     ACAGCCCGCAGACATCCAACTCGTATCCTATCCGATTCTGCCCCATATATATAACCCTCA
     TGTCGGGCGTCTGTAGGTTGAGCATAGGATAGGCTAAGACGGGGTATATATATTGGGAGT
                                                   ___DINS2 PUT. ____>

2830       2840       2850       2860       2870       2880
     GTCGATGGCTGGGAGGCAAACAGTTGAGGCCGTGCCACTTGGCAGACACATACTACACAC
     CAGCTACCGACCCTCCGTTTGTCAACTCCGGCACGGTGAACCGTCTGTGTATGATGTGTG
     ___DINS2 PUT. PROM____>

2890       2900       2910       2920       2930       2940
     TCCCCGGGGGATTCACGCATCCATACTTAAACACCACTTCATCACTCATGGGCATCGAGA
     AGGGGCCCCCTAAGTGCGTAGGTATGAATTTGTGGTGAAGTAGTGAGTACCCGTAGCTCT
                                                                 _>

2950       2960       2970       2980       2990       3000
     TGAGGTGTCAGGACAGGAGGATCCTGCTACCTAGCCTACTCCTACTAATCCTTATGATCG
     ACTCCACAGTCCTGTCCTCCTAGGACGATGGATCGGATGAGGATGATTAGGAATACTAGC
      M  R  C  Q  D  R  R  I  L  L  P  S  L  L  L  I  L  M  I>
     _____DINS2 CODING REGION (EXON-1)_____>

3010       3020       3030       3040       3050       3060
     GCGGTGTCCAGGCCACCATGAAGTTGTGCGGCCGCAAACTGCCCGAAACTCTCTCCAAGC
     CGCCACAGGTCCGGTGGTACTTCAACACGCCGGCGTTTGACGGGCTTTGAGAGAGGTTCG
      G  G  V  Q  A  T  M  K  L  C  G  R  K  L  P  E  T  L  S  K>
     _____DINS2 CODING REGION (EXON-1)_____>

3070       3080       3090       3100       3110       3120
     TCTGTGTGTATGGCTTCAACGCAATGACCAAGAGAACTTTGGGTAGGTGGGATTTTTCTT
     AGACACACATACCGAAGTTGCGTTACTGGTTCTCTTGAAACCCATCCACCCTAAAAAGAA
      L  C  V  Y  G  F  N  A  M  T  K  R  T  L  D>
     _____DINS2 CODING REGION (EXON-1)_____>

3130       3140       3150       3160       3170       3180
     GATATAAGGAATACTAAAGTGCCATATCTCTTTACTTTCACCTAACACCTGTAGACCCCG
     CTATATTCCTTATGATTTCACGGTATAGAGAAATGAAAGTGGATTGTGGACATCTGGGGC
                                                                 P>
                                                          _____>

3190       3200       3210       3220       3230       3240
     TGAACTTCAATCAGATCGATGGCTTCGAAGACCGTTCCCTGCTGGAAAGACTGTTGAGTG
     ACTTGAAGTTAGTCTAGCTACCGAAGCTTCTGGCAAGGGACGACCTTTCTGACAACTCAC
      V  N  F  N  Q  I  D  G  F  E  D  R  S  L  L  E  R  L  L  S>
     _____DINS2 CODING REGION (EXON-2)_____>

3250       3260       3270       3280       3290       3300
     ATAGTTCGGTTCAGATGCTCAAGACTCGACGTCTTCGGGATGGAGTCTTCGACGAGTGTT
     TATCAAGCCAAGTCTACGAGTTCTGAGCTGCAGAAGCCCTACCTCAGAAGCTGCTCACAA
      D  S  S  V  Q  M  L  K  T  R  R  L  R  D  G  V  F  D  E  C>
     _____DINS2 CODING REGION (EXON-2)_____>
```

FIG._4E

```
              3310       3320       3330       3340       3350       3360
         GCCTGAAGTCGTGCACCATGGATGAGGTGCTGAGATATTGTGCTGCCAAGCCGAGAACGT
         CGGACTTCAGCACGTGGTACCTACTCCACGACTCTATAACACGACGGTTCGGCTCTTGCA
          C   L   K   S   C   T   M   D   E   V   L   R   Y   C   A   A   K   P   R   T>
         _____DINS2 CODING REGION (EXON-2)_____>

3370       3380       3390       3400       3410       3420
         AAACCTCGTAAACCTATTAACCCAATGACGACAACTGCGATGATTGAAATGGAATGAAAG
         TTTGGAGCATTTGGATAATTGGGTTACTGCTGTTGACGCTACTAACTTTACCTTACTTTC
          *  >
         ___>

3430       3440       3450       3460       3470       3480
         GACCCGATTGGGGAAAGCACTCACGTAATCATAGTTGTTAAGTCGTTATCGAAGCCTACT
         CTGGGCTAACCCCTTTCGTGAGTGCATTAGTATCAACAATTCAGCAATAGCTTCGGATGA 3490       3500       3510       3520       3530       3540
         CAATTCCAACTTTGGATTTATGATATATATGCACATGTAAGAGGGATGTATGCGCATAAT
         GTTAAGGTTGAAACCTAAATACTATATATACGTGTACATTCTCCCTACATACGCGTATTA 3550       3560       3570       3580       3590       3600
         TTATGATCTGAAATCAGAGACAGGCACGCGAAATGAATCGGAACACGGGATGTTATGCAT
         AATACTAGACTTTAGTCTCTGTCCGTGCGCTTTACTTAGCCTTGTGCCCTACAATACGTA

>dIns2_put._poly(A)_signal
                                                                             |
              3610       3620       3630       3640       3650       3660
         GGTAGATATGTATGATTGTGCGGGGCCAGAATACATCGCCTGGGTATAAATTATTAAATA
         CCATCTATACATACTAACACGCCCCGGTCTTATGTAGCGGACCCATATTTAATAATTTAT 3670       3680       3690       3700       3710       3720
         AATTATGTATTCAAACTGCTGCAGATTGGCCAACTTGATTGGTAATGAAACGGGTATTAC
         TTAATACATAAGTTTGACGACGTCTAACCGGTTGAACTAACCATTACTTTGCCCATAATG <dIns4_put._poly(A)_signal
                                                                 |
              3730       3740       3750       3760|      3770       3780
         ATTGATTTTTCATTGTCGTTCATTGCAGTTAATTATTTATTGAACAGCGGCCGGATTTCT
         TAACTAAAAAGTAACAGCAAGTAACGTCAATTAATAAATAACTTGTCGCCGGCCTAAAGA 3790       3800       3810       3820       3830       3840
         GTTTGCAACTATGTTGAAAAGGAAGCTGTGATTTTTTAACAAACTCTGTTCATTGTAAAG
         CAAACGTTGATACAACTTTTCCTTCGACACTAAAAAATTGTTTGAGACAAGTAACATTTC 3850       3860       3870       3880       3890       3900
         TTTAAAATCATTCCAATTTAATGCCCTCAAAACCTACGCTGAAATGGTCAGTTTTAAAAC
         AAATTTTAGTAAGGTTAAATTACGGGAGTTTTGGATGCGACTTTACCAGTCAAAATTTTG 3910       3920       3930       3940       3950       3960
         GATATTTATTAATATTTTAGTTAATTTACTAAGATTATCCGTTTTGCACTTTTAATGCCT
         CTATAAATAATTATAAAATCAATTAAATGATTCTAATAGGCAAAACGTGAAAATTACGGA
```

FIG._4F

```
              3970        3980        3990        4000        4010        4020
    TGCATTTGGTAATGCGTGATTGTTATTTAAGGTCTGCATGAATTTAGTTGATTCCGTTTA
    ACGTAAACCATTACGCACTAACAATAAATTCCAGACGTACTTAAATCAACTAAGGCAAAT 4030        4040        4050        4060        4070        4080
    TTTTAGCTTTCAAAATGTAATAATCTTCTAATTTACAACTACACAGAACGATTAAATTAT
    AAAATCGAAAGTTTTACATTATTAGAAGATTAAATGTTGATGTGTCTTGCTAATTTAATA 4090        4100        4110        4120        4130        4140
    GAGTATTGCTATAAAATCGGCCAACCGCGACTAGAAATACTCGACTTTTAAGGTCAACAT
    CTCATAACGATATTTTAGCCGGTTGGCGCTGATCTTTATGAGCTGAAAATTCCAGTTGTA 4150        4160        4170        4180        4190        4200
    AAAGTAAGTCAATGTTTTGATTATAAGATTTGATCAATTACTTCTTTACGGATGATATA
    TTTTCATTCAGTTACAAAACTAATATTCTAAACTAGTTAATGAAGAAATGCCTACTATAT 4210        4220        4230        4240        4250        4260
    ATCATCGATAAACGAAGTACGAAAAAAGCTATGAACTAAAATTTGGAAATTTCCCACATG
    TAGTAGCTATTTGCTTCATGCTTTTTCGATACTTGATTTTAAACCTTTAAAGGGTGTAC 4270        4280        4290        4300        4310        4320
    CGACTAACTTTTGAATTGCAATTGGATTGCCTACTGTATTAAGACAGAAACAAGTTTTGG
    GCTGATTGAAAACTTAACGTTAACCTAACGGATGACATAATTCTGTCTTTGTTCAAAACC 4330        4340        4350        4360        4370        4380
    AAATGAATGAATGGTTTAAATTGTTTCAAGTTTTTTTAAGATTTTTTTTGTTTTCAATAA
    TTTACTTACTTACCAAATTTAACAAAGTTCAAAAAAATTCTAAAAAAAACAAAAGTTATT 4390        4400        4410        4420        4430        4440
    ATTTAGTTTTAATAGAAAAAAAGATATATTCATTTTAGATTTCTGAATACTTGTGTTATA
    TAAATCAAAATTATCTTTTTTTCTATATAAGTAAAATCTAAAGACTTATGAACACAATAT 4450        4460        4470        4480        4490        4500
    TCGCTTTTTTATTCAAGTGTAATAATCAACATATATATCATATAATGATAATAATAAATGT
    AGCGAAAAATAAGTTCACATTATTAGTTGTATATATAGTATATTACTATTATTATTTACA 4510        4520        4530        4540        4550        4560
    AACGTCCCAAATTAATAATAATATAAAGTAGCATTTGCGATTGTTTGCCAAAGCTTAAAG
    TTGCAGGGTTTAATTATTATTATATTTCATCGTAAACGCTAACAAACGGTTTCGAATTTC 4570        4580        4590        4600        4610        4620
    CAGAATATATATTTAATCCATTTCGATCATTCGTAAAGAGTAACATGCAACAAGCTGTAA
    GTCTTATATATAAATTAGGTAAAGCTAGTAAGCATTTCTCATTGTACGTTGTTCGACATT 4630        4640        4650        4660        4670        4680
    AAAACATCGATTGTAGTATATATGCACATGGTTGGTTTGGAACCAGATCCAGAGATAATC
    TTTTGTAGCTAACATCATATATACGTGTACCAACCAAACCTTGGTCTAGGTCTCTATTAG 4690        4700        4710        4720        4730        4740
    GCGTCGACCAGGTCAGTTGGGGTCAATGATTTTCGCATTAGGAGGCCTAATTTCTGACCA
    CGCAGCTGGTCCAGTCAACCCCAGTTACTAAAAGCGTAATCCTCCGGATTAAAGACTGGT
                                                          <*  N   R   V   V
                                                          <_____
```

FIG._4G

```
       4750        4760        4770        4780        4790        4800
CGGAGCAGTACTCCCGCAGAGCCTTCATATCACAGGACTTTTTGCAGCACCTCTCCACGA
GCCTCGTCATGAGGGCGTCTCGGAAGTATAGTGTCCTGAAAAACGTCGTGGAGAGGTGCT
   <S   C   Y   E   R   L   A   K   M   D   C   S   K   K   C   C   R   E   V   I
   <_____DINS4 CODING REGION (EXON-2)_____

4810        4820        4830        4840        4850        4860
TTCCTTGCCGTTGGCGAGTTCGCCTCCGGACTTCAGCCAGGGAATTGAGTACACCCCCAA
AAGGAACGGCAACCGCTCAAGCGGAGGCCTGAAGTCGGTCCCTTAACTCATGTGGGGGTT
   <G   Q   R   Q   R   T   R   R   R   V   E   A   L   S   N   L   V   G   G   L
   <_____DINS4 CODING REGION (EXON-2)_____

4870        4880        4890        4900        4910        4920
GATAGCTCCCAGGAAAGAGGGCACTTCGCAGCGGTTCCGATATCGAGTTATCCTCCTCCT
CTATCGAGGGTCCTTTCTCCCGTGAAGCGTCGCCAAGGCTATAGCTCAATAGGAGGAGGA
   <Y   S   G   P   F   L   A   S   R   L   P   E   S   I   S   N   D   E   E   E
   <_____DINS4 CODING REGION (EXON-2)_____

4930        4940        4950        4960        4970        4980
CGAACTCCTGGACAAACTGCAGGGGATTGAGGGCGTCCAGATCGCTGTCGGCACCGGCTA
GCTTGAGGACCTGTTTGACGTCCCCTAACTCCCGCAGGTCTAGCGACAGCCGTGGCCGAT
   <F   E   Q   V   F   Q   L   P   N   L   A   D   L   D   S   D   A   G   P
   <_____DINS4 CODING REGION (EXON-2)_____

4990        5000        5010        5020        5030        5040
ATAAAAATCGTGGATACAATGTAGATCTAGCAAAGCCAGCTTGAGGATCTGCATCCTTGT
TATTTTTAGCACCTATGTTACATCTAGATCGTTTCGGTCGAACTCCTAGACGTAGGAACA 5050        5060        5070        5080        5090        5100
AAGAACTTACGCATGGCGCGCTTGTGTGGAATCACGGGATTATACTCCTCGCACACCATA
TTCTTGAATGCGTACCGCGCGAACACACCTTAGTGCCCTAATATGAGGAGCGTGTGGTAT
          <M   A   R   K   H   P   I   V   P   N   Y   E   E   C   V   M
          <_____DINS4 CODING REGION (EXON 1)_____

5110        5120        5130        5140        5150        5160
CTCAGCACCTCGTTGAGCTTTTCACTGCAGAGCGTTCCTTGGGCCAACTTCACTGTGGAG
GAGTCGTGGAGCAACTCGAAAAGTGACGTCTCGCAAGGAACCCGGTTGAAGTGACACCTC
<S   L   V   E   N   L   K   E   S   C   L   T   G   Q   A   L   K   V   T   S
<_____DINS4 CODING REGION (EXON 1)_____

5170        5180        5190        5200        5210        5220
CTGGCCAGCAAAATCACGGCCACCATCGAGATGAAGGACAAAGGCTTGCTCATGGTTATG
GACCGGTCGTTTTAGTGCCGGTGGTAGCTCTACTTCCTGTTTCCGAACGAGTACCAATAC
<S   A   L   L   I   V   A   V   M   S   I   F   S   L   P   K   S   M
<_____DINS4 CODING REGION (EXON 1)_____

5230        5240        5250        5260        5270        5280
GGTTTACTGCTTAGGTTGCTTTACGATCAAATGGATTAAGTTGGGTCGAGCCGGGTCGAA
CCAAATGACGAATCCAACGAAATGCTAGTTTACCTAATTCAACCCAGCTCGGCCCAGCTT
```

FIG._4H

```
     5290       5300       5310       5320       5330       5340
AGCTAACTGATGATGTTTGGCCCAAAGTAACTGGCTTATATACTGCCTCGTAAGAAACTT
TCGATTGACTACTACAAACCGGGTTTCATTGACCGAATATATGACGGAGCATTCTTTGAA
      <_____DINS4 PUT. PROMOTER_____

5350       5360       5370       5380       5390       5400
AAACTGGGTCTGGGTCGGGGTCGGTCTCTCGGGGTCGGGGTCTGGATCCACACACATGTT
TTTGACCCAGACCCAGCCCCAGCCAGAGAGCCCCAGCCCCAGACCTAGGTGTGTGTACAA 5410       5420       5430       5440       5450       5460
ATCCTCAAAAGTCAGGTTGTCAAATTGTGTTAGGATGCGATGAGTGCATTCCGGAGTTGG
TAGGAGTTTTCAGTCCAACAGTTTAACACAATCCTACGCTACTCACGTAAGGCCTCAACC 5470       5480       5490       5500       5510       5520
CTCTTCTCTCTAACGCCTGGCTAAACTCATTCAATGTCAAAGCTGACTTATGCAAATGGC
GAGAAGAGAGATTGCGGACCGATTTGAGTAAGTTACAGTTTCGACTGAATACGTTTACCG 5530       5540       5550       5560       5570       5580
TATTGGAAAATTGTGGGTGGTTTTTGGGTGGCTGTGTTTGGGAGAAGAAGGGCTTTGTGG
ATAACCTTTTAACACCCACCAAAAACCCACCGACACAAACCCTCTTCTTCCCGAAACACC 5590       5600       5610       5620       5630       5640
GCGTTTGCTGTCAGCCAATTAAACAATTTATGTATAAACAGCCAGGCCGTACTAAGCCC
CGCAAAACGACAGTCGGTTAATTTGTTAAATACATATTTGTCGGTCCGGCATGATTCGGG 5650       5660       5670       5680       5690       5700
TGCATTTATGAATACCAAATAAGTCCTTGGTCTTAAAGTTACCTCGCCTTTACAGCCCGT
ACGTAAATACTTATGGTTTATTCAGGAACCAGAATTTCAATGGAGCGGAAATGTCGGGCA 5710       5720       5730       5740       5750       5760
TTGCCTCTACCATTTCTACCCTATACTTACCAATCCGCGCCTGGGCGCCCGGCAGGCCGG
AACGGAGATGGTAAAGATGGGATATGAATGGTTAGGCGCGGACCCGCGGGCCGTCCGGCC 5770       5780       5790       5800       5810       5820
AGTAGGCCAACAAGAACCCGAGCCAGCTGATTGGAGCCAGCAGCATCCTGGCAACGAATT
TCATCCGGTTGTTCTTGGGCTCGGTCGACTAACCTCGGTCGTCGTAGGACCGTTGCTTAA 5830       5840       5850       5860       5870       5880
ACGCCTCCTTGGTACTTTTCCTTTGACTGTCTTGTCTTTGCCGCTCACACAAATTCTTCT
TGCGGAGGAACCATGAAAAGGAAACTGACAGAACAGAAACGGCGAGTGTGTTTAAGAAGA

<dIns3_put._poly(A)_signal
                              |
     5890       5900       |  5910       5920       5930       5940
TTTTGCACTGTCTACTTTTATTCATTAGTCAAAGTTGGTGCTGCATAAATAAGTGATTAC
AAAACGTGACAGATGAAAATAAGTAATCAGTTTCAACCACGACGTATTTATTCACTAATG 5950       5960       5970       5980       5990       6000
GAATTGGATTACGAATGCTGTTAGGAGAACGGGTGTACATATAGTATGTATGTGGGAATG
CTTAACCTAATGCTTACGACAATCCTCTTGCCCACATGTATATCATACATACACCCTTAC
```

FIG._4I

```
       6010        6020        6030        6040        6050        6060
CCATGTTCAAGTGTTCGTATGTATGTATGTATGTGTATGCATGCTGGGTAATGAATGTGT
GGTACAAGTTCACAAGCATACATACATACATACACATACGTACGACCCATTACTTACACA 6070        6080        6090        6100        6110        6120
GTGTGTTGGCCAAGTGTCCTATTTCGGTAGACAGTAGATGGCTAACTCCAAGTAGCTGCA
CACACAACCGGTTCACAGGATAAAGCCATCTGTCATCTACCGATTGAGGTTCATCGACGT
         <*  K  P  L  C  Y  I  A  L  E  L  Y  S  C
         <_____DINS3 CODING REGION_____

6130        6140        6150        6160        6170        6180
GGTCTTGACGCAGCACTCGTCGTAGACGCCACCGGTCAGGTGTCTCCTGTGGCGACGCAT
CCAGAACTGCGTCGTGAGCAGCATCTGCGGTGGCCAGTCCACAGAGGACACCGCTGCGTA
<T  K  V  C  C  E  D  Y  V  G  G  T  L  H  R  R  H  R  R  M
<_____DINS3 CODING REGION_____

6190        6200        6210        6220        6230        6240
CTTGATCAGGACCTCGGATCCGTACAGATTGGTTAGCAGTGGACTAAAAGAGTATCCTGC
GAACTAGTCCTGGAGCCTAGGCATGTCTAACCAATCGTCACCTGATTTTCTCATAGGACG
<K  I  L  V  E  S  G  Y  L  N  T  L  L  P  S  F  S  Y  G  A
<_____DINS3 CODING REGION_____

6250        6260        6270        6280        6290        6300
CCCGTCCAGTGTCTGCCACATGCTGCTATCATCCTGCACCTCCTGCTCCGTGTCCTCGTC
GGGCAGGTCACAGACGGTGTACGACGATAGTAGGACGTGGAGGACGAGGCACAGGAGCAG
<G  D  L  T  Q  W  M  S  S  D  D  Q  V  E  Q  E  T  D  E  D
<_____DINS3 CODING REGION_____

6310        6320        6330        6340        6350        6360
GTCGTCGCTGTTGCCCAGCAAGCTTTCACGTTTCCTTGGCAGCGTATTAAAGCCATGGGG
CAGCAGCGACAACGGGTCGTTCGAAAGTGCAAAGGAACCGTCGCATAATTTCGGTACCCC
<D  D  S  N  G  L  L  S  E  R  K  R  P  L  T  N  F  G  H  P
<_____DINS3 CODING REGION_____

6370        6380        6390        6400        6410        6420
ACACACCACATCCATGGCATCGGACAGTGCGGGGCCGCAGAGTTTGTGGTTTCCGGGGGG
TGTGTGGTGTAGGTACCGTAGCCTGTCACGCCCCGGCGTCTCAAACACCAAAGGCCCCCC
<C  V  V  D  M  A  D  S  L  A  P  G  C  L  K  H  N  G  P  P
<_____DINS3 CODING REGION_____

6430        6440        6450        6460        6470        6480
CAGCAACTGGTGACCACTGCCAGTCGGCGTGACCATTGCCATTGCAGCGGTGAGCATGGC
GTCGTTGACCACTGGTGACGGTCAGCCGCACTGGTAACGGTAACGTCGCCACTCGTACCG
<L  L  Q  H  G  S  G  T  P  T  V  M  A  M  A  A  T  L  M  A
<_____DINS3 CODING REGION_____

6490        6500        6510        6520        6530        6540
TGCGATGAGCAGCGACTGGAGCCGAAGGCCATGTACTGCTGCACCGTTGTGCTGGCTAAA
ACGCTACTCGTCGCTGACCTCGGCTTCCGGTACATGACGACGTGGCAACACGACCGATTT
<A  I  L  L  S  Q  L  R  L  G  H  V  A  A  G  N  H  Q  S  F
<_____DINS3 CODING REGION_____
```

FIG._4J

```
       6550       6560       6570       6580       6590       6600
CATCTTGGATATGCAGTGAATGCTCTGGGCTGCAACTGGTATTTATACCACTAAATCGGA
GTAGAACCTATACGTCACTTACGAGACCCGACGTTGACCATAAATATGGTGATTTAGCCT
                                                           <M
<____

<_____

6610       6620       6630       6640       6650       6660
AGCGCTAGCTAATGCAGTTCAATGGCCTCTTCTGCAGTCTAGCATTGCAGTGGCATAGCA
TCGCGATCGATTACGTCAAGTTACCGGAGAAGACGTCAGATCGTAACGTCACCGTATCGT
<_____DINS3 PUT. PROMOTER_____

6670       6680       6690       6700       6710       6720
AGCCCCACGGGCGTACAAACTGCAAATCCTTTGATCACCCATGTTTCAGGTACCGTTTTT
TCGGGGTGCCCGCATGTTTGACGTTTAGGAAACTAGTGGGTACAAAGTCCATGGCAAAAA 6730       6740       6750       6760       6770       6780
CCCCTAAAAATGCAAACTCTATTTCTAGCTCTACTCCCCAATTTGGATGGAAAAGCGATG
GGGGATTTTTACGTTTGAGATAAAGATCGAGATGAGGGGTTAAACCTACCTTTTCGCTAC 6790       6800       6810       6820       6830       6840
CACTGTTGTTTTGGTAGTTGGGGTATTGTATTGTATTTCTTAGCAAATATCAGTTGTATC
GTGACAACAAAACCATCAACCCCATAACATAACATAAAGAATCGTTTATAGTCAACATAG 6850       6860       6870       6880       6890       6900
ATTACCTATATCTATCTATACCAATAGTTTGGAATGTATTTGTAAGACATTTTTAAGATA
TAATGGATATAGATAGATATGGTTATCAAACCTTACATAAACATTCTGTAAAAATTCTAT 6910       6920       6930       6940       6950       6960
TTCAGAAGAGTTAGCCTTATGGGACTTGCTCTAAAGTGTGAATTGATGCACACAGCTTTA
AAGTCTTCTCAATCGGAATACCCTGAACGAGATTTCACACTTAACTACGTGTGTCGAAAT 6970       6980       6990       7000       7010       7020
TCGAGCATAGTTTTCAGTGTAATCACCGCCAAAAAATCCGCCCACTTCAAAGCATAACCC
AGCTCGTATCAAAAGTCACATTAGTGGCGGTTTTTTAGGCGGGTGAAGTTTCGTATTGGG 7030       7040       7050       7060       7070       7080
GTTCGCCCAACCTGTTACATTGCCGCTAAGAGGCTCTGACTGCTGTCGATTGCGATTACG
CAAGCGGGTTGGACAATGTAACGGCGATTCTCCGAGACTGACGACAGCTAACGCTAATGC 7090       7100       7110       7120       7130       7140
ATTACGACCAGATATCTGTGGGGCATGGGGATAAGGGGTATGTGGGCCGATGGCTGACAG
TAATGCTGGTCTATAGACACCCCGTACCCCTATTCCCCATACACCCGGCTACCGACTGTC 7150       7160       7170       7180       7190       7200
TGTGGCAGCCTCATTAGCATGTCGTGGCCAGGAGGAAAGTATGCTTCGATGAAGCTCCTC
ACACCGTCGGAGTAATCGTACAGCACCGGTCCTCCTTTCATACGAAGCTACTTCGAGGAG 7210       7220       7230       7240       7250       7260
CGGCGGCAGTGTGCGAAATCGCTTCGATCACCATCATCGCCATCGCCATGGCCACTCGAT
GCCGCCGTCACACGCTTTAGCGAAGCTAGTGGTAGTAGCGGTAGCGGTACCGGTGAGCTA
```

FIG._4K

```
       7270       7280       7290       7300       7310       7320
TGTCGAGTTGCACGCACGGCGATGCCAACAGTTGGTTGCCAGCGCTGCACTCGAAACACT
ACAGCTCAACGTGCGTGCCGCTACGGTTGTCAACCAACGGTCGCGACGTGAGCTTTGTGA 7330       7340       7350       7360       7370       7380
CGCTTCTTCCCACCGACCGCAAAGTGCCGGAAAAGCTAGAAAAAAAGCAAAAAAAAAAGT
GCGAAGAAGGGTGGCTGGCGTTTCACGGCCTTTTCGATCTTTTTTTCGTTTTTTTTTTCA 7390       7400       7410       7420       7430       7440
GGAAGAAAATTCGCGATAGAAAACGGAAAAATCGAAACGAACAAAAAAAGTCGGAATAAA
CCTTCTTTTAAGCGCTATCTTTTGCCTTTTAGCTTTGCTTGTTTTTTTCAGCCTTATTT 7450       7460       7470       7480       7490       7500
TCAAGGAAACATGGTGCTCGACATTAAGATGTGCCGATTTGATAATGTGCCCTGGGGCTT
AGTTCCTTTGTACCACGAGCTGTAATTCTACACGGCTAAACTATTACACGGGACCCCGAA 7510       7520       7530       7540       7550       7560
TCGCCTGGTGGGCGGGGCGGACTACGATTATCCGCTGACGGTGGTTAAGGTTAGGCCCGA
AGCGGACCACCCGCCCCGCCTGATGCTAATAGGCGACTGCCACCAATTCCAATCCGGGCT 7570       7580       7590       7600       7610       7620
TTCGAAAAAAGAACGAAATCTATATGCTGCAACCCCCACCCCCCACGCATCACCTCAGC
AAGCTTTTTTCTTGCTTTAGATATACGACGTTGGGGGTGGGGGGGTGCGTAGTGGAGTCG 7630       7640       7650       7660       7670       7680
CCATTCACCTGGCGGATGTTCATAGACCAGTGGAAAATATTGCTCACTATGCAGCTGATG
GGTAAGTGGACCGCCTACAAGTATCTGGTCACCTTTTATAACGAGTGATACGTCGACTAC 7690       7700       7710       7720       7730       7740
AATCACATTGGATTAATTCGATACGATACGTTCGAATCAGTTTTATTTGTTCGATTGCAA
TTAGTGTAACCTAATTAAGCTATGCTATGCAAGCTTAGTCAAAATAAACAAGCTAACGTT 7750       7760       7770       7780       7790       7800
TATTACGTAACGCCGCGATGCGTGTGTGTCCATTCGGATTTGCTGCATTGGCAAATTAGT
ATAATGCATTGCGGCGCTACGCACACACAGGTAAGCCTAAACGACGTAACCGTTTAATCA 7810       7820       7830       7840       7850       7860
TAATTAAAGTAATTCCTCTCGCTTTTGTTTATCTAATCGACAGGGCCATACATTTCCCGC
ATTAATTTCATTAAGGAGAGCGAAAACAAATAGATTAGCTGTCCCGGTATGTAAAGGGCG 7870       7880       7890       7900       7910       7920
TAATGAGCCGCATAATGGCAGCGGCAATAAACTTATTCAAATTTTAATTGTGTTTCGCTG
ATTACTCGGCGTATTACCGTCGCCGTTATTTGAATAAGTTTAAAATTAACACAAAGCGAC 7930       7940       7950       7960       7970       7980
GCAGTTGGTCCTTTGTTTGTGCATAAATTGCATTTGGCAATTCGCATTTTGTAACATTGT
CGTCAACCAGGAAACAAACACGTATTTAACGTAAACCGTTAAGCGTAAAACATTGTAACA 7990       8000       8010       8020       8030       8040
GTTGACAATTCGCAACCAGCAACAATAACAAAAATACAATACATACAATACTATAGCATC
CAACTGTTAAGCGTTGGTCGTTGTTATTGTTTTTATGTTATGTATGTTATGATATCGTAG
```

FIG._4L

```
       8050       8060       8070       8080       8090       8100
GTCGTAAATCCGAAACAAATGCGATTTTTAATTGGCAAACTGCTAAGCGCATAAAACAAA
CAGCATTTAGGCTTTGTTTACGCTAAAAATTAACCGTTTGACGATTCGCGTATTTTGTTT 8110       8120       8130       8140       8150       8160
TGACCGAAATGCGAGGGGCGCTAAAAAATCCCATCCCTTCGATACGAATAAATCAATTTA
ACTGGCTTTACGCTCCCCGCGATTTTTAGGGTAGGGAAGCTATGCTTATTTAGTTAAAT 8170       8180       8190       8200       8210       8220
AGCCGCAGAGTCAAGGAAGGGAGGTCATAAATTGTTTTGACTTTTTGGTTATTTTTTTT
TCGGCGTCTCAGTTCCTTCCCTCCAGTATTTAACAAAACTGAAAAACCAATAAAAAAAA 8230       8240       8250       8260       8270       8280
TTACCGTTTTACATAAACAAATTATGCTATGGGTTATTTTAAATTCCGATCAATTTATAA
AATGGCAAAATGTATTTGTTTAATACGATACCCAATAAAATTTAAGGCTAGTTAAATATT 8290       8300       8310       8320       8330       8340
AATGTTTGTGCTTTGGGATATGCATACCATGAAAAAATGGAAGTTTATTGTAAATGAATT
TTACAAACACGAAACCCTATACGTATGGTACTTTTTACCTTCAAATAACATTTACTTAA 8350       8360       8370       8380       8390       8400
ATTAACTTCACAAGCTGGCTGATAGAGAAAAAACTGAAAAATGTCCGGAATGTTCTTCAT
TAATTGAAGTGTTCGACCGACTATCTCTTTTTTGACTTTTTACAGGCCTTACAAGAAGTA 8410       8420       8430       8440       8450       8460
TCCAATGAACTCCCTAAATTAACTTAGCTAATTTATTCCTTATACTAATACTCCGCTTTT
AGGTTACTTGAGGGATTTAATTGAATCGATTAAATAAGGAATATGATTATGAGGCGAAAA 8470       8480       8490       8500       8510       8520
AAGAATTCCTTACTACATGTTAGAGACTCAAAAGCACATCCTTCGACTCGAGTCCATAT
TTCTTAAGGAATGATGTACAATCTCTGAGTTTTCGTGTAGGAAGCTGAGCTCAGGTATA 8530       8540       8550       8560       8570       8580
TACTTTATGGAATGTGCCAACACACCTTCACATATTGGCTCTGCAAACACTAAACAATCC
ATGAAATACCTTACACGGTTGTGTGGAAGTGTATAACCGAGACGTTTGTGATTTGTTAGG 8590       8600       8610       8620       8630       8640
TTGGTAATCTTTTGAAAAACCTCTGTTTACACTACCACTCTTCGTCATGCTGCTCGCCAC
AACCATTAGAAAACTTTTGGAGACAAATGTGATGGTGAGAAGCAGTACGACGAGCGGTG 8650       8660       8670       8680       8690       8700
ATACAGTCTGGTACATAGATGTATGGCCCAGCTAAGCCCAAAGCCTTTGTTCTATAAATA
TATGTCAGACCATGTATCTACATACCGGGTCGATTCGGGTTTCGGAAACAAGATATTTAT 8710       8720       8730       8740       8750       8760
TTCGCAACCTCCGACGATGTCGAGTGCTTTTTGCTCTGCGAATTCACCGCTGGAAATTGA
AAGCGTTGGAGGCTGCTACAGCTCACGAAAACGAGACGCTTAAGTGGCGACCTTTAACT 8770       8780       8790       8800       8810       8820
CTCTACCATAAGTGAAATGCAAGAGACCCCTGGGACTGAAAGGAAAGACCCTCAACTTGG
GAGATGGTATTCACTTTACGTTCTCTGGGGACCCTGACTTTCCTTTCTGGGAGTTGAACC
```

FIG._4M

```
      8830      8840      8850      8860      8870      8880
TTGGGTGAAATGGTGGAGTCTCCAACCCTCCACCTGCTCCTTGTGCCAACCACTTTTTTT
AACCCACTTTACCACCTCAGAGGTTGGGAGGTGGACGAGGAACACGGTTGGTGAAAAAAA 8890      8900      8910      8920      8930      8940
TTTTTGCAGTATTTGCATTACTAAGTCCTCTTGGCAGTCGGTGTCGTGACTTTCTGGTTA
AAAAACGTCATAAACGTAATGATTCAGGAGAACCGTCAGCCACAGCACTGAAAGACCAAT 8950      8960      8970      8980      8990      9000
TGAACCCTGCTTTCTCATAACGGAAACGAAAACAATCGCGTTTATTTGCCCACGAAAGTG
ACTTGGGACGAAAGAGTATTGCCTTTGCTTTTGTTAGCGCAAATAAACGGGTGCTTTCAC 9010      9020      9030      9040      9050      9060
TTACAAAACTGCCTGAATTATGCAATAGAATTCTTTGAACAGAGTGCTAAGATATTTCGC
AATGTTTTGACGGACTTAATACGTTATCTTAAGAAACTTGTCTCACGATTCTATAAAGCG 9070      9080      9090      9100      9110      9120
ATTTTGAAGGCGAAACATAATTCATCCATAACTATTAGTTTGATGAATTCTCACTTCGTA
TAAAACTTCCGCTTTGTATTAAGTAGGTATTGATAATCAAACTACTTAAGAGTGAAGCAT 9130      9140      9150      9160      9170      9180
TGCTGGCAATTTTGAAGGCCGAAGTGGCAAAACCATTTTAAATGAATTCCTACAATTTAT
ACGACCGTTAAAACTTCCGGCTTCACCGTTTTGGTAAAATTTACTTAAGGATGTTAAATA 9190      9200      9210      9220      9230      9240
ATGCTCAATTTGCGCCAATTTGTCTGTACTTTATTACCCACAAAAGCCATAAAGCTTATA
TACGAGTTAAACGCGGTTAAACAGACATGAAATAATGGGTGTTTTCGGTATTTCGAATAT 9250      9260      9270      9280      9290      9300
TTGTATTTAGTTGTTATTGTTCTCGCAACATTTTCACTTTGATTTATAGTTGCGAAAATA
AACATAAATCAACAATAACAAGAGCGTTGTAAAAGTGAAACTAAATATCAACGCTTTTAT 9310      9320      9330      9340      9350      9360
AATGTTGGCAAATGCAAATTTTTGAAACGATATTCTCTTACACGGTCATTTGGTACCATT
TTACAACCGTTTACGTTTAAAAACTTTGCTATAAGAGAATGTGCCAGTAAACCATGGTAA 9370      9380      9390      9400      9410      9420
TCCGGAATATACATTTACCAATTTTCCAAAAAAGAGCCATAAATTGTATTATCCAATTA
AGGCCTTATATGTAAATGGTTAAAAGGTTTTTTCTCGGTATTTAACATAATAGGTTAAT 9430      9440      9450      9460      9470      9480
AAACGATTAGTCCAGTGGGTTTTTATTTCTAAAAATTTAATTTTGTAATTAGAGAAAACT
TTTGCTAATCAGGTCACCCAAAAATAAAGATTTTAAATTAAAACATTAATCTCTTTTGA 9490      9500      9510      9520      9530      9540
ATTGTGAACTTTGGATGACCTAGAAAGTTTCATTAGTTGTACATTATTTTTTACCCCCGC
TAACACTTGAAACCTACTGGATCTTTCAAAGTAATCAACATGTAATAAAAAATGGGGGCG 9550      9560      9570      9580      9590      9600
TTTAAAATTGCAGAACTTCTGTAAAAAAAGCTTTTACAAGCTATTTAAATATTAGTGGT
AAATTTTAACGTCTTGAAGACATTTTTTTTCGAAAATGTTCGATAAATTTATAATCACCA
```

FIG._4N

```
             9610      9620      9630      9640      9650      9660
        AGAGTTGTTTGAACATTTATCTTTTTGGAATCAGCAATATTTGGTTCTCTATCCTTACAA
        TCTCAACAAACTTGTAAATAGAAAAACCTTAGTCGTTATAAACCAAGAGATAGGAATGTT 9670      9680      9690      9700      9710      9720
        ATTAATCTTCTCTTTAAGTGAACTCATAACTTTGTATATATGTACGTATGTAGAATCATC
        TAATTAGAAGAGAAATTCACTTGAGTATTGAAACATATATACATGCATACATCTTAGTAG 9730      9740      9750      9760      9770      9780
        CTTCAACTCAAACATTTCCATCCGGCGAAACAATGCAATATTTGAGTGGTTAGACATGGG
        GAAGTTGAGTTTGTAAAGGTAGGCCGCTTTGTTACGTTATAAACTCACCAATCTGTACCC 9790      9800      9810      9820      9830      9840
        TAATTCCACTTGACTCGCTTAACTGAAGTGTCGTTAATGAGCTGCCACTTCTACTCGAGC
        ATTAAGGTGAACTGAGCGAATTGACTTCACAGCAATTACTCGACGGTGAAGATGAGCTCG 9850      9860      9870      9880      9890      9900
        ACCCCTCGTTCTGAGCCCCCAGCCCCCACAGATCCTCTGTAGCCCCCCCATCTCCTTGGG
        TGGGGAGCAAGACTCGGGGGTCGGGGGTGTCTAGGAGACATCGGGGGGGTAGAGGAACCC 9910      9920      9930      9940      9950      9960
        CATTGTCTTCGGTTCTGTTGGGTTTGTGCGTGATTGTATGATTGTCTGTTCGGGGGTCTG
        GTAACAGAAGCCAAGACAACCCAAACACGCACTAACATACTAACAGACAAGCCCCCAGAC 9970      9980      9990     10000     10010     10020
        GGTCTGCTGGTCTTTGTTTTGTTGACATTTGGCGCGCGTTTTATTTTTATGCACTTAGCA
        CCAGACGACCAGAAACAAAACAACTGTAAACCGCGCGCAAAATAAAAATACGTGAATCGT 10030     10040     10050     10060     10070     10080
        CGCGACGTCGCCGTTGTCGGCTAATAGAAATTTCCCCATTATCGCATCGCATCCCATTGT
        GCGCTGCAGCGGCAACAGCCGATTATCTTTAAAGGGGTAATAGCGTAGCGTAGGGTAACA 10090     10100     10110     10120     10130     10140
        ATTGTATCTCGGCTATCTCGACTATCTCGGCCTCGCACTCATTCTATCGCCACATTCCCA
        TAACATAGAGCCGATAGAGCTGATAGAGCCGGAGCGTGAGTAAGATAGCGGTGTAAGGGT 10150     10160     10170     10180     10190     10200
        TATCCGCATCTGAATCGGGCGATATCTAGGCATTCCCATCTAGATCTAAACATGTCCATA
        ATAGGCGTAGACTTAGCCCGCTATAGATCCGTAAGGGTAGATCTAGATTTGTACAGGTAT 10210     10220     10230     10240     10250     10260
        TGCTTCAACGTTAGGTGACCGAGGGCAGCATTGCTGACGAGGCTGGACTGCGGGTCGAGG
        ACGAAGTTGCAATCCACTGGCTCCCGTCGTAACGACTGCTCCGACCTGACGCCCAGCTCC 10270     10280     10290     10300     10310     10320
        ATATCATCGTGCGCATCAATGACACGGCTGCCACGCCCCTTACCCACGACGAGGCCCACC
        TATAGTAGCACGCGTAGTTACTGTGCCGACGGTGCGGGGAATGGGTGCTGCTCCGGGTGG 10330     10340     10350     10360     10370     10380
        GCCTCATTATGGGCAGTGGAAGCGTCTTCTATTTTGGCGTCTACCGGTGAGCTTTCCCAT
        CGGAGTAATACCCGTCACCTTCGCAGAAGATAAAACCGCAGATGGCCACTCGAAAGGGTA
```

FIG._40

```
          10390     10400     10410     10420     10430     10440
     CCTTCTATTCCATACCATTCCGTTTCGTTCTCTTACTGCTCGTGGTCGTGGTCCTCGTCC
     GGAAGATAAGGTATGGTAAGGCAAAGCAAGAGAATGACGAGCACCAGCACCAGGAGCAGG 10450     10460     10470     10480     10490     10500
     TTGTCCGGTTCCTTTACTACTACTCTTTGTATCCCATCCACCGAGGACCATTTATCACAG
     AACAGGCCAAGGAAATGATGATGAGAAACATAGGGTAGGTGGCTCCTGGTAAATAGTGTC 10510     10520     10530     10540     10550     10560
     CTGAGCGGGCTAACAACCCAAGAACGTTTCCTCATGCCCCTGCTCAAGGTAATCTACTTG
     GACTCGCCCGATTGTTGGGTTCTTGCAAAGGAGTACGGGGACGAGTTCCATTAGATGAAC 10570     10580     10590     10600     10610     10620
     TTCAAGAAATTCACAAACCACAAACGACCTCGAGAGAAATGGAAAAAATATGACAAATTT
     AAGTTCTTTAAGTGTTTGGTGTTTGCTGGAGCTCTCTTTACCTTTTTTATACTGTTTAAA 10630     10640     10650     10660     10670     10680
     TCGTGATTTAAGAATAAAGTTCTGGAAAAATAAAGCGCTTTCTTAAAAAGTTGTCTGGGT
     AGCACTAAATTCTTATTTCAAGACCTTTTATTTCGCGAAAGAATTTTTCAACAGACCCA 10690     10700     10710     10720     10730     10740
     AAAATGACATTTGGTTAATATATCATAATAGTTAATTTTATTATAATTATAAACTAAGAA
     TTTTACTGTAAACCAATTATATAGTATTATCAATTAAAATAATATTAATATTTGATTCTT 10750     10760     10770     10780     10790     10800
     AAGTTAAATTCAAAAACCCACCTAGCCCCATTAGTTTTGAAAATTACCCTACCATTTTAG
     TTCAATTTAAGTTTTTGGGTGGATCGGGGTAATCAAAACTTTTAATGGGATGGTAAAATC 10810     10820     10830     10840     10850     10860
     AAGCAATTTATATTATTTGAATTAAGTTTGTATTTCAACTTTTTCGGGTTATGAATAATT
     TTCGTTAAATATAATAAACTTAATTCAAACATAAAGTTGAAAAAGCCCAATACTTATTAA 10870     10880     10890     10900     10910     10920
     ATTCTTAGAGTGTCCCCGAAACCAGGGCTCCATCTCAGGTATTCCACGTTACGGAATTAA
     TAAGAATCTCACAGGGGCTTTGGTCCCGAGGTAGAGTCCATAAGGTGCAATGCCTTAATT 10930     10940     10950     10960     10970     10980
     TTCTAATGTTCATAAATTCTGCTCACTTTTTGGTCACTTGGATCCATGTGCAGGGAGAAC
     AAGATTACAAGTATTTAAGACGAGTGAAAAACCAGTGAACCTAGGTACACGTCCCTCTTG 10990     11000     11010     11020     11030     11040
     GAGGAGGACGCTTACGAGTGCCTAAAGAAGTTTCCCACGAGCGAGGGTTCGTTGACCAAG
     CTCCTCCTGCGAATGCTCACGGATTTCTTCAAAGGGTGCTCGCTCCCAAGCAACTGGTTC 11050     11060     11070     11080     11090     11100
     TCACCAATGCCGACCATTTCACCGTCGCCGACTCCATCGCTGTCCCAGCTGACGGAAACC
     AGTGGTTACGGCTGGTAAAGTGGCAGCGGCTGAGGTAGCGACAGGGTCGACTGCCTTTGG 11110     11120
     ACAAATGCCCGTACTCCGGA
     TGTTTACGGGCATGAGGCCT
```

FIG._4P

```
              10        20        30        40        50        60
         TTCACGCATCCATACTTAAACACCACTTCATCACTCATGGGCATCGAGATGAGGTGTCAG
         AAGTGCGTAGGTATGAATTTGTGGTGAAGTAGTGAGTACCCGTAGCTCTACTCCACAGTC
                                            M   G   I   E   M   R   C   Q>
                                           ____CODING REGION_____>
                                            M   G   I   E   M   R   C   Q>
                                            ____SIGNAL PEPTIDE_____>

70        80        90       100       110       120
         GACAGGAGGATCCTGCTACCTAGCCTACTCCTACTAATCCTTATGATCGGCGGTGTCCAG
         CTGTCCTCCTAGGACGATGGATCGGATGAGGATGATTAGGAATACTAGCCGCCACAGGTC
          D   R   R   I   L   L   P   S   L   L   L   I   L   M   I   G   G   V   Q>
         _____CODING REGION_____>
          D   R   R   I   L   L   P   S   L   L   L   I   L   M   I   G   G   V   Q>
         _____SIGNAL PEPTIDE_____>

130       140       150       160       170       180
         GCCACCATGAAGTTGTGCGGCCGCAAACTGCCCGAAACTCTCTCCAAGCTCTGTGTGTAT
         CGGTGGTACTTCAACACGCCGGCGTTTGACGGGCTTTGAGAGAGGTTCGAGACACACATA
          A   T   M   K   L   C   G   R   K   L   P   E   T   L   S   K   L   C   V   Y>
         _____CODING REGION_____>
          A>
         ____>
              T   M   K   L   C   G   R   K   L   P   E   T   L   S   K   L   C   V   Y>
                     _____B PEPTIDE_____>

190       200       210       220       230       240
         GGCTTCAACGCAATGACCAAGAGAACTTTGGACCCCGTGAACTTCAATCAGATCGATGGC
         CCGAAGTTGCGTTACTGGTTCTCTTGAAACCTGGGGCACTTGAAGTTAGTCTAGCTACCG
          G   F   N   A   M   T   K   R   T   L   D   P   V   N   F   N   Q   I   D   G>
         _____CODING REGION_____>
          G   F   N   A   M   T>
          ____B PEPTIDE____>
```

FIG._5A

```
                    K   R   T   L   D   P   V   N   F   N   Q   I   D   G>
                    _____C PEPTIDE_____>

250         260         270         280         290         300
TTCGAAGACCGTTCCCTGCTGGAAAGACTGTTGAGTGATAGTTCGGTTCAGATGCTCAAG
AAGCTTCTGGCAAGGGACGACCTTTCTGACAACTCACTATCAAGCCAAGTCTACGAGTTC
  F   E   D   R   S   L   L   E   R   L   L   S   D   S   S   V   Q   M   L   K>
  _____CODING REGION_____>
  F   E   D   R   S   L   L   E   R   L   L   S   D   S   S   V   Q   M   L   K>
  _____C PEPTIDE_____>

310         320         330         340         350         360
ACTCGACGTCTTCGGGATGGAGTCTTCGACGAGTGTTGCCTGAAGTCGTGCACCATGGAT
TGAGCTGCAGAAGCCCTACCTCAGAAGCTGCTCACAACGGACTTCAGCACGTGGTACCTA
  T   R   R   L   R   D   G   V   F   D   E   C   C   L   K   S   C   T   M   D>
  _____CODING REGION_____>
  T   R   R>
  _____>
              L   R   D   G   V   F   D   E   C   C   L   K   S   C   T   M   D>
              _____A PEPTIDE_____>

370         380         390         400         410         420
GAGGTGCTGAGATATTGTGCTGCCAAGCCGAGAACGTAAACCTCGTAAACCTATTAACCC
CTCCACGACTCTATAACACGACGGTTCGGCTCTTGCATTTGGAGCATTTGGATAATTGGG
  E   V   L   R   Y   C   A   A   K   P   R   T   *>
  _____CODING REGION_____>
  E   V   L   R   Y   C   A   A   K   P   R   T>
  _____A PEPTIDE_____>

AATG
TTAC
```

FIG._5B

```
              10        20        30        40        50        60
ACTGCATTAGCTAGCGCTTCCGATTTAGTGGTATAAATACCAGTTGCAGCCCAGAGCATT
TGACGTAATCGATCGCGAAGGCTAAATCACCATATTTATGGTCAACGTCGGGTCTCGTAA 70        80        90       100       110       120
CACTGCATATCCAAGATGTTTAGCCAGCACAACGGTGCAGCAGTACATGGCCTTCGGCTC
GTGACGTATAGGTTCTACAAATCGGTCGTGTTGCCACGTCGTCATGTACCGGAAGCCGAG
                    M   F   S   Q   H   N   G   A   A   V   H   G   L   R   L>
                        _____CODING REGION_____>
                    M   F   S   Q   H   N   G   A   A   V   H   G   L   R   L>
                        _____SIGNAL PEPTIDE_____>

130       140       150       160       170       180
CAGTCGCTGCTCATCGCAGCCATGCTCACCGCTGCAATGGCAATGGTCACGCCGACTGGC
GTCAGCGACGAGTAGCGTCGGTACGAGTGGCGACGTTACCGTTACCAGTGCGGCTGACCG
 Q   S   L   L   I   A   A   M   L   T   A   A   M   A   M   V   T   P   T   G>
 _____CODING REGION_____>
 Q   S   L   L   I   A   A   M   L   T   A   A   M   A>
 _____SIGNAL PEPTIDE_____>
                                                    M   V   T   P   T   G>
                                                      ___B PEPTIDE_____>

190       200       210       220       230       240
AGTGGTCACCAGTTGCTGCCCCCCGGAAACCACAAACTCTGCGGCCCCGCACTGTCCGAT
TCACCAGTGGTCAACGACGGGGGGCCTTTGGTGTTTGAGACGCCGGGGCGTGACAGGCTA
 S   G   H   Q   L   L   P   P   G   N   H   K   L   C   G   P   A   L   S   D>
 _____CODING REGION_____>
 S   G   H   Q   L   L   P   P   G   N   H   K   L   C   G   P   A   L   S   D>
 _____B PEPTIDE_____>

250       260       270       280       290       300
GCCATGGATGTGGTGTGTCCCCATGGCTTTAATACGCTGCCAAGGAAACGTGAAAGCTTG
CGGTACCTACACCACACAGGGGTACCGAAATTATGCGACGGTTCCTTTGCACTTTCGAAC
 A   M   D   V   V   C   P   H   G   F   N   T   L   P   R   K   R   E   S   L>
 _____CODING REGION_____>
 A   M   D   V   V   C   P   H   G   F   N   T   L   P>
 _____B PEPTIDE_____>
                                                    R   K   R   E   S   L>
                                                      __C PEPTIDE_____>
```

FIG._6A

```
          310       320       330       340       350       360
CTGGGCAACAGCGACGACGACGAGGACACGGAGCAGGAGGTGCAGGATGATAGCAGCATG
GACCCGTTGTCGCTGCTGCTGCTCCTGTGCCTCGTCCTCCACGTCCTACTATCGTCGTAC
   L  G  N  S  D  D  D  E  D  T  E  Q  E  V  Q  D  D  S  S  M>
   _____CODING REGION_____>
   L  G  N  S  D  D  D  E  D  T  E  Q  E  V  Q  D  D  S  S  M>
   _____C PEPTIDE_____>

370       380       390       400       410       420
TGGCAGACACTGGACGGGGCAGGATACTCTTTTAGTCCACTGCTAACCAATCTGTACGGA
ACCGTCTGTGACCTGCCCCGTCCTATGAGAAAATCAGGTGACGATTGGTTAGACATGCCT
   W  Q  T  L  D  G  A  G  Y  S  F  S  P  L  L  T  N  L  Y  G>
   _____CODING REGION_____>
   W  Q  T  L  D  G  A  G  Y  S  F  S  P  L  L  T  N  L  Y  G>
   _____C PEPTIDE_____>

430       440       450       460       470       480
TCCGAGGTCCTGATCAAGATGCGTCGCCACAGGAGACACCTGACCGGTGGCGTCTACGAC
AGGCTCCAGGACTAGTTCTACGCAGCGGTGTCCTCTGTGGACTGGCCACCGCAGATGCTG
   S  E  V  L  I  K  M  R  R  H  R  R  H  L  T  G  G  V  Y  D>
   _____CODING REGION_____>
   S  E  V  L  I  K  M  R  R  H  R  R>
   _____C PEPTIDE_____>
                                       H  L  T  G  G  V  Y  D>
                                       _____A PEPTIDE_____>

490       500       510       520       530       540
GAGTGCTGCGTCAAGACCTGCAGCTACTTGGAGTTAGCCATCTACTGTCTACCGAAATAG
CTCACGACGCAGTTCTGGACGTCGATGAACCTCAATCGGTAGATGACAGATGGCTTTATC
   E  C  C  V  K  T  C  S  Y  L  E  L  A  I  Y  C  L  P  K  *>
   _____CODING REGION_____>
   E  C  C  V  K  T  C  S  Y  L  E  L  A  I  Y  C  L  P  K>
   _____A PEPTIDE_____>

550       560       570       580       590       600
GACACTTGGCCAACACACACACATTCATTACCCAGCATGCATACACATACATACATACAT
CTGTGAACCGGTTGTGTGTGTGTAAGTAATGGGTCGTACGTATGTGTATGTATGTATGTA

ACGAACACT
TGCTTGTGA
```

FIG._6B

```
          10        20        30        40        50        60
ATGAGCAAGCCTTTGTCCTTCATCTCGATGGTGGCCGTGATTTTGCTGGCCAGCTCCACA
TACTCGTTCGGAAACAGGAAGTAGAGCTACCACCGGCACTAAAACGACCGGTCGAGGTGT
  M   S   K   P   L   S   F   I   S   M   V   A   I   L   L   A   S   S   T>
                              _____CODING REGION_____>
  M   S   K   P   L   S   F   I   S   M   V   A   I   L   L   A   S   S   T>
                              _____SIGNAL PEPTIDE_____>

70        80        90       100       110       120
GTGAAGTTGGCCCAAGGAACGCTCTGCAGTGAAAAGCTCAACGAGGTGCTGAGTATGGTG
CACTTCAACCGGGTTCCTTGCGAGACGTCACTTTTCGAGTTGCTCCACGACTCATACCAC
  V   K   L   A   Q   G   T   L   C   S   E   K   L   N   E   V   L   S   M   V>
                              _____CODING REGION_____>
  V   K   L   A   Q   G>
  ___SIGNAL PEPT_____>
                      T   L   C   S   E   K   L   N   E   V   L   S   M   V>
                              _____B PEPTIDE_____>

130       140       150       160       170       180
TGCGAGGAGTATAATCCCGTGATTCCACACAAGCGCGCCATGCCCGGTGCCGACAGCGAT
ACGCTCCTCATATTAGGGCACTAAGGTGTGTTCGCGCGGTACGGGCCACGGCTGTCGCTA
  C   E   E   Y   N   P   V   I   P   H   K   R   A   M   P   G   A   D   S   D>
                              _____CODING REGION_____>
  C   E   E   Y   N   P   V   I   P   H>
        _____B PEPTIDE_____>
                                      K   R   A   M   P   G   A   D   S   D>
                                          _____C PEPTIDE_____>

190       200       210       220       230       240
CTGGATGCCCTCAATCCCCTGCAGTTTGTCCAGGAGTTCGAGGAGGAGGATAACTCGATA
GACCTACGGGAGTTAGGGGACGTCAAACAGGTCCTCAAGCTCCTCCTCCTATTGAGCTAT
  L   D   A   L   N   P   L   Q   F   V   Q   E   F   E   E   E   D   N   S   I>
                              _____CODING REGION_____>
  L   D   A   L   N   P   L   Q   F   V   Q   E   F   E   E   E   D   N   S   I>
                              _____C PEPTIDE_____>
```

FIG._7A

```
         250        260        270        280        290        300
TCGGAACCGCTGCGAAGTGCCCTCTTTCCTGGGAGCTATCTTGGGGGTGTACTCAATTCC
AGCCTTGGCGACGCTTCACGGGAGAAAGGACCCTCGATAGAACCCCCACATGAGTTAAGG
   S   E   P   L   R   S   A   L   F   P   G   S   Y   L   G   G   V   L   N   S>
_____CODING REGION_____>
   S   E   P   L   R   S   A   L   F   P   G   S   Y   L   G   G   V   L   N   S>
_____C PEPTIDE_____>

310        320        330        340        350        360
CTGGCTGAAGTCCGGAGGCGAACTCGCCAACGGCAAGGAATCGTGGAGAGGTGCTGCAAA
GACCGACTTCAGGCCTCCGCTTGAGCGGTTGCCGTTCCTTAGCACCTCTCCACGACGTTT
   L   A   E   V   R   R   R   T   R   Q   R   Q   G   I   V   E   R   C   C   K>
_____CODING REGION_____>
   L   A   E   V   R   R   R>
_____C PEPTIDE_____>
                           T   R   Q   R   Q   G   I   V   E   R   C   C   K>
                          _____A PEPTIDE_____>

370        380        390        400        410        420
AAGTCCTGTGATATGAAGGCTCTGCGGGAGTACTGCTCCGTGGTCAGAAATTAGGCCTCC
TTCAGGACACTATACTTCCGAGACGCCCTCATGACGAGGCACCAGTCTTTAATCCGGAGG
   K   S   C   D   M   K   A   L   R   E   Y   C   S   V   V   R   N   *>
_____CODING REGION_____>
   K   S   C   D   M   K   A   L   R   E   Y   C   S   V   V   R   N>
_____A PEPTIDE_____>

430        440
TAATGCGAAAATCATTGACCCCAACTGA
ATTACGCTTTTAGTAACTGGGGTTGACT
```

FIG._7B

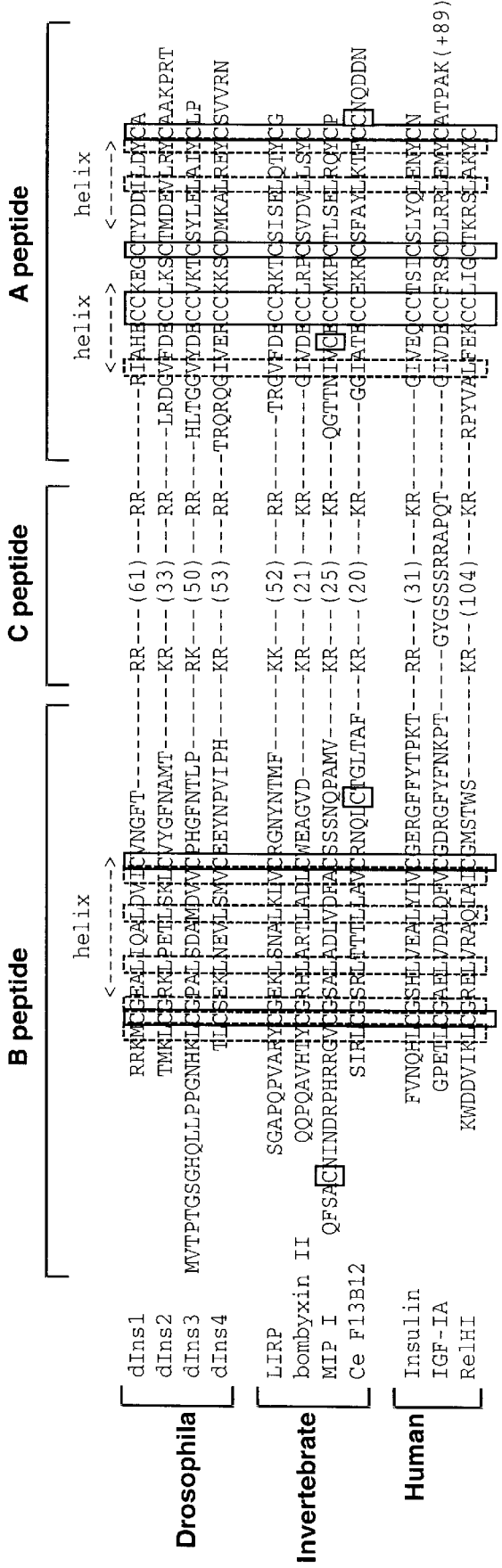
FIG._8

SEQUENCE LISTING

```
<160> NUMBER OF SEQ ID NOS: 45

<210> SEQ ID NO 1
<211> LENGTH: 424
<212> TYPE: DNA
<213> ORGANISM: Drosophila melanogaster
<220> FEATURE:
<221> NAME/KEY: CDS
<222> LOCATION: (37)..(399)

<400> SEQUENCE: 1
ttcacgcatc catacttaaa caccacttca tcactc atg ggc atc gag atg agg         54
                                      Met Gly Ile Glu Met Arg
                                      1               5 tgt cag gac agg agg atc ctg cta cct agc cta ctc cta cta atc ctt       102
Cys Gln Asp Arg Arg Ile Leu Leu Pro Ser Leu Leu Leu Leu Ile Leu
            10                  15                  20 atg atc ggc ggt gtc cag gcc acc atg aag ttg tgc ggc cgc aaa ctg       150
```

```
Met Ile Gly Gly Val Gln Ala Thr Met Lys Leu Cys Gly Arg Lys Leu
             25                  30                  35 ccc gaa act ctc tcc aag ctc tgt gtg tat ggc ttc aac gca atg acc      198
Pro Glu Thr Leu Ser Lys Leu Cys Val Tyr Gly Phe Asn Ala Met Thr
         40                  45                  50 aag aga act ttg gac ccc gtg aac ttc aat cag atc gat ggc ttc gaa      246
Lys Arg Thr Leu Asp Pro Val Asn Phe Asn Gln Ile Asp Gly Phe Glu
 55                  60                  65                  70 gac cgt tcc ctg ctg gaa aga ctg ttg agt gat agt tcg gtt cag atg      294
Asp Arg Ser Leu Leu Glu Arg Leu Leu Ser Asp Ser Ser Val Gln Met
                 75                  80                  85 ctc aag act cga cgt ctt cgg gat gga gtc ttc gac gag tgt tgc ctg      342
Leu Lys Thr Arg Arg Leu Arg Asp Gly Val Phe Asp Glu Cys Cys Leu
             90                  95                 100 aag tcg tgc acc atg gat gag gtg ctg aga tat tgt gct gcc aag ccg      390
Lys Ser Cys Thr Met Asp Glu Val Leu Arg Tyr Cys Ala Ala Lys Pro
         105                 110                 115 aga acg taa acctcgtaaa cctattaacc caatg                               424
Arg Thr
 120

<210> SEQ ID NO 2
<211> LENGTH: 120
<212> TYPE: PRT
<213> ORGANISM: Drosophila melanogaster

<400> SEQUENCE: 2

Met Gly Ile Glu Met Arg Cys Gln Asp Arg Arg Ile Leu Leu Pro Ser
 1               5                  10                  15

Leu Leu Leu Leu Ile Leu Met Ile Gly Gly Val Gln Ala Thr Met Lys
             20                  25                  30

Leu Cys Gly Arg Lys Leu Pro Glu Thr Leu Ser Lys Leu Cys Val Tyr
         35                  40                  45

Gly Phe Asn Ala Met Thr Lys Arg Thr Leu Asp Pro Val Asn Phe Asn
     50                  55                  60

Gln Ile Asp Gly Phe Glu Asp Arg Ser Leu Leu Glu Arg Leu Leu Ser
 65                  70                  75                  80

Asp Ser Ser Val Gln Met Leu Lys Thr Arg Arg Leu Arg Asp Gly Val
                 85                  90                  95

Phe Asp Glu Cys Cys Leu Lys Ser Cys Thr Met Asp Glu Val Leu Arg
            100                 105                 110

Tyr Cys Ala Ala Lys Pro Arg Thr
            115                 120

<210> SEQ ID NO 3
<211> LENGTH: 609
<212> TYPE: DNA
<213> ORGANISM: Drosophila melanogaster
<220> FEATURE:
<221> NAME/KEY: CDS
<222> LOCATION: (76)..(540)

<400> SEQUENCE: 3
actgcattag ctagcgcttc cgatttagtg gtataaatac cagttgcagc ccagagcatt     60
cactgcatat ccaag atg ttt agc cag cac aac ggt gca gca gta cat ggc    111
                 Met Phe Ser Gln His Asn Gly Ala Ala Val His Gly
                  1               5                  10 ctt cgg ctc cag tcg ctg ctc atc gca gcc atg ctc acc gct gca atg    159
Leu Arg Leu Gln Ser Leu Leu Ile Ala Ala Met Leu Thr Ala Ala Met
         15                  20                  25
```

```
gca atg gtc acg ccg act ggc agt ggt cac cag ttg ctg ccc ccc gga      207
Ala Met Val Thr Pro Thr Gly Ser Gly His Gln Leu Leu Pro Pro Gly
    30                  35                  40 aac cac aaa ctc tgc ggc ccc gca ctg tcc gat gcc atg gat gtg gtg      255
Asn His Lys Leu Cys Gly Pro Ala Leu Ser Asp Ala Met Asp Val Val
45                  50                  55                  60 tgt ccc cat ggc ttt aat acg ctg cca agg aaa cgt gaa agc ttg ctg      303
Cys Pro His Gly Phe Asn Thr Leu Pro Arg Lys Arg Glu Ser Leu Leu
                65                  70                  75 ggc aac agc gac gac gac gag gac acg gag cag gag gtg cag gat gat      351
Gly Asn Ser Asp Asp Asp Glu Asp Thr Glu Gln Glu Val Gln Asp Asp
            80                  85                  90 agc agc atg tgg cag aca ctg gac ggg gca gga tac tct ttt agt cca      399
Ser Ser Met Trp Gln Thr Leu Asp Gly Ala Gly Tyr Ser Phe Ser Pro
        95                  100                 105 ctg cta acc aat ctg tac gga tcc gag gtc ctg atc aag atg cgt cgc      447
Leu Leu Thr Asn Leu Tyr Gly Ser Glu Val Leu Ile Lys Met Arg Arg
    110                 115                 120 cac agg aga cac ctg acc ggt ggc gtc tac gac gag tgc tgc gtc aag      495
His Arg Arg His Leu Thr Gly Gly Val Tyr Asp Glu Cys Cys Val Lys
125                 130                 135                 140 acc tgc agc tac ttg gag tta gcc atc tac tgt cta ccg aaa tag          540
Thr Cys Ser Tyr Leu Glu Leu Ala Ile Tyr Cys Leu Pro Lys
                145                 150 gacacttggc aacacacac acattcatta cccagcatgc atacacatac atacatacat     600
acgaacact                                                            609

<210> SEQ ID NO 4
<211> LENGTH: 154
<212> TYPE: PRT
<213> ORGANISM: Drosophila melanogaster

<400> SEQUENCE: 4

Met Phe Ser Gln His Asn Gly Ala Ala Val His Gly Leu Arg Leu Gln
1               5                   10                  15

Ser Leu Leu Ile Ala Ala Met Leu Thr Ala Ala Met Ala Met Val Thr
            20                  25                  30

Pro Thr Gly Ser Gly His Gln Leu Leu Pro Pro Gly Asn His Lys Leu
        35                  40                  45

Cys Gly Pro Ala Leu Ser Asp Ala Met Asp Val Val Cys Pro His Gly
    50                  55                  60

Phe Asn Thr Leu Pro Arg Lys Arg Glu Ser Leu Leu Gly Asn Ser Asp
65                  70                  75                  80

Asp Asp Glu Asp Thr Glu Gln Glu Val Gln Asp Asp Ser Ser Met Trp
                85                  90                  95

Gln Thr Leu Asp Gly Ala Gly Tyr Ser Phe Ser Pro Leu Leu Thr Asn
            100                 105                 110

Leu Tyr Gly Ser Glu Val Leu Ile Lys Met Arg Arg His Arg Arg His
        115                 120                 125

Leu Thr Gly Gly Val Tyr Asp Glu Cys Cys Val Lys Thr Cys Ser Tyr
    130                 135                 140

Leu Glu Leu Ala Ile Tyr Cys Leu Pro Lys
145                 150

<210> SEQ ID NO 5
<211> LENGTH: 448
<212> TYPE: DNA
```

```
<213> ORGANISM: Drosophila melanogaster
<220> FEATURE:
<221> NAME/KEY: CDS
<222> LOCATION: (1)..(414)

<400> SEQUENCE: 5 atg agc aag cct ttg tcc ttc atc tcg atg gtg gcc gtg att ttg ctg        48
Met Ser Lys Pro Leu Ser Phe Ile Ser Met Val Ala Val Ile Leu Leu
 1               5                  10                  15 gcc agc tcc aca gtg aag ttg gcc caa gga acg ctc tgc agt gaa aag        96
Ala Ser Ser Thr Val Lys Leu Ala Gln Gly Thr Leu Cys Ser Glu Lys
             20                  25                  30 ctc aac gag gtg ctg agt atg gtg tgc gag gag tat aat ccc gtg att       144
Leu Asn Glu Val Leu Ser Met Val Cys Glu Glu Tyr Asn Pro Val Ile
         35                  40                  45 cca cac aag cgc gcc atg ccc ggt gcc gac agc gat ctg gat gcc ctc       192
Pro His Lys Arg Ala Met Pro Gly Ala Asp Ser Asp Leu Asp Ala Leu
     50                  55                  60 aat ccc ctg cag ttt gtc cag gag ttc gag gag gag gat aac tcg ata       240
Asn Pro Leu Gln Phe Val Gln Glu Phe Glu Glu Glu Asp Asn Ser Ile
 65                  70                  75                  80 tcg gaa ccg ctg cga agt gcc ctc ttt cct ggg agc tat ctt ggg ggt       288
Ser Glu Pro Leu Arg Ser Ala Leu Phe Pro Gly Ser Tyr Leu Gly Gly
                 85                  90                  95 gta ctc aat tcc ctg gct gaa gtc cgg agg cga act cgc caa cgg caa       336
Val Leu Asn Ser Leu Ala Glu Val Arg Arg Arg Thr Arg Gln Arg Gln
            100                 105                 110 gga atc gtg gag agg tgc tgc aaa aag tcc tgt gat atg aag gct ctg       384
Gly Ile Val Glu Arg Cys Cys Lys Lys Ser Cys Asp Met Lys Ala Leu
        115                 120                 125 cgg gag tac tgc tcc gtg gtc aga aat tag gcctcctaat gcgaaaatca         434
Arg Glu Tyr Cys Ser Val Val Arg Asn
    130                 135 ttgacccaa ctga                                                         448

<210> SEQ ID NO 6
<211> LENGTH: 137
<212> TYPE: PRT
<213> ORGANISM: Drosophila melanogaster

<400> SEQUENCE: 6

Met Ser Lys Pro Leu Ser Phe Ile Ser Met Val Ala Val Ile Leu Leu
 1               5                  10                  15

Ala Ser Ser Thr Val Lys Leu Ala Gln Gly Thr Leu Cys Ser Glu Lys
             20                  25                  30

Leu Asn Glu Val Leu Ser Met Val Cys Glu Glu Tyr Asn Pro Val Ile
         35                  40                  45

Pro His Lys Arg Ala Met Pro Gly Ala Asp Ser Asp Leu Asp Ala Leu
     50                  55                  60

Asn Pro Leu Gln Phe Val Gln Glu Phe Glu Glu Glu Asp Asn Ser Ile
 65                  70                  75                  80

Ser Glu Pro Leu Arg Ser Ala Leu Phe Pro Gly Ser Tyr Leu Gly Gly
                 85                  90                  95

Val Leu Asn Ser Leu Ala Glu Val Arg Arg Arg Thr Arg Gln Arg Gln
            100                 105                 110

Gly Ile Val Glu Arg Cys Cys Lys Lys Ser Cys Asp Met Lys Ala Leu
        115                 120                 125

Arg Glu Tyr Cys Ser Val Val Arg Asn
    130                 135
```

<210> SEQ ID NO 7
<211> LENGTH: 11120
<212> TYPE: DNA
<213> ORGANISM: Drosophila melanogaster
<220> FEATURE:
<221> NAME/KEY: promoter
<222> LOCATION: (691)..(730)
<223> OTHER INFORMATION: DINS1 PUT. PROMOTER
<220> FEATURE:
<221> NAME/KEY: exon
<222> LOCATION: (864)..(1028)
<223> OTHER INFORMATION: DINS1 EXON 1
<220> FEATURE:
<221> NAME/KEY: exon
<222> LOCATION: (1090)..(1329)
<223> OTHER INFORMATION: DINS1 EXON2
<220> FEATURE:
<221> NAME/KEY: polyA_signal
<222> LOCATION: (1354)..(1354)
<223> OTHER INFORMATION: DINS2 PUT. POLY(A)SIGNAL
<220> FEATURE:
<221> NAME/KEY: promoter
<222> LOCATION: (2803)..(2842)
<223> OTHER INFORMATION: DINS2 PUT. PROMOTER
<220> FEATURE:
<221> NAME/KEY: exon
<222> LOCATION: (2940)..(3101)
<223> OTHER INFORMATION: DINS2 EXON1
<220> FEATURE:
<221> NAME/KEY: exon
<222> LOCATION: (3174)..(3362)
<223> OTHER INFORMATION: DINS2 EXON2
<220> FEATURE:
<221> NAME/KEY: polyA_signal
<222> LOCATION: (3657)..(3657)
<223> OTHER INFORMATION: DINS2 PUT. POLY(A)SIGNAL
<220> FEATURE:
<221> NAME/KEY: polyA_signal
<222> LOCATION: (3760)..(3760)
<223> OTHER INFORMATION: dINS4 PUT. POLY(A)SIGNAL
<220> FEATURE:
<221> NAME/KEY: misc_feature
<222> LOCATION: (4727)..(4977)
<223> OTHER INFORMATION: DINS4 EXON 2 (3' to 5')
<220> FEATURE:
<221> NAME/KEY: misc_feature
<222> LOCATION: (5051)..(5213)
<223> OTHER INFORMATION: DINS4 EXON 1 (3' to 5')
<220> FEATURE:
<221> NAME/KEY: promoter
<222> LOCATION: (5288)..(5327)
<223> OTHER INFORMATION: DINS PUT. PROMOTER (3' to 5')
<220> FEATURE:
<221> NAME/KEY: polyA_signal
<222> LOCATION: (5902)..(5902)
<223> OTHER INFORMATION: DINS3 PUT POLY(A) SIGNAL
<220> FEATURE:
<221> NAME/KEY: misc_feature
<222> LOCATION: (6079)..(6543)
<223> OTHER INFORMATION: DINS3
<220> FEATURE:
<221> NAME/KEY: promoter
<222> LOCATION: (6591)..(6652)
<223> OTHER INFORMATION: DINS3 PUT PROMOTER

<400> SEQUENCE: 7

```
gcttctgctc ggagagcggc tgacccgaat gggatagggc atctcctgtc cacaggaacg      60
aactccccat tatcgccctg cttggccttc atcgtcttca ccgccgattc aatcagtctc     120
caaggactat cgcagttgta gtgtccaaag ggaccaggtg gctccgatgc cgcactattg     180
gcattggagc cggaaaccga tcgtgctaac tcccagcagc ttctgtatat gtcgccctgc     240
gtggagtaga gtgtgtcaag gtggaggtca ctaatgtgcc agaagtagcc tgtcaacaaa     300
```

-continued

```
caagtagaat caagtaaatg tgttagttaa atacccatag atatatgtaa aagttgttgt      360
tttatttgct aagaaaagtt taatctatat cccagtttta cacaccagat ttttatgtcc      420
tgagcaattt cgtatgtatt tccccttcgt aaagtaagga tcgagattag actttgactt      480
tggttaagtc gggcaattcc tggccgggaa aggccatttc ctttcgcggg gcattttccc      540
gccggctggt cgagcgacaa aaataagaaa acctggtag ttcaaatgga atctcctgc       600 agctgactgt ttggttggtt gactgacctg gcccgaattt aactttctac ctggtcgcaa      660
tacgtgaagt caaaaagtca attagcgagt caacattttg agcgccggcc aactccaagg      720
atcagtatca tttggcatgc ccagcgatcg gtttgccaag agcacgagaa gttcgagata      780
ggacccagag ataccagaga taaggaggc ataccttta tgcccggtga gagcacggac       840
ggcggagtga agatcgagc agg atg agc ctg att aga ctg gga ctg gcg ctg     893
                        Met Ser Leu Ile Arg Leu Gly Leu Ala Leu
                          1               5                  10 ctg ctc ctg ctg gcc acc gtg tcg cag tta ctg cag ccg gtc cag gga     941
Leu Leu Leu Leu Ala Thr Val Ser Gln Leu Leu Gln Pro Val Gln Gly
             15                  20                  25 cgc cga aag atg tgc ggc gag gct ctg atc cag gca ctg gat gtg att     989
Arg Arg Lys Met Cys Gly Glu Ala Leu Ile Gln Ala Leu Asp Val Ile
         30                  35                  40 tgt gtt aat gga ttt aca cgc cgt gtc agg cgg agc agt ggtaagtttg      1038
Cys Val Asn Gly Phe Thr Arg Arg Val Arg Arg Ser Ser
     45                  50                  55 ggtactatgc atattcgatt ggcttccata catctaactt cttttcgaca a gcg tct   1095
                                                            Ala Ser aag gat gct aga gtg cga gac ctt atc cgt aag cta cag cag ccg gat    1143
Lys Asp Ala Arg Val Arg Asp Leu Ile Arg Lys Leu Gln Gln Pro Asp
         60                  65                  70 gag gac att gaa cag gaa acg gaa acg gga agg tta aag cag aag cat    1191
Glu Asp Ile Glu Gln Glu Thr Glu Thr Gly Arg Leu Lys Gln Lys His
 75                  80                  85 acg gat gcg gat acg gag aag ggt gtg cca ccg gcc gtc gga agt gga    1239
Thr Asp Ala Asp Thr Glu Lys Gly Val Pro Pro Ala Val Gly Ser Gly
 90                  95                 100                 105 cga aag ttg cga cgc cat cgg cga cgc atc gcc cac gag tgt tgc aag    1287
Arg Lys Leu Arg Arg His Arg Arg Ile Ala His Glu Cys Cys Lys
            110                 115                 120 gag ggc tgc acc tac gac gat ata ctg gac tac tgc gcc tga            1329
Glu Gly Cys Thr Tyr Asp Asp Ile Leu Asp Tyr Cys Ala
            125                 130 tgaccaggat ggcaaaacaa acaaataaa aaccagaaac cagatcccaa aaaccaagta     1389
ccagatgaac acgacatggc tgagattttg tgtggcggca cggggaaaac acccgacgac     1449
cggcaggcta tttgcaattc attttcctac tacacttaac ccctaactat aaacgtaatc    1509
gtatttccaa atatttcatt gtaaaattc tagtggaggc aaataaagtt actctccaag     1569
cagcagcaga acaaaagaa gagtccattg ctttttttcta cattctacgc cctgcagcat    1629
tccagctgtg aggcatgggg aatccccttg ttattcaaac cacccgaagc cacccaaacc    1689
atcgagccac ccacaagcag ctgccattca gcacctcgag tgcggtgccc ttgttttccg    1749
agaacaataa tgaaaatat gaattttaa ttagatgacg ttctgatttt aataagcaaa     1809 acaaaggtg gagacaaaac gaactcggta atacactcag attcgaattt acagcttcct    1869
ttttatccat aattttgtt attatcgaag gagcgatatc aaaactagaa aacaacttcc    1929
aatcagtagc gggattttcc gaagataaca ctctattcaa ccgaagggtt ttgaaatgat   1989
```

-continued

```
aataattccg ttcttacagg taaaaatcta tactaatacc tgttttttg cggacggaaa      2049 aaaggctcag ttggcttatc attggcaaaa gggacttggg gaaaccataa agtatcgaag      2109
gtactgagcc aagataatga gataacagaa ggcgacttta ttgttttcca ctcaaaagca      2169
attgaataag ttggcactcg tttttaattg aatgggaatg aaataagctc taaaagtgtt      2229
gttaaaacgt aatggctttt tgttaattt aaagaattta agtagtttg aaagtatcat        2289 tattctttag gtaatttta ttacattcca aatttaataa atgactaatt cgaaaagtg        2349 tttatttaat caatgaatat atttcaagta agtttacttt tagtagcttg ccaaatgtga      2409
gtttaaatat gtatgcatag aactatatag ttaaactgct aaactttaca gttaaacttt      2469
ctgaacccac caaatggat gaacatcctc gtctgccgaa gggaactcga tgcacgtcat       2529 tttgttttc aacaatccag atccgtgcgc tactccttgg gcgagaaagt aaacaaacgc       2589
cagctgatat gcgtcagacc ccccgggctc atcatcatct caccatttca gacatcccat     2649
gccagcccga atcctcacga gaaactagac cagaccaggg cgaactacat atgtggatga     2709
tgctaactga cactacggct gactcatgct gacagtgctc agcgctgga tacagcccgc      2769 agacatccaa ctcgtatcct atccgattct gccccatata tataaccctc agtcgatggc     2829
tgggaggcaa acagttgagg ccgtgccact tggcagacac atactacaca ctccccgggg     2889
gattcacgca tccatactta aacaccactt catcactcat gggcatcgag atg agg        2945
                                                          Met Arg
                                                          135 tgt cag gac agg agg atc ctg cta cct agc cta ctc cta cta atc ctt       2993
Cys Gln Asp Arg Arg Ile Leu Leu Pro Ser Leu Leu Leu Leu Ile Leu
        140                 145                 150 atg atc ggc ggt gtc cag gcc acc atg aag ttg tgc ggc cgc aaa ctg       3041
Met Ile Gly Gly Val Gln Ala Thr Met Lys Leu Cys Gly Arg Lys Leu
    155                 160                 165 ccc gaa act ctc tcc aag ctc tgt gtg tat ggc ttc aac gca atg acc       3089
Pro Glu Thr Leu Ser Lys Leu Cys Val Tyr Gly Phe Asn Ala Met Thr
170                 175                 180 aag aga act ttg ggtaggtggg attttcttg atataaggaa tactaaagtg            3141
Lys Arg Thr Leu
185 ccatatctct ttactttcac ctaacacctg ta gac ccc gtg aac ttc aat cag       3194
                                   Asp Pro Val Asn Phe Asn Gln
                                        190                 195 atc gat ggc ttc gaa gac cgt tcc ctg ctg gaa aga ctg ttg agt gat       3242
Ile Asp Gly Phe Glu Asp Arg Ser Leu Leu Glu Arg Leu Leu Ser Asp
                200                 205                 210 agt tcg gtt cag atg ctc aag act cga cgt ctt cgg gat gga gtc ttc       3290
Ser Ser Val Gln Met Leu Lys Thr Arg Arg Leu Arg Asp Gly Val Phe
            215                 220                 225 gac gag tgt tgc ctg aag tcg tgc acc atg gat gag gtg ctg aga tat       3338
Asp Glu Cys Cys Leu Lys Ser Cys Thr Met Asp Glu Val Leu Arg Tyr
        230                 235                 240 tgt gct gcc aag ccg aga acg taa acctcgtaaa cctattaacc caatgacgac      3392
Cys Ala Ala Lys Pro Arg Thr
    245                 250 aactgcgatg attgaaatgg aatgaaagga cccgattggg gaaagcactc acgtaatcat     3452
agttgttaag tcgttatcga agcctactca attccaactt tggatttatg atatatatgc     3512
acatgtaaga gggatgtatg cgcataattt atgatctgaa atcagagaca ggcacgcgaa     3572
atgaatcgga acacgggatg ttatgcatgg tagatatgta tgattgtgcg gggccagaat     3632
acatcgcctg ggtataaatt attaaataaa ttatgtattc aaactgctgc agattggcca    3692
```

```
acttgattgg taatgaaacg ggtattacat tgattttttca ttgtcgttca ttgcagttaa   3752
ttatttattg aacagcggcc ggatttctgt ttgcaactat gttgaaaagg aagctgtgat   3812
tttttaacaa actctgttca ttgtaaagtt taaaatcatt ccaatttaat gccctcaaaa   3872
cctacgctga aatggtcagt tttaaaacga tatttattaa tattttagtt aatttactaa   3932
gattatccgt tttgcactttt taatgccttg catttggtaa tgcgtgattg ttatttaagg   3992
tctgcatgaa tttagttgat tccgtttatt ttagctttca aaatgtaata atcttctaat   4052
ttacaactac acagaacgat taaattatga gtattgctat aaaatcggcc aaccgcgact   4112
agaaatactc gacttttaag gtcaacataa aagtaagtca atgttttgat tataagattt   4172
gatcaattac ttctttacgg atgatataat catcgataaa cgaagtacga aaaaagctat   4232
gaactaaaat ttggaaattt cccacatgcg actaactttt gaattgcaat tggattgcct   4292
actgtattaa gacagaaaca agttttggaa atgaatgaat ggtttaaatt gtttcaagtt   4352
tttttaagat ttttttttgtt ttcaataaat ttagttttaa tagaaaaaaa gatatattca   4412
ttttagattt ctgaatactt gtgttatatc gcttttttatt caagtgtaat aatcaacata   4472
tatatcatat aatgataata ataaatgtaa cgtcccaaat taataataat ataaagtagc   4532
atttgcgatt gtttgccaaa gcttaaagca gaatatatat ttaatccatt tcgatcattc   4592
gtaaagagta acatgcaaca agctgtaaaa aacatcgatt gtagtatata tgcacatggt   4652
tggtttggaa ccagatccag agataatcgc gtcgaccagg tcagttgggg tcaatgattt   4712
tcgcattagg aggcctaatt tctgaccacg gagcagtact cccgcagagc cttcatatca   4772
caggactttt tgcagcacct ctccacgatt ccttgccgtt ggcgagttcg cctccggact   4832
tcagccaggg aattgagtac acccccaaga tagctcccag gaaagagggc acttcgcagc   4892
ggttccgata tcgagttatc ctcctcctcg aactcctgga caaactgcag gggattgagg   4952
gcgtccagat cgctgtcggc accggctaat aaaaatcgtg gatacaatgt agatctagca   5012
aagccagctt gaggatctgc atccttgtaa gaacttacgc atggcgcgct tgtgtggaat   5072
cacgggatta tactcctcgc acaccatact cagcacctcg ttgagctttt cactgcagag   5132
cgttccttgg gccaacttca ctgtggagct ggccagcaaa atcacggcca ccatcgagat   5192
gaaggacaaa ggcttgctca tggttatggg tttactgctt aggttgcttt acgatcaaat   5252
ggattaagtt gggtcgagcc gggtcgaaag ctaactgatg atgtttggcc caaagtaact   5312
ggcttatata ctgcctcgta agaaacttaa actgggtctg gtcgggtc ggtctctcgg     5372
ggtcggggtc tggatccaca cacatgttat cctcaaaagt caggttgtca aattgtgtta   5432
ggatgcgatg agtgcattcc ggagttggct cttctctcta acgcctggct aaactcattc   5492
aatgtcaaag ctgacttatg caaatggcta ttggaaaatt gtgggtggtt tttgggtggc   5552
tgtgtttggg agaagaaggg ctttgtgggc gttttgctgt cagccaatta aacaatttat   5612
gtataaacag ccaggccgta ctaagccctg catttatgaa taccaaataa gtccttggtc   5672
ttaaagttac ctcgccttta cagcccgttt gcctctacca tttctaccct atacttacca   5732
atccgcgcct gggcgcccgg caggccggag taggccaaca agaacccgag ccagctgatt   5792
ggagccagca gcatcctggc aacgaattac gcctccttgg tacttttcct ttgactgtct   5852
tgtctttgcc gctcacacaa attcttcttt ttgcactgtc tactttttatt cattagtcaa   5912
agttggtgct gcataaataa gtgattacga attggattac gaatgctgtt aggagaacgg   5972
gtgtacatat agtatgtatg tgggaatgcc atgttcaagt gttcgtatgt atgtatgtat   6032
```

-continued

```
gtgtatgcat gctgggtaat gaatgtgtgt gtgttggcca agtgtcctat ttcggtagac      6092
agtagatggc taactccaag tagctgcagg tcttgacgca gcactcgtcg tagacgccac      6152
cggtcaggtg tctcctgtgg cgacgcatct tgatcaggac ctcggatccg tacagattgg      6212
ttagcagtgg actaaaagag tatcctgccc cgtccagtgt ctgccacatg ctgctatcat      6272
cctgcacctc ctgctccgtg tcctcgtcgt cgtcgctgtt gcccagcaag ctttcacgtt      6332
tccttggcag cgtattaaag ccatggggac acaccacatc catggcatcg gacagtgcgg      6392
ggccgcagag tttgtggttt ccgggggggca gcaactggtg accactgcca gtcggcgtga      6452
ccattgccat tgcagcggtg agcatggctg cgatgagcag cgactggagc cgaaggccat      6512
gtactgctgc accgttgtgc tggctaaaca tcttggatat gcagtgaatg ctctgggctg      6572
caactggtat ttataccact aaatcggaag cgctagctaa tgcagttcaa tggcctcttc      6632
tgcagtctag cattgcagtg gcatagcaag ccccacgggc gtacaaactg caaatccttt      6692
gatcacccat gtttcaggta ccgttttttcc cctaaaaatg caaactctat ttctagctct      6752
actccccaat ttggatggaa aagcgatgca ctgttgtttt ggtagttggg gtattgtatt      6812
gtatttctta gcaaatatca gttgtatcat tacctatatc tatctatacc aatagtttgg      6872
aatgtatttg taagacattt ttaagatatt cagaagagtt agccttatgg gacttgctct      6932
aaagtgtgaa ttgatgcaca cagctttatc gagcatagtt ttcagtgtaa tcaccgccaa      6992
aaaatccgcc cacttcaaag cataacccgt tcgcccaacc tgttacattg ccgctaagag      7052
gctctgactg ctgtcgattg cgattacgat tacgaccaga tatctgtggg gcatgggggat      7112 aagggggtatg tgggccgatg gctgacagtg tggcagcctc attagcatgt cgtggccagg      7172
aggaaagtat gcttcgatga agctcctccg gcggcagtgt gcgaaatcgc ttcgatcacc      7232
atcatcgcca tcgccatggc cactcgattg tcgagttgca cgcacggcga tgccaacagt      7292
tggttgccag cgctgcactc gaaacactcg cttcttccca ccgaccgcaa agtgccggaa      7352
aagctagaaa aaaagcaaaa aaaaaagtgg aagaaaattc gcgatagaaa acggaaaaat      7412
cgaaacgaac aaaaaaagtc ggaataaatc aaggaaacat ggtgctcgac attaagatgt      7472
gccgatttga taatgtgccc tggggctttc gcctggtggg cggggcggac tacgattatc      7532
cgctgacggt ggttaaggtt aggcccgatt cgaaaaaaga acgaaatcta tatgctgcaa      7592
cccccacccc cccacgcatc acctcagccc attcacctgg cggatgttca tagaccagtg      7652
gaaaatattg ctcactatgc agctgatgaa tcacattgga ttaattcgat acgatacgtt      7712
cgaatcagtt ttatttgttc gattgcaata ttacgtaacg ccgcgatgcg tgtgtgtcca      7772
ttcggatttg ctgcattggc aaattagtta attaaagtaa ttcctctcgc ttttgtttat      7832
ctaatcgaca gggccataca tttcccgcta atgagccgca taatggcagc ggcaataaac      7892
ttattcaaat tttaattgtg tttcgctggc agttggtcct ttgtttgtgc ataaattgca      7952
tttggcaatt cgcatttttgt aacattgtgt tgacaattcg caaccagcaa caataacaaa      8012
aatacaatac atacaatact atagcatcgt cgtaaatccg aaacaaatgc gattttttaat      8072 tggcaaactg ctaagcgcat aaaacaaatg accgaaatgc gaggggcgct aaaaaatccc      8132
atcccttcga tacgaataaa tcaatttaag ccgcagagtc aaggaaggga ggtcataaat      8192 tgttttttgac ttttttggtta tttttttttt accgttttac ataaacaaat tatgctatgg      8252 gttatttttaa attccgatca atttataaaa tgtttgtgct ttgggatatg cataccatga      8312
aaaaatggaa gtttattgta aatgaattat taacttcaca agctggctga tagagaaaaa      8372
actgaaaaat gtccggaatg ttcttcattc caatgaactc cctaaattaa cttagctaat      8432
```

```
ttattcctta tactaatact ccgcttttaa gaattcctta ctacatgtta gagactcaaa    8492
aagcacatcc ttcgactcga gtccatatta ctttatggaa tgtgccaaca caccttcaca    8552
tattggctct gcaaacacta aacaatcctt ggtaatcttt tgaaaaacct ctgtttacac    8612
taccactctt cgtcatgctg ctcgccacat acagtctggt acatagatgt atggcccagc    8672
taagcccaaa gcctttgttc tataaatatt cgcaacctcc gacgatgtcg agtgcttttt    8732
gctctgcgaa ttcaccgctg gaaattgact ctaccataag tgaaatgcaa gagaccctg     8792 ggactgaaag gaaagaccct caacttggtt gggtgaaatg gtggagtctc caaccctcca    8852
cctgctcctt gtgccaacca ctttttttt tttgcagtat ttgcattact aagtcctctt     8912
ggcagtcggt gtcgtgactt tctggttatg aaccctgctt tctcataacg gaaacgaaaa    8972
caatcgcgtt tatttgccca cgaaagtgtt acaaaactgc ctgaattatg caatagaatt    9032
ctttgaacag agtgctaaga tatttcgcat tttgaaggcg aaacataatt catccataac    9092
tattagtttg atgaattctc acttcgtatg ctggcaattt tgaaggccga agtggcaaaa    9152 ccatttttaaa tgaattccta caatttatat gctcaatttg cgccaatttg tctgtactt    9212 attacccaca aaagccataa agcttatatt gtatttagtt gttattgttc tcgcaacatt    9272
ttcactttga tttatagttg cgaaaataaa tgttggcaaa tgcaaatttt tgaaacgata    9332
ttctcttaca cggtcatttg gtaccatttc cggaatatac atttaccaat tttccaaaaa    9392
aagagccata aattgtatta tccaattaaa acgattagtc cagtgggttt ttatttctaa    9452
aaatttaatt ttgtaattag agaaaactat tgtgaacttt ggatgaccta gaaagtttca    9512
ttagttgtac attatttttt accccgcctt taaaattgca gaacttctgt aaaaaaaagc    9572
ttttacaagc tatttaaata ttagtggtag agttgtttga acatttatct ttttggaatc    9632
agcaatattt ggttctctat ccttacaaat taatcttctc tttaagtgaa ctcataactt    9692
tgtatatatg tacgtatgta gaatcatcct tcaactcaaa catttccatc cggcgaaaca    9752
atgcaatatt tgagtggtta gacatgggta attccacttg actcgcttaa ctgaagtgtc    9812
gttaatgagc tgccacttct actcgagcac ccctcgttct gagcccccag ccccacaga    9872 tcctctgtag ccccccatc tccttgggca ttgtcttcgg ttctgttggg tttgtgcgtg     9932
attgtatgat tgtctgttcg ggggtctggg tctgctggtc tttgttttgt tgacatttgg    9992
cgcgcgtttt atttttatgc acttagcacg cgacgtcgcc gttgtcggct aatagaaatt   10052
tccccattat cgcatcgcat cccattgtat tgtatctcgg ctatctcgac tatctcggcc   10112
tcgcactcat tctatcgcca cattcccata tccgcatctg aatcgggcga tatctaggca   10172
ttcccatcta gatctaaaca tgtccatatg cttcaacgtt aggtgaccga gggcagcatt   10232
gctgacgagg ctggactgcg ggtcgaggat atcatcgtgc gcatcaatga cacggctgcc   10292
acgcccctta cccacgacga ggcccaccgc ctcattatgg gcagtggaag cgtcttctat   10352
tttggcgtct accggtgagc tttcccatcc ttctattcca taccattccg tttcgttctc   10412
ttactgctcg tggtcgtggt cctcgtcctt gtccggttcc tttactacta ctctttgtat   10472
cccatccacc gaggaccatt tatcacagct gagcgggcta acaacccaag aacgtttcct   10532
catgcccctg ctcaaggtaa tctacttgtt caagaaattc acaaaccaca aacgacctcg   10592
agagaaatgg aaaaaatatg acaaattttc gtgatttaag aataaagttc tggaaaaata   10652
aagcgctttc ttaaaaagtt gtctgggtaa aatgacattt ggttaatata tcataatagt   10712
taattttatt ataattataa actaagaaaa gttaaattca aaaacccacc tagccccatt   10772
```

-continued

```
agttttgaaa attaccctac cattttagaa gcaatttata ttatttgaat taagtttgta   10832
tttcaacttt ttcgggttat gaataattat tcttagagtg tccccgaaac cagggctcca   10892
tctcaggtat tccacgttac ggaattaatt ctaatgttca taaattctgc tcactttttg   10952
gtcacttgga tccatgtgca gggagaacga ggaggacgct tacgagtgcc taaagaagtt   11012
tcccacgagc gagggttcgt tgaccaagtc accaatgccg accatttcac cgtcgccgac   11072
tccatcgctg tcccagctga cggaaaccac aaatgcccgt actccgga             11120
```

```
<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 8
ctaggaattc gatcgagcag gatgag                                    26

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 9
cacttctaga tcatcaggcg cagtag                                    26

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 10
cttcatcact catgggcatc gag                                       23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 11
tgggttaata ggtttacgag gtt                                       23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 12
gcttccgatt tagtggtata aa                                        22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:primer
```

```
<400> SEQUENCE: 13
ttcgtatgta tgtatgtatg tg                                             22

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 14
taaacccata accatgagca agc                                            23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 15
tcagttgggg tcaatgattt tcg                                            23

<210> SEQ ID NO 16
<211> LENGTH: 134
<212> TYPE: PRT
<213> ORGANISM: Drosophila melanogaster

<400> SEQUENCE: 16
```

Met Ser Leu Ile Arg Leu Gly Leu Ala Leu Leu Leu Leu Ala Thr
1               5                   10                  15

Val Ser Gln Leu Leu Gln Pro Val Gln Gly Arg Arg Lys Met Cys Gly
            20                  25                  30

Glu Ala Leu Ile Gln Ala Leu Asp Val Ile Cys Val Asn Gly Phe Thr
        35                  40                  45

Arg Arg Val Arg Arg Ser Ser Ala Ser Lys Asp Ala Arg Val Arg Asp
    50                  55                  60

Leu Ile Arg Lys Leu Gln Gln Pro Asp Glu Asp Ile Glu Gln Glu Thr
65                  70                  75                  80

Glu Thr Gly Arg Leu Lys Gln Lys His Thr Asp Ala Asp Thr Glu Lys
                85                  90                  95

Gly Val Pro Pro Ala Val Gly Ser Gly Arg Lys Leu Arg Arg His Arg
            100                 105                 110

Arg Arg Ile Ala His Glu Cys Cys Lys Glu Gly Cys Thr Tyr Asp Asp
        115                 120                 125

Ile Leu Asp Tyr Cys Ala
    130

```
<210> SEQ ID NO 17
<211> LENGTH: 116
<212> TYPE: PRT
<213> ORGANISM: Drosophila melanogaster

<400> SEQUENCE: 17
```

Met Arg Cys Gln Asp Arg Arg Ile Leu Leu Pro Ser Leu Leu Leu Leu
1               5                   10                  15

Ile Leu Met Ile Gly Gly Val Gln Ala Thr Met Lys Leu Cys Gly Arg
            20                  25                  30

Lys Leu Pro Glu Thr Leu Ser Lys Leu Cys Val Tyr Gly Phe Asn Ala

```
                35                  40                  45
Met Thr Lys Arg Thr Leu Asp Pro Val Asn Phe Asn Gln Ile Asp Gly
             50                  55                  60

Phe Glu Asp Arg Ser Leu Leu Glu Arg Leu Leu Ser Asp Ser Ser Val
 65                  70                  75                  80

Gln Met Leu Lys Thr Arg Arg Leu Arg Asp Gly Val Phe Asp Glu Cys
                 85                  90                  95

Cys Leu Lys Ser Cys Thr Met Asp Glu Val Leu Arg Tyr Cys Ala Ala
                100                 105                 110

Lys Pro Arg Thr
            115

<210> SEQ ID NO 18
<211> LENGTH: 154
<212> TYPE: PRT
<213> ORGANISM: Drosophila melanogaster

<400> SEQUENCE: 18

Met Phe Ser Gln His Asn Gly Ala Ala Val His Gly Leu Arg Leu Gln
  1               5                  10                  15

Ser Leu Leu Ile Ala Ala Met Leu Thr Ala Ala Met Ala Met Val Thr
                 20                  25                  30

Pro Thr Gly Ser Gly His Gln Leu Leu Pro Pro Gly Asn His Lys Leu
             35                  40                  45

Cys Gly Pro Ala Leu Ser Asp Ala Met Asp Val Val Cys Pro His Gly
 50                  55                  60

Phe Asn Thr Leu Pro Arg Lys Arg Glu Ser Leu Leu Gly Asn Ser Asp
 65                  70                  75                  80

Asp Asp Glu Asp Thr Glu Gln Glu Val Gln Asp Asp Ser Ser Met Trp
                 85                  90                  95

Gln Thr Leu Asp Gly Ala Gly Tyr Ser Phe Ser Pro Leu Leu Thr Asn
                100                 105                 110

Leu Tyr Gly Ser Glu Val Leu Ile Lys Met Arg Arg His Arg Arg His
            115                 120                 125

Leu Thr Gly Gly Val Tyr Asp Glu Cys Cys Val Lys Thr Cys Ser Tyr
        130                 135                 140

Leu Glu Leu Ala Ile Tyr Cys Leu Pro Lys
145                 150

<210> SEQ ID NO 19
<211> LENGTH: 137
<212> TYPE: PRT
<213> ORGANISM: Drosophila melanogaster

<400> SEQUENCE: 19

Met Ser Lys Pro Leu Ser Phe Ile Ser Met Val Ala Val Ile Leu Leu
  1               5                  10                  15

Ala Ser Ser Thr Val Lys Leu Ala Gln Gly Thr Leu Cys Ser Glu Lys
                 20                  25                  30

Leu Asn Glu Val Leu Ser Met Val Cys Glu Glu Tyr Asn Pro Val Ile
             35                  40                  45

Pro His Lys Arg Ala Met Pro Gly Ala Asp Ser Asp Leu Asp Ala Leu
         50                  55                  60

Asn Pro Leu Gln Phe Val Gln Glu Phe Glu Glu Asp Asn Ser Ile
 65                  70                  75                  80

Ser Glu Pro Leu Arg Ser Ala Leu Phe Pro Gly Ser Tyr Leu Gly Gly
```

```
                    85                   90                    95
Val Leu Asn Ser Leu Ala Glu Val Arg Arg Thr Arg Gln Arg Gln
                100                 105                 110

Gly Ile Val Glu Arg Cys Cys Lys Lys Ser Cys Asp Met Lys Ala Leu
            115                 120                 125

Arg Glu Tyr Cys Ser Val Val Arg Asn
    130                 135

<210> SEQ ID NO 20
<211> LENGTH: 30
<212> TYPE: PRT
<213> ORGANISM: Homo sapiens

<400> SEQUENCE: 20

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 21
<211> LENGTH: 21
<212> TYPE: PRT
<213> ORGANISM: Homo sapiens

<400> SEQUENCE: 21

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 22
<211> LENGTH: 68
<212> TYPE: PRT
<213> ORGANISM: Homo sapiens
<220> FEATURE:
<221> NAME/KEY: SITE
<222> LOCATION: 30 .. 37
<223> OTHER INFORMATION: Xaa = any amino acid

<400> SEQUENCE: 22

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Xaa Xaa Xaa
            20                  25                  30

Xaa Xaa Xaa Xaa Xaa Gln Thr Gly Ile Val Asp Glu Cys Cys Phe Arg
        35                  40                  45

Ser Cys Asp Leu Arg Arg Leu Glu Met Tyr Cys Ala Pro Leu Lys Pro
    50                  55                  60

Ala Lys Ser Ala
65

<210> SEQ ID NO 23
<211> LENGTH: 28
<212> TYPE: PRT
<213> ORGANISM: Homo sapiens

<400> SEQUENCE: 23

Lys Trp Lys Asp Asp Val Ile Lys Leu Cys Gly Arg Glu Leu Val Arg
1               5                   10                  15

Ala Gln Ile Ala Ile Cys Gly Met Ser Thr Trp Ser
            20                  25
```

<210> SEQ ID NO 24
<211> LENGTH: 23
<212> TYPE: PRT
<213> ORGANISM: Homo sapiens

<400> SEQUENCE: 24

Arg Pro Tyr Val Ala Leu Phe Glu Lys Cys Cys Leu Ile Gly Leu Thr
1               5                   10                  15

Lys Arg Ser Leu Lys Tyr Cys
            20

<210> SEQ ID NO 25
<211> LENGTH: 32
<212> TYPE: PRT
<213> ORGANISM: Homo sapiens

<400> SEQUENCE: 25

Pro Ala Gln Glu Ala Pro Glu Lys Leu Cys Gly His His Phe Val Arg
1               5                   10                  15

Ala Leu Val Arg Leu Cys Gly Gly Pro Arg Trp Ser Pro Glu Asp Gly
            20                  25                  30

<210> SEQ ID NO 26
<211> LENGTH: 26
<212> TYPE: PRT
<213> ORGANISM: Homo sapiens

<400> SEQUENCE: 26

Ala Ala Ala Thr Asn Pro Ala Arg His Cys Cys Leu Ser Gly Cys Thr
1               5                   10                  15

Arg Gln Asp Leu Leu Thr Leu Cys Pro His
            20                  25

<210> SEQ ID NO 27
<211> LENGTH: 41
<212> TYPE: PRT
<213> ORGANISM: Homo sapiens

<400> SEQUENCE: 27

Gln Leu Leu Arg Glu Ser Leu Ala Ala Glu Leu Arg Gly Cys Gly Pro
1               5                   10                  15

Arg Phe Gly Lys His Leu Leu Ser Tyr Cys Pro Met Pro Glu Lys Thr
            20                  25                  30

Phe Thr Thr Thr Pro Gly Gly Trp Leu
        35                  40

<210> SEQ ID NO 28
<211> LENGTH: 25
<212> TYPE: PRT
<213> ORGANISM: Homo sapiens

<400> SEQUENCE: 28

Ser Gly Arg His Arg Phe Asp Pro Phe Cys Cys Glu Val Ile Cys Asp
1               5                   10                  15

Asp Gly Thr Ser Val Lys Leu Cys Thr
            20                  25

<210> SEQ ID NO 29
<211> LENGTH: 28
<212> TYPE: PRT
<213> ORGANISM: Silkworm

```
<400> SEQUENCE: 29

Gln Gln Pro Gln Ala Val His Thr Tyr Cys Gly Arg His Leu Ala Arg
1               5                   10                  15

Thr Leu Ala Asp Leu Cys Trp Glu Ala Gly Val Asp
                20                  25

<210> SEQ ID NO 30
<211> LENGTH: 20
<212> TYPE: PRT
<213> ORGANISM: Silkworm

<400> SEQUENCE: 30

Gly Ile Val Asp Glu Cys Cys Leu Arg Pro Cys Ser Val Asp Val Leu
1               5                   10                  15

Leu Ser Tyr Cys
                20

<210> SEQ ID NO 31
<211> LENGTH: 38
<212> TYPE: PRT
<213> ORGANISM: Freshwater Snail

<400> SEQUENCE: 31

Gln Phe Ser Ala Cys Asn Ile Asn Asp Arg Pro His Arg Arg Gly Val
1               5                   10                  15

Cys Gly Ser Ala Leu Ala Asp Leu Val Asp Phe Ala Cys Ser Ser Ser
                20                  25                  30

Asn Gln Pro Ala Met Val
        35

<210> SEQ ID NO 32
<211> LENGTH: 25
<212> TYPE: PRT
<213> ORGANISM: Freshwater Snail

<400> SEQUENCE: 32

Gln Gly Thr Thr Asn Ile Val Cys Glu Cys Cys Met Lys Pro Cys Thr
1               5                   10                  15

Leu Ser Glu Leu Arg Gln Tyr Cys Pro
                20                  25

<210> SEQ ID NO 33
<211> LENGTH: 31
<212> TYPE: PRT
<213> ORGANISM: Locust

<400> SEQUENCE: 33

Ser Gly Ala Pro Gln Pro Val Ala Arg Tyr Cys Gly Glu Lys Leu Ser
1               5                   10                  15

Asn Ala Leu Lys Leu Val Cys Arg Gly Asn Tyr Asn Thr Met Phe
                20                  25                  30

<210> SEQ ID NO 34
<211> LENGTH: 24
<212> TYPE: PRT
<213> ORGANISM: Locust

<400> SEQUENCE: 34

Thr Arg Gly Val Phe Asp Glu Cys Cys Arg Lys Thr Cys Ser Ile
1               5                   10                  15
```

Ser Glu Leu Gln Thr Tyr Cys Gly
            20

<210> SEQ ID NO 35
<211> LENGTH: 108
<212> TYPE: PRT
<213> ORGANISM: Drosophila sp.
<220> FEATURE:
<221> NAME/KEY: SITE
<222> LOCATION: 25 .. 85
<223> OTHER INFORMATION: Xaa = any amino acid

<400> SEQUENCE: 35

Arg Arg Lys Met Cys Gly Glu Ala Leu Ile Gln Ala Leu Asp Val Ile
1               5                   10                  15

Cys Val Asn Gly Phe Thr Arg Arg Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
            50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Arg Arg Arg Ile Ala His Glu Cys Cys Lys Glu
                85                  90                  95

Gly Cys Thr Tyr Asp Asp Ile Leu Asp Tyr Cys Ala
            100                 105

<210> SEQ ID NO 36
<211> LENGTH: 91
<212> TYPE: PRT
<213> ORGANISM: Drosophila sp.
<220> FEATURE:
<221> NAME/KEY: SITE
<222> LOCATION: 27 .. 60
<223> OTHER INFORMATION: Xaa = any amino acid

<400> SEQUENCE: 36

Thr Met Lys Leu Cys Gly Arg Lys Leu Pro Glu Thr Leu Ser Lys Leu
1               5                   10                  15

Cys Val Tyr Gly Phe Asn Ala Met Thr Lys Arg Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Arg Arg Leu Arg
            50                  55                  60

Asp Gly Val Phe Asp Glu Cys Cys Leu Lys Ser Cys Thr Met Asp Glu
65                  70                  75                  80

Val Leu Arg Tyr Cys Ala Ala Lys Pro Arg Thr
                85                  90

<210> SEQ ID NO 37
<211> LENGTH: 124
<212> TYPE: PRT
<213> ORGANISM: Drosophila sp.
<220> FEATURE:
<221> NAME/KEY: SITE
<222> LOCATION: 43 .. 92
<223> OTHER INFORMATION: Xaa = any amino acid

<400> SEQUENCE: 37

Met Val Thr Pro Thr Gly Ser Gly His Gln Leu Leu Pro Pro Gly Asn

```
                1               5                    10                   15
His Lys Leu Cys Gly Pro Ala Leu Ser Asp Ala Met Asp Val Val Cys
                20                   25                  30

Pro His Gly Phe Asn Thr Leu Pro Arg Lys Xaa Xaa Xaa Xaa Xaa
                35                   40                  45

Xaa Xaa Xaa Xaa Xaa Xaa Xaa Xaa Xaa Xaa Xaa Xaa Xaa Xaa Xaa
                50                   55                  60

Xaa Xaa Xaa Xaa Xaa Xaa Xaa Xaa Xaa Xaa Xaa Xaa Xaa Xaa Xaa
 65                  70                   75                  80

Xaa Xaa Xaa Xaa Xaa Xaa Xaa Xaa Xaa Xaa Arg Arg His Arg
                85                   90                  95

Arg His Leu Thr Gly Gly Val Tyr Asp Glu Cys Cys Val Lys Thr Cys
                100                  105                 110

Ser Tyr Leu Glu Leu Ala Ile Tyr Cys Leu Pro Lys
                115                  120
```

<210> SEQ ID NO 38
<211> LENGTH: 111
<212> TYPE: PRT
<213> ORGANISM: Drosophila sp.
<220> FEATURE:
<221> NAME/KEY: SITE
<222> LOCATION: 27 .. 79
<223> OTHER INFORMATION: Xaa = any amino acid

<400> SEQUENCE: 38

```
Thr Leu Cys Ser Glu Lys Leu Asn Glu Val Leu Ser Met Val Cys Glu
 1               5                   10                  15

Glu Tyr Asn Pro Val Ile Pro His Lys Arg Xaa Xaa Xaa Xaa Xaa
                20                   25                  30

Xaa Xaa Xaa Xaa Xaa Xaa Xaa Xaa Xaa Xaa Xaa Xaa Xaa Xaa Xaa
                35                   40                  45

Xaa Xaa Xaa Xaa Xaa Xaa Xaa Xaa Xaa Xaa Xaa Xaa Xaa Xaa Xaa
                50                   55                  60

Xaa Xaa Xaa Xaa Xaa Xaa Xaa Xaa Xaa Xaa Xaa Xaa Xaa Xaa Arg
 65                  70                   75                  80

Arg Thr Arg Gln Arg Gln Gly Ile Val Glu Arg Cys Cys Lys Lys Ser
                85                   90                  95

Cys Asp Met Lys Ala Leu Arg Glu Tyr Cys Ser Val Val Arg Asn
                100                  105                 110
```

<210> SEQ ID NO 39
<211> LENGTH: 111
<212> TYPE: PRT
<213> ORGANISM: Locust
<220> FEATURE:
<221> NAME/KEY: SITE
<222> LOCATION: 34 .. 85
<223> OTHER INFORMATION: Xaa = any amino acid

<400> SEQUENCE: 39

```
Ser Gly Ala Pro Gln Pro Val Ala Arg Tyr Cys Gly Glu Lys Leu Ser
 1               5                   10                  15

Asn Ala Leu Lys Leu Val Cys Arg Gly Asn Tyr Asn Thr Met Phe Lys
                20                   25                  30

Lys Xaa Xaa Xaa Xaa Xaa Xaa Xaa Xaa Xaa Xaa Xaa Xaa Xaa Xaa
                35                   40                  45

Xaa Xaa Xaa Xaa Xaa Xaa Xaa Xaa Xaa Xaa Xaa Xaa Xaa Xaa Xaa
                50                   55                  60
```

```
Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Arg Arg Thr Arg Gly Val Phe Asp Glu Cys Cys
                 85                  90                  95

Cys Arg Lys Thr Cys Ser Ile Ser Glu Leu Gln Thr Tyr Cys Gly
            100                 105                 110

<210> SEQ ID NO 40
<211> LENGTH: 73
<212> TYPE: PRT
<213> ORGANISM: Silkworm
<220> FEATURE:
<221> NAME/KEY: SITE
<222> LOCATION: 31 .. 51
<223> OTHER INFORMATION: Xaa = any amino acid

<400> SEQUENCE: 40

Gln Gln Pro Gln Ala Val His Thr Tyr Cys Gly Arg His Leu Ala Arg
  1               5                  10                  15

Thr Leu Ala Asp Leu Cys Trp Glu Ala Gly Val Asp Lys Arg Xaa Xaa
                 20                  25                  30

Xaa Xaa Xaa Xaa Xaa Xaa Xaa Xaa Xaa Xaa Xaa Xaa Xaa Xaa Xaa Xaa
                 35                  40                  45

Xaa Xaa Xaa Lys Arg Gly Ile Val Asp Glu Cys Cys Leu Arg Pro Cys
 50                  55                  60

Ser Val Asp Val Leu Leu Ser Tyr Cys
 65                  70

<210> SEQ ID NO 41
<211> LENGTH: 92
<212> TYPE: PRT
<213> ORGANISM: Freshwater Snail
<220> FEATURE:
<221> NAME/KEY: SITE
<222> LOCATION: 41 .. 65
<223> OTHER INFORMATION: Xaa = any amino acid

<400> SEQUENCE: 41

Gln Phe Ser Ala Cys Asn Ile Asn Asp Arg Pro His Arg Arg Gly Val
  1               5                  10                  15

Cys Gly Ser Ala Leu Ala Asp Leu Val Asp Phe Ala Cys Ser Ser Ser
                 20                  25                  30

Asn Gln Pro Ala Met Val Lys Arg Xaa Xaa Xaa Xaa Xaa Xaa Xaa Xaa
                 35                  40                  45

Xaa Xaa Xaa Xaa Xaa Xaa Xaa Xaa Xaa Xaa Xaa Xaa Xaa Xaa Xaa Xaa
 50                  55                  60

Xaa Lys Arg Gln Gly Thr Thr Asn Ile Val Cys Glu Cys Cys Met Lys
 65                  70                  75                  80

Pro Cys Thr Leu Ser Glu Leu Arg Gln Tyr Cys Pro
                 85                  90

<210> SEQ ID NO 42
<211> LENGTH: 79
<212> TYPE: PRT
<213> ORGANISM: Invertberate Phylum
<220> FEATURE:
<221> NAME/KEY: SITE
<222> LOCATION: 31 .. 50
<223> OTHER INFORMATION: Xaa = any amino acid

<400> SEQUENCE: 42
```

-continued

```
Ser Ile Arg Leu Cys Gly Ser Arg Leu Thr Thr Thr Leu Leu Ala Val
1               5                   10                  15

Cys Arg Asn Gln Leu Cys Thr Gly Leu Thr Ala Phe Lys Arg Xaa Xaa
            20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Lys Arg Gly Gly Ile Ala Thr Glu Cys Cys Glu Lys Arg Cys
            50                  55                  60

Ser Phe Ala Tyr Leu Lys Thr Phe Cys Cys Asn Gln Asp Asp Asn
65                  70                  75
```

<210> SEQ ID NO 43
<211> LENGTH: 86
<212> TYPE: PRT
<213> ORGANISM: Homo sapiens
<220> FEATURE:
<221> NAME/KEY: SITE
<222> LOCATION: 33 .. 64
<223> OTHER INFORMATION: Xaa = any amino acid

<400> SEQUENCE: 43

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Lys
            50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85
```

<210> SEQ ID NO 44
<211> LENGTH: 68
<212> TYPE: PRT
<213> ORGANISM: Homo sapiens

<400> SEQUENCE: 44

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Arg Arg Pro Gln Thr Gly Ile Val Asp Glu Cys Cys Phe Arg
            35                  40                  45

Ser Cys Asp Leu Arg Arg Leu Glu Met Tyr Cys Ala Pro Leu Lys Pro
            50                  55                  60

Ala Lys Ser Ala
65
```

<210> SEQ ID NO 45
<211> LENGTH: 159
<212> TYPE: PRT
<213> ORGANISM: Homo sapiens
<220> FEATURE:
<221> NAME/KEY: SITE
<222> LOCATION: 31 .. 134
<223> OTHER INFORMATION: Xaa = any amino acid

<400> SEQUENCE: 45

-continued

```
Lys Trp Lys Asp Asp Val Ile Lys Leu Cys Gly Arg Glu Leu Val Arg
1               5                   10                  15

Ala Gln Ile Ala Ile Cys Gly Met Ser Thr Trp Ser Lys Arg Xaa Xaa
            20                  25              30

Xaa Xaa Xaa Xaa Xaa Xaa Xaa Xaa Xaa Xaa Xaa Xaa Xaa Xaa Xaa Xaa
            35                  40              45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Lys Arg Arg Pro Tyr Val Ala Leu Phe Glu
    130                 135                 140

Lys Cys Cys Leu Ile Gly Leu Thr Lys Arg Ser Leu Lys Tyr Cys
145                 150                 155
```

NUCLEIC ACIDS AND PROTEINS OF D. MELANOGASTER INSULIN-LIKE GENES AND USES THEREOF

1. INTRODUCTION

The present invention relates to Drosophila insulin-like genes and methods for identifying insulin-like genes. The invention provides nucleotide sequences of Drosophila insulin-like genes, amino acid sequences of their encoded proteins (including peptide or polypeptide), and derivatives (e.g., fragments) and analogs thereof. The invention further relates to fragments (and derivatives and analogs thereof) of insulin-like proteins which comprise one or more domains of an insulin-like protein. Antibodies to an insulin-like protein, and derivatives and analogs thereof, are provided. Methods of production of an insulin-like protein (e.g., by recombinant means), and derivatives and analogs thereof, are provided. Methods to identify the biological function of a Drosophila insulin-like gene are provided, including various methods for the functional modification (e.g., overexpression, underexpression, mutation, knock-out) of one gene, or of two or more genes simultaneously. Methods to identify a Drosophila gene which modifies the function of, and/or functions in a downstream pathway from, an insulin-like gene are provided. The invention further provides for use of Drosophila insulin-like proteins as a media additive or pesticide.

2. BACKGROUND OF THE INVENTION

Citation of a reference herein shall not be construed as an admission that such reference is prior art to the present invention.

2.1. THE INSULIN SUPERFAMILY

Insulin-like proteins are a large and widely-distributed group of structurally-related peptide hormones that have pivotal roles in controlling animal growth, development, reproduction, and metabolism (Blundell and Humbel, 1980, Nature 287:781–787). Consequently, the insulin superfamily has become one of the most intensively investigated classes of peptide hormones. Such hormones have a vast array of uses including, for example, clinical applications in human disease, management of fish and livestock, and the control of agriculturally-important animal pests. At least five different subfamilies of insulin-like proteins have been identified in vertebrates, represented by insulin (Steiner et al., 1989, in *Endocrinology*, DeGroot, ed., Philadelphia, Saunders, pp. 1263–1289), insulin-like growth factor (IGF, previously termed somatomedin) (Humbel, 1990, Eur. J. Biochem. 190:445–462), relaxin (Schwabe and Bullesback, 1994, FASEB J. 8:1152–1160), relaxin-like factor (RLF, previously called Leydig cell-specific insulin-like peptide) (Adham et al., 1993, J. Biol. Chem. 268:26668–72; Ivell, 1997, Reviews of Reproduction 2:133–138), and placentin (also known as early placenta insulin-like peptide, or ELIP) (Chassin et al., 1995, Genomics 29:465–470).

Insulin superfamily members in invertebrates have been less extensively analyzed than in vertebrates, but a number of different subgroups have been defined. Such subgroups include molluscan insulin-related peptides (MIP-I to MIP-VII) (Smit et al., 1988, Nature 331:535–538; Smit et al., 1995, Neuroscience 70:589–596), the bombyxins of lepidoptera (originally referred to as prothoracicotropic hormone or PTTH) (Kondo et al., 1996, J Mol. Biol. 259:926–937), and the locust insulin-related peptide (LIRP) (Lagueux et al., 1990, Eur. J. Biochem. 187:249–254). Most recently, there have been descriptions of an exceptionally large insulin-like gene family in the nematode *C. elegans* (U.S. patent application Ser. No. 09/062,580, filed Apr. 17, 1998 (Attorney Docket No. 7326-059) entitled "NUCLEIC ACIDS AND PROTEINS OF *C. ELEGANS* INSULIN-LIKE GENES AND USES THEREOF" by Homburger et al; U.S. patent application Ser. No. 09/074,984, filed May 8, 1998 (Attorney Docket No. 7326-068) entitled "NUCLEIC ACIDS AND PROTEINS OF *C. ELEGANS* INSULIN-LIKE GENES AND USES THEREOF" by Buchman et al; U.S. patent application Ser. No. 09/084,303, filed May 26, 1998 (Attorney Docket No. 7326-069) entitled "NUCLEIC ACIDS AND PROTEINS OF *C. ELEGANS* INSULIN-LIKE GENES AND USES THEREOF" by Ferguson et al; Duret, et al., 1998, Genome Res. 8:348–353; Brousseau, et al., 1998, Early 1998 East Coast Worm Meeting, abstract 20; Kawano, et al., 1998, Worm Breeder's Gazette 15(2):47; Pierce and Ruvkun, 1998, Early 1998 East Coast Worm Meeting, abstract 150; Wisotzkey and Liu, 1998, Early 1998 East Coast Worm Meeting, abstract 206). Also, putative orthologs of both vertebrate insulin and IGF have been identified in a tunicate (McRory and Sherwood, 1997, DNA and Cell Biology 116:939–949). Tunicates are thought to be the closest living invertebrate relative to the progenitor from which vertebrates evolved (McRory and Sherwood, 1997, DNA and Cell Biology 16:939–949).

Comparison of the primary sequence of insulin superfamily peptides, cDNAs, and genes, as well as the overall conservation of functional and structural domains of insulin-like genes and proteins, lead to the conclusion that existing members of the insulin superfamily evolved from a common ancestral gene (Blundell and Humbel, 1980, Nature 287:781–787; LeRoith, et al., 1986, Recent Prog. Horm. Res. 42:549–87; Murray-Rust, et al., 1992, BioEssays 14:325–331; LeRoith, et al., 1993, Mol. Reprod. Dev. 35(4): 332–8). From the extensive sequence divergence evident among known subfamilies of insulin-like proteins, it is assumed that this is an ancient family of regulatory hormones that evolved to control growth, reproduction and metabolism in early metazoans. However, the precise evolutionary origins of this important family remain unclear.

2.1.1. COMMON STRUCTURAL THEMES

There are common structural themes that unite the insulin superfamily of proteins. Insulin-like peptide hormones are synthesized in vivo as precursor proteins having structures that are variations of the structure schematically represented in FIG. 1. Most precursor forms of the insulin superfamily can be divided into four domains, termed Pre, B, C, and A domains, extending in order from the N-terminus to the C-terminus of a precursor polypeptide (see FIG. 1). Precursors of the IGF subfamily are distinguished by having two additional domains at the C-terminal end, termed D and E domains. The precursors of the locust LIRP protein and some *C. elegans* insulin-like proteins are distinctive in that they possess another domain, here designated as the F domain, positioned between the Pre domain and the B peptide. The N-terminal Pre domain typically contains a hydrophobic signal sequence which directs secretion of the hormone from cells and is removed by the enzymatic action of a signal peptidase during transit into the endoplasmic reticulum (see the asterisk in FIG. 1). Upon folding, the prohormone undergoes additional processing which, in most cases, involves proteolytic cleavage at two sites that excise the C peptide from the mature hormone (see the two middle arrows illustrated in FIG. 1). These processing steps are mediated by prohormone convertases that cleave at specific positions next to basic residues in the C peptide sequence.

As a result, most forms of mature insulin superfamily hormones consist of two polypeptide chains, the A and B peptides, which are covalently joined by disulfide linkages (S—S) between Cys residues (see S—S linkages illustrated in FIG. 1). The precise arrangement of Cys residues and disulfide linkages, both between the A and B peptides and within the A peptide, is highly characteristic of the insulin superfamily of hormones. The vast majority of known insulin superfamily members contain six precisely-positioned Cys residues, two in the B chain and four in the A chain, which participate in the formation of three disulfide bonds. Two of these disulfide linkages covalently join the B and A chains (i.e., they form inter-chain bonds), whereas the third disulfide linkage occurs within the A peptide (i.e., as an intra-chain bond) and appears to stabilize a bend in the A chain fold.

The IGF subfamily of hormones has a unique processing pathway. In this subfamily, the connecting C peptide is not removed by processing of the prohormone. Instead, a single proteolytic cleavage event removes the C-terminal E domain (see the right-hand arrow illustrated in FIG. 1). Consequently, mature hormones of the IGF subfamily contain a single polypeptide chain with contiguous B, C, A, and D domains. Despite this difference in proteolytic processing, the disulfide bonding pattern between Cys residues in the IGF subfamily is identical to that of other superfamily members.

In summary, FIG. 1 illustrates the structural organization of precursor forms of the insulin superfamily of hormones. The different domains that make up precursor forms of insulin-like hormones are represented as boxes labeled Pre, F, B, C, A, D, and E, extending from the N-terminus (left) to the C-terminus (right) of the nascent polypeptide chain, respectively. Domains that may remain in a mature hormone are represented as unshaded boxes (the B, A, and D peptide domains) or as lightly hatched (the C or "connecting" peptide domain). By contrast, domains that are removed during proteolytic processing are represented as shaded (the Pre peptide domain and F domain) or as hatched (the E peptide domain). IGF hormones are unique in having D and E peptide domains; these domains are represented as smaller boxes in FIG. 1. Some *C. elegans* insulin-like proteins are thus far unique in apparently lacking any C peptide sequences and may be produced as a single polypeptide chain consisting of contiguous B and A domains (U.S. patent application Ser. No. 09/062,580, filed Apr. 17, 1998 (Attorney Docket No. 7326-059) entitled "NUCLEIC ACIDS AND PROTEINS OF *C. ELEGANS* INSULIN-LIKE GENES AND USES THEREOF" by Homburger et al; U.S. patent application Ser. No. 09/074,984, filed May 8, 1998 (Attorney Docket No. 7326-068) entitled "NUCLEIC ACIDS AND PROTEINS OF *C. ELEGANS* INSULIN-LIKE GENES AND USES THEREOF" by Buchman et al; U.S. patent application Ser. No. 09/084,303, filed May 26, 1998 (Attorney Docket No. 7326-069) entitled "NUCLEIC ACIDS AND PROTEINS OF *C. ELEGANS* INSULIN-LIKE GENES AND USES THEREOF" by Ferguson et al.; Brousseau, et al., 1998, Early 1998 East Coast Worm Meeting, abstract 20; Duret, et al., 1998, Genome Res. 8(4):348–53; Kawano, et al., 1998, Worm Breeder's Gazette 15(2):47; Wisotzkey and Liu, 1998, Early 1998 East Coast Worm Meeting, abstract 206). Cleavage sites utilized by proteases during proteolytic processing (i.e., protein maturation) are indicated below the boxes. The asterisk marks the position of cleavage by signal peptidase. Arrows indicate cleavage sites by prohormone convertases. Disulfide bonds (S—S) are represented above the boxes with lines indicating connections between covalently-bonded Cys residues.

Since the A and B peptide domains constitute common structural segments among all mature insulin superfamily hormones, it is not surprising that these domains are the most highly conserved at the primary sequence level. Even among closely-related members of this superfamily, the domains removed by proteolytic processing (i.e., Pre, C, and E domains) can differ extensively in amino acid sequence composition (McRory and Sherwood, 1997, DNA and Cell Biology 16:939–949; Murray-Rust et al., 1992, BioEssays 14:325–331), in marked contrast to the A and B peptides. Much of the amino acid sequence conservation within the A and B peptide domains reflects residues that play key roles in forming the secondary and tertiary structural elements that are characteristic of the insulin superfamily fold. Aligned sequences of A and B peptide domains from diverse insulin superfamily members are depicted in FIG. 2. This alignment serves to highlight the arrangement of conserved amino acid positions and their relationship to the overall folding pattern of the protein. The three dimensional structures of a number of different insulin superfamily proteins have been determined. Such superfamily proteins include insulin (Hua et al., 1991, Nature 354:238–241), relaxin (Eigenbrot et al., 1991, J. Mol. Biol. 221:15–21), IGF (Cooke et al., 1991, Biochemistry 30:5484–5491), and bombyxin (Nagata et al., 1995, J. Mol. Biol. 253:749–758). The detailed geometry of amino acid side chains in these structures, as well as common secondary and tertiary structural themes, have provided valuable clues about the forces that promote the formation of the characteristic insulin fold. Common features of the main chain fold of insulin-like structures consist of the following: (1) two helices within the A chain joined by a loop; (2) an extended, N-terminal coil within the B chain followed by a tight turn and a central helix; (3) a hydrophobic cluster or "core" that forms an interface between juxtaposed surfaces of the A and B chains; and (4) three disulfide bonds. The common helical regions found in the A and B chains are illustrated in FIG. 2 above the alignment (see "< - - - >" symbols in FIG. 2).

Beyond the above-described general features of insulin-like structures, there are an number of specific features that are unique to the various subfamilies of insulin-like proteins. Notably, in insulin and IGFs, the main chain following the B peptide central helix forms a tight turn and an extended beta-strand. By contrast, the B chain in both relaxin and bombyxin adopts a fold comprising an extended central helix followed by a coil.

2.1.2. NUMBER AND SPACING OF CYS RESIDUES

The stereotypical arrangement of Cys residues which participate in disulfide linkages within the A and B chains was noted above. It is striking that the exact number and spacing of Cys residues is nearly invariant among insulin-like proteins (see positions B7, B19, A6, A7, A11, and A20, with respect to the human insulin sequence in FIG. 2). Among over 170 sequenced members of the insulin superfamily, only a small minority show deviations from the canonical arrangement of Cys residues. Further, when differences in the arrangement do occur, they tend to be relatively minor. For example, in the case of murine relaxin, the last two Cys residues of the A chain are separated by a spacer of 9 amino acids instead of the canonical 8 amino acids (Evans et al., 1993, J. Mol. Endocrinol. 10:15–23). Another interesting variation occurs in the molluscan insulin-like proteins (MIP-I to -VII). MIP-I appears to have two extra Cys residues, one located N-terminal to the conserved Cys residues within the A chain and the other located N-terminal to the conserved Cys residues of the B chain (see FIG. 2) (Smit et al., 1988, Nature 331:535–538).

It has been proposed that this extra pair of Cys residues within MIP-I forms an additional disulfide bond between the A and B chains, thus providing further stability to the folded structure of MIP-I (Smit, et al., 1988, Nature 331:535–538). The most striking examples of variations in Cys positioning within this superfamily come from the insulin-like proteins in the nematode *C. elegans* (U.S. patent application Ser. No. 09/062,580, filed Apr. 17, 1998 (Attorney Docket No. 7326-059) entitled "NUCLEIC ACIDS AND PROTEINS OF *C. ELEGANS* INSULIN-LIKE GENES AND USES THEREOF" by Homburger et al; U.S. patent application Ser. No. 09/074,984, filed May 8, 1998 (Attorney Docket No. 7326-068) entitled "NUCLEIC ACIDS AND PROTEINS OF *C. ELEGANS* INSULIN-LIKE GENES AND USES THEREOF" by Buchman et al; U.S. patent application Ser. No. 09/084,303, filed May 26, 1998 (Attorney Docket No. 7326-069) entitled "NUCLEIC ACIDS AND PROTEINS OF *C. ELEGANS* INSULIN-LIKE GENES AND USES THEREOF" by Ferguson et al.; Brousseau, et al., 1998, Early 1998 East Coast Worm Meeting, abstract 20; Duret, et al., 1998, Genome Res. 8(4):348–53; Kawano, et al., 1998, Worm Breeder's Gazette 15(2):47; Pierce and Ruvkun, 1998, Early 1998 East Coast Worm Meeting, abstract 150; Wisotzkey and Liu, 1998, Early 1998 East Coast Worm Meeting, abstract 206). This organism appears to produce over 30 different insulin-like proteins, many of which have unusual Cys arrangements. Such unusual arrangements include the presence of an extra pair of Cys residues, the absence of a conserved pair of Cys residues, and/or altered spacing between Cys residues in either the A or B chain regions. The characteristic insulin core that makes up the interface between the A and B chains is composed of a set of side chains whose conserved hydrophobic nature helps stabilize a tight association. The side chains that participate in the core structure correspond to positions A2, A16, A19, B6, B11, B15, and B18 (see FIG. 2). In addition, the A6–A11 and B19–A20 disulfide bonds are enveloped within the core structure. One other highly-conserved residue within the insulin superfamily is that at B8, which is almost always Gly. The unique flexibility of Gly in this position allows the formation of a tight turn between the extended N-terminus of the B chain and the central helix that immediately follows. Gly residues appear to play a similar role in other positions that promote unique structural features of different insulin subfamily folding patterns. For instance, the Gly at position B in insulin and IGF appears important in allowing the formation of a tight turn between the central helix and the following beta-strand of the B chain, a hallmark of this subfamily of structures (Blundell et al., 1972, Adv. Protein Chem. 26:279–402). Similarly, a Gly at position A10 in relaxins has been shown to be important for the formation of an exceptionally tight turn between the two A chain helices within the folding pattern of this subfamily (Schwabe and Bullesback, 1994, FASEB J. 8:1152–1160).

2.1.3. RECEPTOR-LIGAND RECOGNITION

An intriguing feature of this diverse family of peptide hormones is the nature of receptor-ligand recognition and the structural basis of its specificity. Although no structures have yet been solved for insulin superfamily receptor-ligand complexes, the issue has been explored through mutational analysis and structure-activity studies of a number of insulin superfamily hormones. The collected results of studies of insulin, relaxin and bombyxin have led to the hypothesis that a common surface is employed by these hormones for receptor-ligand interaction, composed of the central portion of the B chain and the A chain N- and C-termini (Hua, et al., 1991, Nature 354:238–241; Blundell, et al., 1972, Advan. Protein Chem. 26:279–402; Murray-Rust et al., 1992, BioEssays 14:325–331; Nagata et al., 1995, J. Mol. Biol. 253:759–770; Bullesbach et al., 1996, Biochemistry 35:9754–9760; Kristensen et al., 1997, J. Biol. Chem. 272:12978–12983; Schaffer, 1994, Eur. J. Biochem. 221:1127–1132). It appears that insulin and relaxin utilize other structural features for receptor recognition beyond these common elements, specifically, the C-terminus of the B chain in insulin and IGF, and the extended A chain N-terminal helix in relaxin (Nagata et al., 1995, J. Mol. Biol. 253:749–758; Bullesbach et al., 1996, Biochemistry 35:9754–9760; Kristensen et al., 1997, Methods in Cell Biology 44:143–159). Clearly, it is the precise nature of specific amino acid side chains within the receptor recognition surface that contribute to the affinity and specificity of receptor binding. In this regard, a comparison of the residues implicated in receptor recognition for insulin versus relaxin is informative since these two hormones associate with distinct receptor molecules with no evidence for cross-recognition (Rawitch et al., 1980, Int. J. Biochem. 11:357–362).

Residues implicated in insulin receptor recognition include GlyA1, IleA2, ValA3, LeuA13, TyrA19 and AsnA21 on the A chain and ValB12, TyrB16, LeuB17, PheB24, PheB25, and TyrB26 on the B chain (see FIG. 2). A striking feature of this constellation of side chains is that they are largely hydrophobic in character, particularly through the B chain central helix and beta-strand. It is significant that, within the IGF-I sequence, most of the same positions are occupied by either identical or closely-related amino acids to those found in insulin (see FIG. 2). This is consistent with the observation that, although insulin and IGF-I preferentially associate with distinct receptor molecules, there is still measurable cross-recognition by the receptors. Such cross-recognition is believed to be of physiological significance in vivo, perhaps permitting crosstalk between signals controlling growth and metabolism (Humbel, 1990, European Journal of Biochemistry 190:445–462).

In relaxin, by marked contrast, two hydrophilic basic residues have been shown to be critical for receptor recognition. These relaxin residues, ArgB9 and ArgB13 (see FIG. 2), protrude one turn apart from the central B helix (Eigenbrot et al., 1991, J. Mol. Biol. 221:15–21). Not surprisingly, this pair of Arg residues at positions B9 and B13 are rather distinctive for the relaxin subfamily hormones within vertebrates. Other residues implicated in human relaxin II-receptor recognition include TyrA(-1), PheA19, ValB12, GinB15 and IleB16 (Bullesbach and Schwabe, 1988, Int. J. Peptide Protein Res. 32:361–367).

In summary, FIG. 2 illustrates conserved structural features of known insulin superfamily members. The aligned sequences of the B and A chain peptide domains are shown for representative insulin superfamily hormones from the following vertebrates and invertebrates: human insulin (Bell et al., 1979, Nature 29:525–527), human IGF-I (Jansen et al., 1983, Nature 306:609–611), human relaxin 1 (Hudson et al., 1983, Nature 301:628–631), RLF from human (Adham al., 1993, J. Biol. Chem. 268:26668–26672), placentin from human (Chassin et al., 1995, Genomics 29:465–470), bombyxin II from silkworm (Nagasawa et al., 1986, Proc. Natl. Acad. Sci. U.S.A. 83:5840–5843), MIP from freshwater snail (Smit et al., 1988, Nature 331:535–538), and LIRP from locust (Lagaeux et al., 1990, Eur. J. Biochem. 187:249–254). The numbering scheme shown at the bottom of the figure is for residues of the A and B chains relative to residue numbers for human insulin peptide domains. The nearly invariant positions of the six Cys residues that participate in disulfide bonds are boxed. MIP-I is unusual in having two extra Cys residues which are also individually boxed in that sequence. Other conserved amino acid positions that play important roles in promoting the common insulin superfamily fold are highlighted by shading of the following residue positions: B6, B8, B11, B15, B18, A2, A16, and A19. Three helical regions that comprise the common insulin fold are marked above the alignments using a "< - - - >" symbol.

2.2. HUMAN INSULIN-LIKE PROTEINS AND THERAPEUTIC APPLICATIONS

As noted above, five different subfamilies of insulin-like hormones are now recognized in humans: insulin, IGF, relaxin, RLF, and placentin. Two of these subfamilies (i.e., RLF and placentin) have been discovered relatively recently and their actual biological roles and corresponding clinical applications remain to be determined. The other three subfamilies (i.e., insulin, IGF, and relaxin) have been studied much more extensively and their roles in regulating growth, differentiation, and metabolism has yielded clinical applications of profound and well-known importance, as described briefly below.

2.2.1. INSULIN

Insulin is the central hormone governing metabolism in vertebrates (reviewed in Steiner et al., 1989, In *Endocrinology*, DeGroot, eds. Philadelphia, Saunders: 1263–1289). In humans, insulin is secreted by the beta cells of the pancreas in response to elevated blood glucose levels which normally occur following a meal. The immediate effect of insulin secretion is to induce the uptake of glucose by muscle, adipose tissue, and the liver. A longer term effect of insulin is to increase the activity of enzymes that synthesize glycogen in the liver and triglycerides in adipose tissue. Insulin can exert other actions beyond these "classic" metabolic activities, including increasing potassium transport in muscle, promoting cellular differentiation of adipocytes, increasing renal retention of sodium, and promoting production of androgens by the ovary. Defects in the secretion and/or response to insulin are responsible for the disease diabetes mellitus, which is of enormous economic significance. Within the United States, diabetes mellitus is the fourth most common reason for physician visits by patients; it is the leading cause of end-stage renal disease, non-traumatic limb amputations, and blindness in individuals of working age (Warram et al., 1995, In *Joslin's Diabetes Mellitus*, Kahn and Weir, eds., Philadelphia, Lea & Febiger, pp. 201–215; Kahn et al., 1996, Annu. Rev. Med. 47:509–531; Kahn, 1998, Cell 92:593–596). Two basic forms of diabetes mellitus occur in humans: type I or insulin-dependent diabetes, and type II or non-insulin-dependent diabetes. A critical problem in managing diabetic patients comes from the phenomenon of insulin resistance, as well as the compounding long term effects of abnormal insulin levels in these individuals. Beyond its role in diabetes mellitus, the phenomenon of insulin resistance has been linked to other pathogenic disorders including obesity, ovarian hyperandrogenism, and hypertension.

The physiologic effects of insulin are mediated by specific association of the peptide hormone with a cell surface receptor, the insulin receptor (IR), with concomitant activation of a signal transduction pathway in responding tissues. The IR has been well-characterized at the molecular level; it is a member of a large family of tyrosine kinase receptors (Ullrich et al., 1985, Nature 313:756–761). IR signaling has been shown to involve a number of intracellular participants (White and Kahn, 1994, J. Biol. Chem. 269: 1-4; Kahn et al., 1998, Cell 92:593–596). These participants include the so-called insulin receptor substrate, or IRS-1, which is phosphorylated by an activated insulin receptor kinase. IRS-1 in turn associates with phosphatidyl-inositol-3-kinase (PI3K). A number of other protein kinases and signaling proteins have been implicated in this signal transduction mechanism and presumably participate in a "kinase cascade" that leads to the modification and regulation of a host of intracellular enzymes, structural proteins, and transcription factors. Nonetheless, the precise choreography of events involved in insulin signaling remains vague, and a deeper understanding of such events is likely to have application in surmounting the major clinical problem of insulin resistance. In summary, while clinical issues associated with abnormal insulin levels have raised interest in factors regulating the synthesis, secretion and turnover of insulin, many of the underlying regulatory mechanisms remain to be clarified.

2.2.2. IGF

Humans express two forms of the IGF subfamily of insulin-like hormones, termed IGF-I and IGF-II (Humbel, 1990, Eur. J. Biochem. 190:445–462). These proteins have been found to exert powerful mitogenic effects on a variety of cells and tissues, reflecting their normal physiologic role of promoting growth in developing animals. IGF-I is apparently the primary mediator of growth hormone signaling and, as such, is a major mediator of growth of the skeletal system following birth. IGF-II may have a significant role in fetal growth. Detailed studies with IGF-I, in particular, have led to a variety of significant clinical applications in humans which relate to its growth-promoting and mitogenic properties, including treatment of injuries to the central nervous system, peripheral neuropathy, disorders of the gut, osteoporosis, and congestive heart failure, as well as the acceleration of wound-healing (Gluckman and Nikolics, 1988, "IGF-1 to improve neural outcome", U.S. Pat. No. 5,714,460; Ballard and Read, 1997, "Method for treating intestinal diseases", U.S. Pat. No. 5,679,771; Clark et al., 1997, Treatment of congestive heart failure", U.S. Pat. No. 5,661,122; Lewis et al., 1997, "Prevention and treatment of peripheral neuropathy", U.S. Pat. Nos. 5,420,112, 5,633,228 and 5,648,335; Burk, 1997, "Composition and method for the treatment of osteoporosis in mammals", U.S. Pat. No. 5,646,116; Antoniades and Lynch, 1993, "Wound healing using IGF-II and TGF", U.S. Pat. No. 5,256,644). Since administration of IGF-I has been shown to increase the growth and size of animals, there are possible applications of this hormone in animal husbandry (Humbel, 1990, Eur. J. Biochem. 190:445–462). As mentioned above, IGFs can elicit insulin-like effects in muscle and adipose tissue, and there is evidence that IGF-I administration may be useful when administered together with insulin in the treatment of diabetes (MacCuish, 1997, "Treatment of insulin-resistant diabetes", U.S. Pat. No. 5,674,845).

2.2.3. RELAXIN

The peptide hormone relaxin was first identified as an active substance in extracts of corpora lutea that induced the separation and relaxation of the pubic symphysis in guinea pigs (Schwabe and Bullesback, 1994, FASEB J. 8:1152–1160). Thus, it was originally believed that the primary physiologic role of relaxin was one associated with promoting parturition during pregnancy. Subsequent studies have confirmed this role in pregnancy for rodents and ruminants. However, the importance of relaxin to the physiology of normal pregnancy in humans is still somewhat unclear (Bani, 1997, Gen. Pharmacol. 28:13–22). Recent studies of relaxin have revealed a more complicated and interesting picture of the spectrum of activities of this peptide hormone. Specifically, relaxin has been found to control growth and differentiation of breast cancer cells in vitro, promote blood vessel dilation, have a chronotropic action on the heart, inhibit histamine release by mast cells, affect pituitary hormone secretion, and regulate fluid balance.

Given this array of physiologic effects, it is not surprising that a number of clinical applications of relaxin have been pursued. These therapeutic applications of relaxin in humans have included the treatment of intractable pain caused by the swelling or dislocation of tissues, as well as the treatment of congestive heart failure, bradycardia, and neurodegenerative diseases (Cronin et al., 1992, "Use of relaxin in cardiovascular therapy", U.S. Pat. No. 5,166,191; Cronin et al., 1995, "Use of relaxin in the treatment of bradycardia", U.S. Pat. No. 5,478,807; Yue, 1998, "Method of treating fibromyalgia with relaxin", U.S. Pat. No. 5,707,642). Two forms of relaxin, which are encoded by separate genes, have been identified in humans (Hudson et al., 1983, EMBO J. 3:2333–2339). In contrast to insulin and the IGFs, the specific receptor protein(s) for the relaxins have yet to be characterized at either the DNA or protein sequence level.

2.3. INVERTEBRATE INSULIN-LIKE PROTEINS

Studies of insulin-like molecules in invertebrates have been motivated by the desire to identify proteins which play analogous roles to the well-characterized activities of insulin and IGF in mammals. The first invertebrate insulin-like proteins to be discovered and characterized at the molecular level were the bombyxins of lepidoptera, and they remain the best characterized (Nagasawa et al., 1986, Proc. Natl. Acad. Sci. U.S.A. 83:5840–5843). Bombyxin, as the name implies, was first identified in extracts of adult heads of the silkworm Bombyx mori. Curiously, it was found that bombyxin stimulated prothoracic glands of the heterologous moth Samia cynthia ricini to synthesize and secrete ecdysteroid hormone. However, no prothoracicotropic activity was observed when bombyxin was injected into Bombyx mori, raising questions about its normal function in this organism (Kiriishi et al., 1992, Zool. Sci. 9:149–155). Bombyxin is produced by neurosecretory cells within the brain of the silkworm and released into the hemolymph. Recent studies with synthetic bombyxin have suggested a role in regulating carbohydrate metabolism with some similarities to the function of insulin in mammals. When injected into neck-ligated larvae, bombyxin reduced the concentration of the major hemolymph sugar, trehalose, and caused elevated activity of trehalase in the midgut and muscle (Satake et al., 1997, Comp. Biochem. Physiol. 188B:349–357). Additional studies have revealed a remarkable array of bombyxin genes. Over 30 separate bombyxin genes have now been identified in the haploid genome of the silkworm (Kondo et al., 1996, J. Mol. Biol. 259:926–937). The bombyxin genes are organized in clusters, and sequence comparisons have led to the categorization of six different gene subtypes. Thus far, all of the bombyxin genes appear to be specifically expressed within four pairs of medial neurosecretory cells in the brain of the silkworm.

DNA-based approaches have been used to isolate insulin-like genes from other invertebrate species, including the LIRP gene from the locust and the MIP-I through MIP-VII series of genes from the freshwater snail (Smit et al., 1998, Prog. Neurobiol. 54:35–54). The biological function of these other invertebrate superfamily members remains largely uncharacterized.

One common theme is that the major site of expression of locust and snail invertebrate insulin-like hormones is in the central nervous system, particularly neurosecretory cells, as has also been observed for the bombyxins of lepidoptera. In the freshwater snail, the cerebral light-green cells, which are the main cells that express the MIP proteins, have been associated with endocrine functions that control glycogen metabolism and the regulation of growth of soft body parts and the shell (Smit et al., 1988, Nature 331:535–538).

2.4. INSULIN SIGNALING IN INVERTEBRATE GENETIC MODEL ORGANISMS

Important issues raised in the preceding discussion regarding the biological function, regulation, and signaling mechanisms of insulin superfamily hormones could best be addressed if these pathways could be analyzed using model genetic organisms. In particular, the facile genetic tools currently available in two model organisms, the fruit fly Drosophila melanogaster and the nematode Caenorhabditis elegans, have proven to be of enormous utility in defining the biological function of genes through mutational analysis, as well as for identifying the components of biochemical pathways conserved during evolution with large-scale, systematic genetic screens (Scangos, 1997, Nature Biotechnol. 15:1220–1221; Miklos and Rubin, 1996, Cell 86:521–529). Key discoveries regarding constituents of a number of important human disease pathways, such as the Ras pathway and the pathway controlling programmed cell death, first came from genetic analysis of pathways known to have an evolutionary relation in Drosophila and C. elegans, and later shown to have direct relevance to human biology (Yuan et al., 1993, Cell 75:641–652; Therrien et al., 1995, Cell 83:879–888; Karim et al., 1996, Genetics 143:315–329; Komfeld et al., 1995, Cell 83:903–913; Rubin et al., 1997, "Protein kinase required for Ras signal transduction", U.S. Pat. No. 5,700,675; Steller et al., 1997, "Cell death genes of Drosophila melanogaster and vertebrate homologs", U.S. Pat. No. 5,593,879).

2.4.1. THE DAUER STAGE OF C. ELEGANS AND INSULIN SIGNALING

Recent discoveries from studies of C. elegans have led to the identification of components involved in a presumptive insulin signaling pathway. Intriguingly, in C. elegans there are clear connections of this pathway to important aspects of metabolic regulation. This realization has emerged from genetic dissection of the process of dauer larvae formation in the nematode (reviewed in Riddle and Albert, 1997, "Genetic and environmental regulation of dauer larva development", In C. elegans II, Riddle et al., eds., Cold Spring Harbor Press, Plainview, N.Y., pp. 739–768), as described further below.

The dauer stage is an alternative developmental stage that is induced when environmental factors are not adequate to promote successful reproduction in C. elegans. There are a number of behavioral, morphologic and metabolic changes that characterize the dauer stage which promote survival of the organism under unfavorable conditions. For example, dauer larvae remain relatively motionless, stop feeding, remain small in size and are reproductively immature. Further, there is increased deposition of fat, a reduction of TCA cycle flux, increased phosphofructokinase activity and increased flux through the glyoxylate cycle in dauer larvae, indicating increased reliance on glycogen and lipid stores as energy reserves in the dauer state (O'Riordan and Burnell, 1989, Comp. Biochem. Physiol. 92B:233–238; O'Riordan and Burnell, 1990, Comp. Biochem. Physiol. 95B:125–130; Wadsworth and Riddle, 1989, Devel. Biol. 132:167–173). Dauer larvae are relatively resistant to detergent, high temperature and oxygen deprivation as compared to normal adults. Remarkably, dauer larvae can live more than four times as long as the normal life span of C. elegans.

The main environmental cues that control entry into the dauer state are pheromone, food, and temperature. High levels of pheromone (indicative of high population density), low levels of food, and high temperature all favor entry into the dauer stage; reversal of these conditions can induce exit from the dauer stage with resumption of normal organismal development. Clearly, the decision to enter either the dauer pathway or pursue normal development is a major milestone in the life cycle of C. elegans. As such, it likely involves a complex and precise integration of many different physiologic signals. Laser microsurgery has been used to investigate the role of specific cells and tissues in regulating entry into the dauer state (Bargmann and Horvitz, 1991, Science 251:1243–1246).

These cell-killing experiments point to a prominent role for amphid neurons which comprise a pair of chemosensory organs on either side of the head. Killing of specific neurons in the amphid causes a dauer constitutive phenotype, implying that the amphids are responsible for producing a dauer-inhibiting neuronal signal during normal development.

The connection between dauer formation in the nematode and insulin signaling has come from the molecular characterization of the daf-2 gene of C. elegans (Kimura et al., 1997, Science 277:942–946). A daf-2 mutant animal exhibits a dauer constitutive phenotype, and molecular cloning of this gene has revealed that it is a nematode homolog of vertebrate insulin receptors. The physiologic analogy with insulin signaling in vertebrates is that activation of the daf-2 receptor in the nematode corresponds to a "fed" state, with the activated daf-2 receptor generating a dauer-inhibiting signal that promotes normal development. Conversely, lack of daf-2 receptor activity corresponds to a "starved" state, with the lack of inhibitory signal in this pathway favoring entry into the dauer stage. Indeed, studies of other components in the daf-2 signaling pathway have revealed further similarities with insulin signaling in humans. Four other genes, age-1, daf-16, akt-A, and akt-B, have been placed in the same pathway as daf-2 based on analysis of genetic interactions (Morris et al., 1996, Nature 382:536–539; Ogg et al., 1997, Nature 389:994–999; Lin et al., 1997, Science 278:1319–1322). The age-1 gene encodes a nematode homolog of PI3K, and the action of age-1 is required for the propagation of a daf-2 signal, in keeping with the role of PI3K in insulin signaling. Conversely, genetic analysis has shown that the normal role of daf-16 is one of blocking a signal generated by activated daf-2, and daf-i6 has been found to encode a homolog of the HNF-3/forkhead family of transcription factors. In this respect, it is relevant that, in humans, there is the suggestion that insulin mediates some of its effects in target cells by blocking the action of HNF-3 (O'Brien et al., 1995, Mol. Cell. Biol. 15:1747–1758). The akt-A and akt-B genes are thought to provide partially redundant functions within the daf-2 pathway based on preliminary results, and these proteins exhibit homology to protein kinases linked to insulin signaling in vertebrates (Paradis, 1998, Early 1998 East Coast Worm Meeting, abstract 143).

There have been several recent reports describing the identification of insulin-like genes in C. elegans (U.S. patent application Ser. No. 09/062,580, filed Apr. 17, 1998 (Attorney Docket No. 7326-059) entitled "NUCLEIC ACIDS AND PROTEINS OF C. ELEGANS INSULIN-LIKE GENES AND USES THEREOF" by Homburger et al.; U.S. patent application Ser. No. 09/074,984, filed May 8, 1998 (Attorney Docket No. 7326-068) entitled "NUCLEIC ACIDS AND PROTEINS OF C. ELEGANS INSULIN-LIKE GENES AND USES THEREOF" by Buchman et al.; U.S. patent application Ser. No. 09/084,303, filed May 26, 1998 (Attorney Docket No. 7326-069) entitled "NUCLEIC ACIDS AND PROTEINS OF C. ELEGANS INSULIN-LIKE GENES AND USES THEREOF" by Ferguson et al.; Brousseau, et al., 1998, Early 1998 East Coast Worm Meeting, abstract 20; Duret, et al., 1998, Genome Res. 8(4):348–53; Kawano, et al., 1998, Worm Breeder's Gazette 15(2):47; Pierce and Ruvkun, 1998, Early 1998 East Coast Worm Meeting, abstract 150; Wisotzkey and Liu, 1998, Early 1998 East Coast Worm Meeting, abstract 206). These results are striking because of the size and diversity of this subfamily of genes; there are at least 33 insulin-like genes in the C. elegans haploid genome, and many encode proteins with significant and novel deviations from the canonical structure of the insulin superfamily. Specifically, only one known C. elegans insulin-like gene encodes a protein with a clear, excisable C peptide. Further, most of the C. elegans insulin-like proteins have deviations in Cys number or spacing from that found in vertebrate insulin superfamily proteins. At present, it is not certain which of the C. elegans insulin-like proteins are the actual ligand(s) for the daf-2 receptor.

There is another intriguing aspect to the phenotype of nematodes defective in components of the daf-2 pathway with respect to effects on the life-span of the organism (normally about 14 days). Mutations in daf-2 and age-1 can more than double the life-span of animals, even under conditions that do not induce the formation of dauer larvae, and the extension of life-span caused by daf-2 or age-i mutations requires the activity of the daf-16 gene (Lin et al., 1997, Science 278:1319–1322; Tissenbaum and Ruvkun, 1998, Genetics 148:703–717; Larsen et al., 1995, Genetics 139:1567–1583). These findings raise the interesting possibility that detailed genetic analysis of the insulin signaling pathway could reveal new therapeutic approaches with application to aging and longevity in humans.

2.4.2. INSULIN SIGNALING IN DROSOPHILA MELANOGASTER

Early attempts to propagate Drosophila cells in culture revealed a growth factor requirement in defined medium which could be provided by purified bovine insulin, implying the existence of a related endogenous factor in Drosophila (Seecof and Dewhurst, 1974, Cell Differ. 3(1):63–70; Meneses and De Los Angeles Ortiz, 1975, Comp. Biochem. Physiol. A 51(2):483–5; Mosna and Barigozzi, 1976, Experientia 32(7):855–6; Davis and Shearn, 1977, Science 196 (4288):438–40; Petersen, et al., 1977, In Vitro 13(1):36–40; Mosna, 1981, Experientia 37(5):466–7; Wyss, 1982, Exp. Cell Res. 139(2):297–307). A bovine and human insulin were found to stimulate the differentiation of Drosophila cells grown in culture (Seecof and Dewhurst, 1974, Cell Differ. 3(1):63–70; Pimentel, et al., 1996, Biochem. Biophys. Res. Commun. 226(3):855–61). One report described the presence of an "insulin-like activity" in unpurified Drosophila extracts that elicited a hypoglycemic effect when injected into mice, although the activity was not particularly strong (Meneses and De Los Angeles Ortiz, 1975, Comp. Biochem. Physiol. A. 51(2):483–5). Another group (LeRoith, et al., 1981, Diabetes 30(1):70–6) fractionated an insulin-like material from Drosophila based on immunoreactivity and showed that this material had insulin-like activity on isolated rat adipocytes. Also, polyclonal antibodies raised against bovine/porcine insulin were used to localize insulin-immunoreactive material in Drosophila tissue (Gorczyca, et al., 1993, J. Neurosci. 13(9):3692–704), and specific insulin-inmunoreactive substances were detected at neuromuscular junctions and in the central nervous system.

However, these substances were not characterized further to validate that they correspond to bonafide insulin proteins at the level of primary protein sequence. Indeed, despite this long history of phenomenological evidence for insulin-like activities, true insulin-like genes and proteins in Drosophila have not been identified and characterized at the sequence level.

More compelling evidence for evolutionary conservation of insulin-like signaling pathways in Drosophila has come from the identification of an apparent homolog of the insulin receptor (Petruzzelli et al., 1986, Proc. Natl. Acad. Sci. U.S.A. 83:4710–4714). One insulin receptor homolog has been characterized thus far in Drosophila, termed InR (insulin receptor) also known as DIR (Drosophila insulin receptor) (Ruan et al., 1995, J. Biol. Chem. 270:4236–4243), which exhibits extensive homology with vertebrate insulin and IGF receptors in both the extracellular ligand-binding domain and the intracellular tyrosine kinase domain. InR is larger than the human insulin receptor protein due to extensions at both the N- and C-termini of the polypeptide chain. It is interesting that the additional C-terminal segment of the InR shares sequence features with IRS-1, one of the substrates of the insulin receptor tyrosine kinase in mammals. Genetic analysis of InR function in Drosophila has revealed that it is an essential gene with an apparent role in the development of the epidermis and nervous system, as well as growth control (Fernandez et al., 1995, EMBO J. 14:3373–3384). Flies that are homozygous for mutations in InR generally exhibit an embryonic lethal phenotype, but flies bearing certain heteroallelic combinations of InR mutations live to adulthood and the surviving animals have about 50% the normal body weight (Garafalo, Chen, et al., 1996, Endocrinology 137(3):846–56). This result is reminiscent of a similar phenotype observed in mutant mice lacking functional IGF-I receptor genes (Liu, et al., 1993, Cell 75(1):59–72). Aside from this potential role of InR in growth regulation, the role, if any, that InR may have in metabolic regulation in Drosophila remains unclear. The ligand binding specificity of InR has been examined using in vitro assays for receptor activation/phosphorylation, and competitive binding of test ligands compared to porcine insulin (Fernandez-Almonacid and Rosen, 1987, Mol. Cell Biol. 7(8):2718–27). Curiously, the results of this study indicated that InR binds vertebrate insulin, and does not apparently recognize vertebrate IGF-I or IGF-II, or even bombyxin-II from the silkworm, implying that the natural Drosophila ligands for InR may bear more structural resemblance to vertebrate insulin than to these other insulin superfamily proteins.

Two other Drosophila genes have been tentatively placed downstream of InR in signaling for growth control, based on preliminary data. Dominant negative and constitutively active forms of Drosophila Pi3K92E, encoding PI3-kinase cause growth defects when expressed in the fly eye and wing that are consistent with action downstream of InR (Leevers et al., 1996, EMBO J. 15(23):6584–94) and have been reported to interact genetically with InR mutants (Leevers et al., 1998, A. Conf. Dros. Res. 39:31). In addition, the *Drosophila chico* gene encodes a homologue of IRS-1. Mutations in chico are semi-lethal, with surviving adults having small body size consistent with the data on InR mutants (abstract Riesgo-Escovar, et al., 1998, A. Conf. Dros. Res. 39:32).

Recently, a Drosophila insulin-like gene has been isolated and characterized (see U.S. patent application Ser. No. 09/201,226 (Attorey Docket No. 7326-077 filed evendate herewith now U.S. Pat. No. 6,135,942 issued Oct. 24, 2000, entitled "NUCLCEIC ACIDS AND PROTEINS OF A *D. MELANOGASTER* INSULIN-LIKE GENE AND USES THEREOF" by Maria Leptin, which is incorporated herein by reference in its entirety).

2.4.3. UNANSWERED QUESTIONS

The structural homologies of components of the Drosophila InR pathway with those involved in insulin signaling in mammals, as well as the function of the InR pathway in controlling growth, and the circumstantial evidence for Drosophila insulin-like activities, raise critical questions with respect to further analysis of this pathway and its potential applications. For example, are there, in fact, insulin superfamily hormones in Drosophila? If so, how diverse is the insulin superfamily in Drosophila in terms of structure and function? Particularly, are Drosophila insulin-like proteins closer in structure and function to their vertebrate counterparts than those found in the nematode *C. elegans*? Further, what specific Drosophila insulin-like protein(s) interact with the InR receptor, or otherwise affect growth control? Are there other receptors for Drosophila insulin-like proteins aside from InR that are involved in regulating other functions, such as metabolism, development, reproduction, or longevity? Finally, how are the synthesis, activity and turnover of insulin-like proteins regulated in Drosophila? Answers to the foregoing questions would be much desired.

3. SUMMARY OF THE INVENTION

The present invention relates to the nucleotide sequences of *D. melanogaster* insulin-like genes, the amino acid sequences of their encoded proteins, and derivatives (e.g., fragments) and analogs thereof. Nucleic acids capable of hybridizing to or complementary to the foregoing nucleotide sequences are also provided. The invention also relates to a method of identifying genes that are modified by, or that participate in signal transduction with, *D. melangaster* insulin-like genes. The invention also relates to derivatives and analogs of *D. melangaster* insulin-like genes which are functionally active, i.e., which are capable of displaying one or more known functional activities associated with a full-length (wild-type) insulin-like protein. Such functional activities include but are not limited to antigenicity (ability to bind, or to compete for binding, to an anti-insulin antibody), immunogenicity (ability to generate antibody which binds to insulin), and ability to bind (or compete for binding) to a receptor for insulin (e.g., that is encoded by the *D. melanogaster* insulin receptor-like gene InR). The invention further relates to fragments (and derivatives and analogs thereof) of an insulin-like protein which comprise one or more domains of an insulin-like protein. Antibodies to an insulin-like protein, derivatives and analogs of an insulin-like protein, are additionally provided. Methods of production of the insulin-like proteins, derivatives and analogs, e.g., by recombinant means, are also provided. Methods to identify the biological function of a Drosophila insulin-like gene are provided, including various methods for the functional modification (e.g., overexpression, underexpression, mutation, knock-out) of one gene, or of two or more genes simultaneously. Methods to identify a Drosophila gene which modifies the function of, and/or functions in a downstream pathway from, an insulin-like gene are provided. The invention further provides for use of Drosophila insulin-like proteins as a media additive or pesticide.

This invention provides a purified protein comprising an amino acid sequence as depicted in FIG. 5 (SEQ ID NO:2). The invention further provides a purified protein comprising amino acid sequence numbers 30–120 as depicted in FIG. 5 (SEQ ID NO:2).

This invention provides a purified protein comprising an amino acid sequence as depicted in FIG. 6 (SEQ ID NO:4). The invention further provides a purified protein comprising amino acid sequence numbers 30–154 as depicted in FIG. 6 (SEQ ID NO:4).

This invention provides a purified protein comprising an amino acid sequence as depicted in FIG. 7 (SEQ ID NO:6). The invention further provides a purified protein comprising amino acid sequence numbers 27–137 as depicted in FIG. 7 (SEQ ID NO:6).

This invention provides a purified protein, the amino acid sequence of which consists of amino acids numbers 1–120 as depicted in FIG. 5 (SEQ ID NO:2). This invention further provides a purified protein, the amino acid sequence of which consists of amino acids numbers 30–120 as depicted in FIG. 5 (SEQ ID NO:2).

This invention provides a purified protein, the amino acid sequence of which consists of amino acids numbers 1–154 depicted in FIG. 6 (SEQ ID NO:4). This invention further provides a purified protein, the amino acid sequence of which consists of amino acids numbers 30–154 as depicted in FIG. 6 (SEQ ID NO:4).

This invention provides a purified protein, the amino acid sequence of which consists of amino acids numbers 1–137 as depicted in FIG. 7 (SEQ ID NO:6). This invention provides a purified protein, the amino acid sequence of which consists of amino acids numbers 27–137 as depicted in FIG. 7 (SEQ ID NO:6).

This invention provides a purified protein consisting of a B peptide domain defined by amino acid sequence numbers 30–54 as depicted in FIG. 5 (SEQ ID NO:2), linked by one or more disulfide bonds to an A peptide domain defined by amino acid sequence numbers 92–120 as depicted in FIG. 5 (SEQ ID NO:2).

This invention provides a purified protein comprising a B peptide domain defined by amino acid sequence numbers 30–54 as depicted in FIG. 5 (SEQ ID NO:2).

This invention provides a purified protein comprising an A peptide domain defined by amino acid sequence numbers 92–120 as depicted in FIG. 5 (SEQ ID NO:2).

This invention provides a purified protein consisting of a B peptide domain defined by amino acid sequence numbers 30–69 as depicted in FIG. 6 (SEQ ID NO:4), linked by one or more disulfide bonds to an A peptide domain defined by amino acid sequence numbers 128–154 as depicted in FIG. 6 (SEQ ID NO:4).

This invention provides a purified protein consisting of a B peptide domain defined by amino acid sequence numbers 30–69 as depicted in FIG. 6 (SEQ ID NO:4), linked by one or more disulfide bonds to an A peptide domain defined by amino acid sequence numbers 129–154 as depicted in FIG. 6 (SEQ ID NO:4).

This invention provides a purified protein comprising a B peptide domain defined by amino acid sequence numbers 30–69 as depicted in FIG. 6 (SEQ ID NO:4).

This invention provides a purified protein comprising an A peptide domain defined by amino acid sequence numbers 128–154 as depicted in FIG. 6 (SEQ ID NO:4).

This invention provides a purified protein comprising an A peptide domain defined by amino acid sequence numbers 129–154 as depicted in FIG. 6 (SEQ ID NO:4).

This invention provides a purified protein consisting of a B peptide domain defined by amino acid sequence numbers 27–50 as depicted in FIG. 7 (SEQ ID NO:6), linked by one or more disulfide bonds to an A peptide domain defined by amino acid sequence numbers 108–137 as depicted in FIG. 7 (SEQ ID NO:6).

This invention provides a purified protein consisting of a B peptide domain defined by amino acid sequence numbers 27–49 as depicted in FIG. 7 (SEQ ID NO:6), linked by one or more disulfide bonds to an A peptide domain defined by amino acid sequence numbers 108–137 as depicted in FIG. 7 (SEQ ID NO:6).

This invention provides a purified protein comprising a B peptide domain defined by amino acid sequence numbers 27–50 as depicted in FIG. 7 (SEQ ID NO:6).

This invention provides a purified protein comprising a B peptide domain defined by amino acid sequence numbers 27–49 as depicted in FIG. 7 (SEQ ID NO:6).

This invention provides a purified protein comprising an A peptide domain defined by amino acid sequence numbers 108–137 as depicted in FIG. 7 (SEQ ID NO:6).

This invention provides a purified fragment comprising at least 10 contiguous amino acids of a protein defined by an amino acid sequence as depicted in FIG. 5 (SEQ ID NO:2), FIG. 6 (SEQ ID NO:4), or FIG. 7 (SEQ ID NO:6), which fragment is capable of being bound by an antibody to said protein.

This invention provides a purified first protein comprising at least 10 contiguous amino acids of a second protein defined by an amino acid sequence as depicted in FIG. 5 (SEQ ID NO:2), FIG. 6 (SEQ ID NO:4), or FIG. 7 (SEQ ID NO:6), which first protein has only an insertion, deletion, or substitution relative to the sequence as depicted in FIG. 5 (SEQ ID NO:2), FIG. 6 (SEQ ID NO:4), or FIG. 7 (SEQ ID NO:6), and which first protein is capable of being bound by an antibody to said second protein.

This invention provides a purified protein comprising a fragment comprising at least 10 contiguous amino acids of a protein defined by an amino acid sequence as depicted in FIG. 5 (SEQ ID NO:2), FIG. 6 (SEQ ID NO:4), or FIG. 7 (SEQ ID NO:6), which fragment is capable of being bound by an antibody to said protein.

This invention provides a purified fragment of a protein consisting of an amino acid sequence depicted in FIG. 5 (SEQ ID NO:2), FIG. 6 (SEQ ID NO:4) or FIG. 7 (SEQ ID NO:6), said fragment comprising (a) at least 10 contiguous amino acids; and (b) a domain of said protein selected from the group consisting of a B peptide domain and an A peptide domain.

This invention provides a chimeric protein comprising the fragment comprising at least 10 contiguous amino acids of a protein defined by an amino acid sequence as depicted in FIG. 5 (SEQ ID NO:2), FIG. 6 (SEQ ID NO:4), or FIG. 7 (SEQ ID NO:6), which fragment is capable of being bound by an antibody to said protein, fused by a covalent bond to at least a portion of a second protein, which second protein is not said protein defined by an amino acid sequence as depicted in FIG. 5 (SEQ ID NO:2), FIG. 6(SEQ ID NO:4), or FIG. 7 (SEQ ID NO:6). In one embodiment, the chimeric protein comprising the fragment is fused by a covalent bond to at least a portion of a second protein, which second protein is not an amino acid sequence as depicted in FIG. 5 (SEQ ID NO:2), FIG. 6(SEQ ID NO:4), or FIG. 7 (SEQ ID NO:6). In another embodiment, the fragment is fused by a covalent bond to at least a portion of a second protein, which second protein is not a *D. melangaster* insulin-like protein.

This invention provides a purified molecule comprising a fragment of at least contiguous amino acids of a protein defined by an amino acid sequence of SEQ ID NO:2, SEQ ID NO:4, or SEQ ID NO:6, which fragment is capable of being bound by an antibody to said protein defined by the sequence selected from the group consisting of SEQ ID NO:2, SEQ ID NO:4, or SEQ ID NO:6.

This invention provides a chimeric protein comprising a fragment of a protein consisting of an amino acid sequence depicted in FIG. 5 (SEQ ID NO:2), FIG. 6 (SEQ ID NO:4) or FIG. 7 (SEQ ID NO:6), said fragment comprising (a) at least 10 contiguous amino acids; and (b) a domain of said protein selected from the group consisting of a B peptide domain and an A peptide domain, fused by a covalent bond to at least a portion of a second protein, which second protein is not said protein defined by an amino acid sequence as depicted in FIG. 5 (SEQ ID NO:2), FIG. 6(SEQ ID NO:4), or FIG. 7 (SEQ ID NO:6). In another embodiment, the fragment is fused by a covalent bond to at least a portion of a second protein, which second protein is not a *D. melangaster* insulin-like protein. In yet another embodiment, the fragment is capable of being bound by an antibody to a protein defined by an amino acid sequence as depicted in FIG. 5 (SEQ ID NO:2), FIG. 6 (SEQ ID NO:4), or FIG. 7 (SEQ ID NO:6).

This invention provides a purified molecule comprising a purified fragment of a protein consisting of an amino acid sequence depicted in FIG. 5 (SEQ ID NO:2), FIG. 6 (SEQ ID NO:4) or FIG. 7 (SEQ ID NO:6), said fragment comprising (a) at least contiguous amino acids; and (b) a domain of said protein selected from the group consisting of a B peptide domain and an A peptide domain.

This invention provides a purified antibody or derivative thereof, containing an idiotype capable of immunospecific binding to a protein consisting of an amino acid sequence depicted in FIG. 5 (SEQ ID NO:2), FIG. 6 (SEQ ID NO:4) or FIG. 7 (SEQ ID NO:6) and not to an insulin-like protein of another species. In one embodiment, the antibody is polyclonal. In another embodiment, the antibody is monoclonal.

This invention provides an isolated nucleic acid comprising a nucleotide sequence as depicted in FIG. 5 (SEQ ID NO:1) or FIG. 7 (SEQ ID NO:5).

This invention provides an isolated nucleic acid comprising a nucleotide sequence as depicted in FIG. 6 (SEQ ID NO:3), wherein said nucleic acid is less than 15 kilobases.

This invention provides an isolated nucleic acid comprising a nucleotide sequence encoding an amino acid sequence as depicted in FIG. 5 (SEQ ID NO:2), FIG. 6 (SEQ ID NO:4), or FIG. 7 (SEQ ID NO:6), wherein said nucleic acid is less than 15 kilobases.

This invention provides an isolated RNA molecule comprising a nucleotide sequence as depicted in FIG. 5 (SEQ ID NO:1), FIG. 6 (SEQ ID NO:3), or FIG. 7 (SEQ ID NO:5), wherein the base U (uracil) is substituted for the base T (thymine) of said sequence.

This invention provides an isolated RNA molecule comprising a nucleotide sequence encoding an amino acid sequence as depicted in FIG. 5 (SEQ ID NO:2), FIG. 6 (SEQ ID NO:4), or FIG. 7 (SEQ ID NO:6).

This invention provides an isolated first nucleic acid which hybridizes under conditions selected from the group consisting of high stringency, moderate stringency and low stringency, to a second nucleic acid defined by a nucleotide sequence as depicted in FIG. 5 (SEQ ID NO:1), FIG. 6 (SEQ ID NO:3), or FIG. 7 (SEQ ID NO:5), wherein said first nucleic acid is less than 15 kilobases. In one embodiment, the first nucleic acid encodes a first protein capable of being bound by an antibody to a second protein defined by the amino acid sequence as depicted in FIG. 5 (SEQ ID NO:2), FIG. 6 (SEQ ID NO:4), or FIG. 7 (SEQ ID NO:6).

This invention provides an isolated first nucleic acid which hybridizes under conditions selected from the group consisting of high stringency, moderate stringency and low stringency, to a second nucleic acid defined by the reverse complement a nucleotide sequence as depicted in FIG. 5 (SEQ ID NO:1), FIG. 6 (SEQ ID NO:3), or FIG. 7 (SEQ ID NO:5), wherein said first nucleic acid is less than 15 kilobases.

This invention provides a purified protein encoded by a first nucleic acid capable of hybridizing under conditions selected from the group consisting of high stringency, moderate stringency and low stringency, to a second nucleic acid defined by the reverse complement of a nucleotide sequence as depicted in FIG. 5 (SEQ ID NO:1), FIG. 6 (SEQ ID NO:3), or FIG. 7 (SEQ ID NO:5), wherein said protein is capable of being bound by an antibody to a second protein defined by an amino acid sequence as depicted in FIG. 5 (SEQ ID NO:2), FIG. 6, (SEQ ID NO:4), or FIG. 7 (SEQ ID NO:6).

This invention provides an isolated first nucleic acid which hybridizes under conditions selected from the group consisting of high stringency, moderate stringency and low stringency, to a second nucleic acid defined by a nucleotide sequence encoding an amino acid sequence as depicted in FIG. 5 (SEQ ID NO:2), FIG. 6 (SEQ ID NO:4), or FIG. 7 (SEQ ID NO:6), wherein said first nucleic acid is less than 15 kilobases. In one embodiment, the nucleic acid encodes a *D. melangaster* insulin-like protein or a fragment of at least 10 contiguous amino acids of said protein.

This invention provides an isolated first nucleic acid which hybridizes under conditions selected from the group consisting of high stringency, moderate stringency and low stringency, to a second nucleic acid defined by the reverse complement of a nucleotide sequence encoding an amino acid sequence as depicted in FIG. 5 (SEQ ID NO:2), FIG. 6 (SEQ ID NO:4), or FIG. 7 (SEQ ID NO:6), wherein said first nucleic acid is less than 15 kilobases.

This invention provides an isolated nucleic acid comprising a nucleotide sequence that is the reverse complement of a nucleotide sequence encoding an amino acid sequence as depicted in FIG. 5 (SEQ ID NO:2), FIG. 6 (SEQ ID NO:4), or FIG. 7 (SEQ ID NO:6).

This invention provides a method of producing a protein comprising: (a) growing a recombinant cell containing a nucleic acid comprising a recombinant nucleotide sequence as depicted in FIG. 5 (SEQ ID NO:1) or FIG. 7 (SEQ ID NO:5), such that the protein encoded by said nucleotide sequence is expressed by the cell; and (b) recovering the expressed protein. In one embodiment, the purified protein produced by the method is provided.

This invention provides a method of producing a protein comprising: (a) growing a recombinant cell containing a nucleic acid comprising a recombinant nucleotide sequence as depicted in FIG. 6 (SEQ ID NO:3) of less than 15 kilobases, such that the protein encoded by said nucleotide sequence is expressed by the cell; and (b) recovering the expressed protein. In one embodiment, the purified protein produced by the method is provided.

This invention provides a method of producing a protein comprising: (a) growing a recombinant cell containing a nucleic acid comprising a recombinant nucleotide sequence of less than 15 kilobases encoding a protein comprising an amino acid sequence as depicted in FIG. 5 (SEQ ID NO:2), FIG. 6 (SEQ ID NO:4), or FIG. 7 (SEQ ID NO:6), such that the encoded protein is expressed by the cell; and (b) recovering the expressed protein. In one embodiment, the purified protein produced by the method is provided.

This invention provides a method of identifying a phenotype associated with mutation or abnormal expression of a *D. melangaster* insulin-like protein comprising identifying an effect of a mutated or abnormally expressed *D. melangaster* insulin-like gene which encodes a *D. melangaster* insulin-like protein comprising an amino acid sequence as depicted in FIG. 5 (SEQ ID NO:2), FIG. 6 (SEQ ID NO:4), or FIG. 7 (SEQ ID NO:6), in a *D. melangaster* animal. In one embodiment, the effect is determined by an assay selected from the group consisting of a developmental assay, an energy metabolism assay, a growth rate assay, a reproductive capacity assay, a lethality assay, a sterility assay, a brood size assay, a life span assay, a locomotion assay, a body shape assay, a body plan assay, a body size assay, a body weight assay, a cell size assay, a cell division assay, a feeding assay, a developmental rate assay, and a morphogenesis assay. In another embodiment, the gene is mutated or abnormally expressed using a technique selected from the group consisting of radiation mutagenesis, chemical mutagenesis, transposon mutagenesis, antisense and double-stranded RNA interference.

This invention provides a method of identifying a phenotype associated with mutation or abnormal expression of a *D. melangaster* insulin-like protein comprising: (a) mutating or abnormally expressing a *D. melangaster* insulin-like gene which encodes a *D. melanogaster* insulin-like protein comprising an amino acid sequence as depicted in FIG. 5 (SEQ ID NO:2), FIG. 6 (SEQ ID NO:4), or FIG. 7 (SEQ ID NO:6), in a *D. melanogaster* animal, wherein the nucleotide sequence comprising SEQ ID NO:3 does not contain genomic sequence naturally contiguous with SEQ ID NO:3 of greater than 15 kilobases; and (b) identifying an effect of the gene mutated or abnormally expressed. In one embodiment, the effect is identified by an assay selected from the group consisting of a developmental assay, an energy metabolism assay, a growth rate assay, a reproductive capacity assay, a lethality assay, a sterility assay, a brood size assay, a life span assay, a locomotion assay, a body shape assay, a body plan assay, a body size assay, a body weight assay, a cell size assay, a cell division assay, a feeding assay, a developmental rate assay, and a morphogenesis assay. In another embodiment, the gene is mutated or abnormally expressed using a technique selected from the group consisting of radiation mutagenesis, chemical mutagenesis, transposon mutagenesis, antisense and double-stranded RNA interference.

This invention provides a recombinant cell containing a recombinant nucleic acid vector of less than 15 kilobases comprising a nucleotide sequence as depicted in FIG. 6 (SEQ ID NO:3).

This invention provides a recombinant cell containing a recombinant nucleic acid vector comprising a nucleotide sequence as depicted in FIG. 5 (SEQ ID NO:1) or FIG. 7 (SEQ ID NO:5).

This invention provides a vector comprising (a) a nucleotide sequence as depicted in FIG. 6 (SEQ ID NO:3), and (b) an origin of replication, wherein said vector does not contain genomic sequence naturally contiguous with SEQ ID NO:3 of greater than kilobases. In one embodiment, the nucleotide sequence is operably linked to a heterologous promoter.

This invention provides a vector comprising a nucleotide sequence selected from the group consisting of SEQ ID NO:1, and SEQ ID NO:5 and an origin of replication. In one embodiment, the nucleotide sequence is operably linked to a heterologous promoter.

This invention provides a method of identifying a gene-of-interest as capable of modifying a function of a *D. melangaster* insulin-like gene comprising: (a) constructing a first mutant fly having a first mutation in a *D. melangaster* insulin-like gene which encodes a *D. melangaster* insulin-like protein comprising an amino acid sequence as depicted in FIG. 5 (SEQ ID NO:2), FIG. 6 (SEQ ID NO:4), or FIG. 7 (SEQ ID NO:6) and a second mutation in the gene-of-interest; and (b) determining whether the phenotype displayed by the first mutant fly is different from the phenotype of a second mutant fly having said first mutation but not said second mutation, in which the displaying of a phenotype by the first mutant fly that is different from said second mutant fly identifies the gene-of-interest as capable of modifying the function of the *D. melangaster* insulin-like gene. In one embodiment, the first mutant fly is produced using a technique selected from the group consisting of radiation mutagenesis, chemical mutagenesis, transposon mutagenesis, antisense and double-stranded RNA interference. In another embodiment, the phenotype is selected from the group consisting of lethality, sterility, altered brood size, altered life span, altered locomotion, altered body shape, altered body plan, altered body size, altered body weight, altered cell size, altered cell division, altered feeding, altered development, altered metabolism, altered glycogen synthesis, altered glycogen storage, altered glycogen degradation, altered lipid synthesis, altered lipid storage, altered lipid degradation, altered levels of carbohydrate in hemolymph, altered levels of lipid in hemolymph, altered morphogenesis of organs, altered morphogenesis of tissues of the gonad, altered morphogenesis of the nervous system, altered fat body, altered hemocytes, altered morphogenesis of the peripheral sensory organs, altered imaginal discs, altered eye development, altered wing development, altered leg development, altered bristle development, altered antennae development, altered gut development, and altered musculature. In a further embodiment, the altered organ morphogenesis phenotype involves an organ selected from the group consisting of gonad, nervous system, fat body, hemocytes, peripheral sensory organs, imaginal discs, eye, wing, leg, antennae, gut, musculature, and bristle. In yet another embodiment, the fly having the altered phenotype is assayed for activity of a gene affecting body size selected from the group consisting of InR, chico, Pi3K92, Akt1, 14-3-3z, Lar, Pk61C, Glut3, Ide, shaggy, s6k, Ras85D, drk, Sos, rl, and Dsor1. In yet another embodiment, the gene-of-interest is a homolog of an insulin signaling pathway gene from vertebrates. In another embodiment, the gene-of-interest is selected from the group consisting of InR, chico, Pi3K92, Akt1, 14-3-3z, Lar, Pk61C, Glut3, Ide, shaggy, s6k, Ras85D, drk, Sos, rl, and Dsor1.

This invention provides a *D. melangaster* animal having a first mutation in a *D. melangaster* insulin-like gene comprising a nucleotide sequence as depicted in FIG. 5 (SEQ ID NO:1), FIG. 6 (SEQ ID NO:3), or FIG. 7 (SEQ ID NO:5), and a second mutation in a different gene that is a homolog of an insulin signaling pathway gene from vertebrates.

This invention provides a method of studying a function of a *D. melanogaster* insulin-like gene comprising: (a) mis-expressing a wild-type or mutant *D. melanogaster* insulin-like gene which encodes a *D. melangaster* insulin-like protein comprising an amino acid sequence as depicted in FIG. 5 (SEQ ID NO:2), FIG. 6 (SEQ ID NO:4), or FIG. 7 (SEQ ID NO:6) in a transgenic fly by driving expression with a homologous or heterologous promoter; and (b)

detecting a phenotype in said transgenic fly, so as to study the function of the *D. melangaster* insulin-like gene. In one embodiment, the heterologous promoter driving mis-expression is selected from the group consisting of a heat shock factor-responsive promoter, a GAL4-responsive promoter, a tTA-responsive promoter, a glass-responsive promoter, an eyeless enhancer-regulated promoter, a dpp enhancer-regulated promoter, and a vestigial enhancer-regulated promoter. In another embodiment, said transgenic fly mis-expressing the *D. melangaster* insulin-like gene further has a mutation in a gene selected from the group consisting of InR, chico, Pi3K92, Akt1, 14-3-3z, Lar, Pk61C, Glut3, Ide, shaggy, s6k, Ras85D, drk, Sos, rl, and Dsor1. In another embodiment, said transgenic fly mis-expressing the *D. melangaster* insulin-like gene is assayed for a change in a phenotype selected from the group consisting of lethality, sterility, altered brood size, altered life span, altered locomotion, altered body shape, altered body plan, altered body size, altered body weight, altered cell size, altered cell division, altered feeding, altered development, altered metabolism, altered glycogen synthesis, altered glycogen storage, altered glycogen degradation, altered lipid synthesis, altered lipid storage, altered lipid degradation, altered levels of carbohydrate in hemolymph, altered levels of lipid in hemolymph, altered morphogenesis of organs, altered morphogenesis of tissues of the gonad, altered morphogenesis of the nervous system, altered fat body, altered hemocytes, altered morphogenesis of the peripheral sensory organs, altered imaginal discs, altered eye development, altered wing development, altered leg development, altered bristle development, altered antennae development, altered gut development, and altered musculature.

This invention provides a method of detecting the effect of expression of a *D. melangaster* insulin-like gene which encodes a *D. melangaster* insulin-like protein comprising an amino acid sequence as depicted in FIG. 5 (SEQ ID NO:2), FIG. 6 (SEQ ID NO:4), or FIG. 7 (SEQ ID NO:6), on an insulin signaling pathway comprising: (a) mutating or abnormally expressing a wild-type *D. melangaster* insulin-like gene that encodes a protein comprising an amino acid sequence as depicted in FIG. 5 (SEQ ID NO:2), FIG. 6 (SEQ ID NO:4), or FIG. 7 (SEQ ID NO:6) in a fly already having a mutation in the insulin signaling pathway that displays a phenotype-of-interest; and (b) detecting the effect of step (a) on the phenotype-of-interest, so as to detect the effect of expression of the *D. melangaster* insulin-like gene. In one embodiment, the mutation in the insulin signaling pathway is in a gene selected from the group consisting of InR, chico, Pi3K92, Akt1, 14-3-3z, csw, Lar, Pk61C, Glut3, Ide, shaggy, s6k, Ras85D, drk, Sos, rl, an Dsor1.

This invention provides a method of identifying a molecule that binds to a ligand selected from the group consisting of (i) a *D. melangaster* insulin-like protein comprising an amino acid sequence as depicted in FIG. 5 (SEQ ID NO:2), FIG. 6 (SEQ ID NO:4), or FIG. 7 (SEQ ID NO:6), (ii) a fragment of the *D. melangaster* insulin-like protein comprising a domain of the protein, and (iii) a nucleic acid encoding the *D. melanogaster* insulin-like protein or fragment, the method comprising: (a) contacting the ligand with a plurality of molecules under conditions conducive to binding between the ligand and the molecules; and (b) identifying a molecule within the plurality that binds to the ligand. In one embodiment, the domain of the *D. melangaster* insulin-like protein is selected from the group consisting from a signal peptide domain, a pre peptide domain, a B peptide domain, a C peptide domain and an A peptide domain.

This invention provides a modified, isolated *D. melangaster* animal in which a *D. melangaster* insulin-like gene which encodes a *D. melangaster* insulin-like protein comprising an amino acid sequence as depicted in FIG. 5 (SEQ ID NO:2), FIG. 6 (SEQ ID NO:4), or FIG. 7 (SEQ ID NO:6) which has been deleted or inactivated by recombinant methods, or a progeny thereof containing the deleted or inactivated gene.

This invention provides a modified, isolated *D. melangaster* animal in which insulin-like gene has been deleted or inactivated by a method selected from the group consisting of radiation mutagenesis, chemical mutagenesis, transposon mutagenesis, antisense and double-stranded RNA interference.

This invention provides a recombinant non-human animal containing a *D. melanogaster* insulin-like transgene which encodes a *D. melangaster* insulin-like protein comprising an amino acid sequence as depicted in FIG. 5 (SEQ ID NO:2), FIG. 6 (SEQ ID NO:4), or FIG. 7 (SEQ ID NO:6). In one embodiment, the *D. melangaster* insulin-like transgene is under the control of a promoter that is not the native promoter of the transgene.

This invention provides a purified protein encoded by a first nucleic acid which hybridizes under conditions selected from the group consisting of high stringency, moderate stringency and low stringency, to a second nucleic acid, which second nucleic acid comprises a nucleotide sequence selected from the group consisting of SEQ ID NO:1, SEQ ID NO:3, and SEQ ID NO:5, wherein the protein is characterized as having a cleavable C peptide, and B and A chains, and as having the same number and relative spacing of Cys residues as found in vertebrate insulin-like proteins. In one embodiment, the B and A chain domains of the protein are not proteolytically cleaved into separate chains.

This invention provides a purified protein encoded by a first nucleic acid which hybridizes under conditions selected from the group consisting of high stringency, moderate stringency and low stringency, to a second nucleic acid, which second nucleic acid comprises a nucleotide sequence as depicted in FIG. 5 (SEQ ID NO:1), FIG. 6 (SEQ ID NO:3), or FIG. 7 (SEQ ID NO:5), wherein the protein is characterized as having a cleavable C peptide separating the B and A chains. In one embodiment, the B and A chain domains of the protein are not proteolytically cleaved into separate chains.

This invention provides a method of identifying a molecule that alters the expression level of a *D. melangaster* insulin-like gene corresponding to a cDNA sequence as depicted in FIG. 5 (SEQ ID NO:1), FIG. 6 (SEQ ID NO:3), or FIG. 7 (SEQ ID NO:5), which method comprises: (a) contacting a transgenic fly cell with one or more molecules, said transgenic fly cell having a transgene comprising a promoter or enhancer region of genomic DNA from 1 base to 6 kilobases upstream of the start codon of the cDNA sequence, operably linked to a reporter gene; and (b) determining whether the level of expression of the reporter gene is altered relative to the level of expression of the reporter gene in the absence of the one or more molecules. In one embodiment, the reporter gene encodes a protein selected from the group consisting of green fluorescent protein, lacZ protein, cre protein, FLP protein, reaper protein, hid protein, GAL4 protein, and tTA protein.

This invention provides a method of identifying a molecule that binds to a promoter or enhancer of a *D. melangaster* insulin-like gene corresponding to a cDNA sequence as depicted in FIG. 5 (SEQ ID NO:1), FIG. 6 (SEQ ID NO:3), or FIG. 7 (SEQ ID NO:5), which method comprises: (a) contacting a transgene comprising a promoter or enhancer region of genomic DNA from 1 base to 6 kilobases upstream of the start codon of the cDNA sequence operably linked to a reporter gene, with the molecule; and (b) determining whether the level of expression of the reporter gene is altered relative to the level of expression of the reporter gene in the absence of the one or more molecules. In one embodiment, the reporter gene encodes a protein selected from the group consisting of green fluorescent protein, lacZ protein, cre protein, FLP protein, reaper protein, hid protein, GAL4 protein, and tTA protein.

This invention provides a purified genomic nucleic acid consisting of a nucleotide sequence as depicted in FIG. 4 (SEQ ID NO:7).

This invention further provides a purified genomic nucleic acid consisting of a nucleotide sequence of less than 15 kilobases and comprising nucleotide numbers 1 to 967 as depicted in FIG. 4 (SEQ ID NO:7), or at least 20 contiguous nucleotides of SEQ ID NO:7.

This invention provides a purified genomic nucleic acid consisting of a nucleotide sequence of less than 15 kilobases and comprising nucleotide numbers 1583 to 11120 as depicted in FIG. 4 (SEQ ID NO:7) or at least 20 contiguous nucleotides of SEQ ID NO:7.

This invention provides a cell culture medium or medium supplement comprising (a) a sterile liquid carrier, and (b) a protein or fragment thereof, functional in promoting cell growth, survival, or differentiation, said protein comprising at least 10 contiguous amino acids as depicted in FIG. 5 (SEQ ID NO:2), FIG. 6 (SEQ ID NO:4), or FIG. 7 (SEQ ID NO:6).

This invention provides a cell culture medium or medium supplement comprising (a) a sterile liquid carrier, and (b) a protein encoded by a first nucleic acid which hybridizes under conditions selected from the group consisting of high stringency, moderate stringency and low stringency, to a second nucleic acid, which second nucleic acid comprises a nucleotide sequence selected from the group consisting of SEQ ID NO:1, SEQ ID NO:3, and SEQ ID NO:5, wherein the protein is characterized as having a cleavable C peptide, and B and A chains, and as having the same number and relative spacing of Cys residues as found in vertebrate insulin-like proteins, or a fragment thereof, functional in promoting cell growth, survival, or differentiation comprising at least 10 contiguous amino acids of said A chain or B chain of said protein. In one embodiment, the cell culture medium or medium supplement further comprises growth factors, vitamins, carbohydrates, antibiotics, antimicrobial agents, or salts. In another embodiment, the protein or fragment is purified.

This invention provides a method for growing, maintaining or differentiating a cell in culture comprising contacting the cell with an effective amount of a protein, said protein comprising an amino acid sequence as depicted in FIG. 5 (SEQ ID NO:2), FIG. 6 (SEQ ID NO:4), or FIG. 7 (SEQ ID NO:6), or a fragment of said protein functional in promoting cell growth, survival, or differentiation comprising at least 10 contiguous amino acids of an amino acid sequence as depicted in FIG. 5 (SEQ ID NO:2), FIG. 6 (SEQ ID NO:4), or FIG. 7 (SEQ ID NO:6). In one embodiment the protein or fragment is purified. In another embodiment, the cell is selected from the group consisting of an animal cell and a plant cell. In still another embodiment, the cell is a *D. melangaster* cell.

This invention provides a pesticide formulation comprising (a) a carrier, and (b) a protein, said protein comprising an amino acid sequence as depicted in FIG. 5 (SEQ ID NO:2), FIG. 6 (SEQ ID NO:4), or FIG. 7 (SEQ ID NO:6), or a pesticidal fragment of said protein, said fragment comprising at least 10 contiguous amino acids of said protein. In one embodiment, the protein or fragment is purified. In another embodiment, the carrier is selected from the group consisting of water, organic solvent, inorganic solvent, talc, pyrophyllite, synthetic fine silica, attapugus clay, kieselguhr chalk, diatomaceous earth, lime, calcium carbonate, bontonite, fuller's earth, cottonseed hulls, wheat flour, soybean flour, pumice, tripoli, wood flour, walnut shell flour, redwood flour, and lignin. In another embodiment, this invention provides a method for protecting a plant or animal against a pest comprising contacting the plant or animal with the pesticide formulation.

This invention provides a pesticide formulation comprising (a) a carrier, and (b) a purified nucleic acid encoding a protein comprising an amino acid sequence as depicted in FIG. 5 (SEQ ID NO:2), FIG. 6 (SEQ ID NO:4), or FIG. 7 (SEQ ID NO:6).

This invention provides a pesticide formulation comprising (a) a carrier, and (b) a nucleic acid, said nucleic acid comprising at least a portion of a nucleotide sequence as depicted in FIG. 5 (SEQ ID NO:1), FIG. 6 (SEQ ID NO:3), or FIG. 7 (SEQ ID NO:5), said portion encoding a protein functional as a pesticide. In one embodiment, the nucleic acid is purified. In another embodiment, the carrier is selected from the group consisting of water, organic solvent, inorganic solvent, talc, pyrophyllite, synthetic fine silica, attapugus clay, kieselguhr chalk, diatomaceous earth, lime, calcium carbonate, bontonite, fuller's earth, cottonseed hulls, wheat flour, soybean flour, pumice, tripoli, wood flour, walnut shell flour, redwood flour, and lignin. In another embodiment, the nucleic acid is a plasmid expression vector. In a further embodiment, the nucleic acid is contained in a recombinant virus. In a further embodiment, the recombinant virus is a baculovirus. In yet another embodiment, this invention provides a method for protecting a plant or animal against a pest comprising contacting the plant or animal with the pesticide formulation.

4. BRIEF DESCRIPTION OF THE DRAWINGS

FIG. 1. Structural organization of precursor forms of the insulin superfamily of hormones.

FIG. 2. Conserved structural features of insulin superfamily members. Human insulin B peptide (SEQ ID NO:20); Human insulin A peptide (SEQ ID NO:21); Human IGF-1 B and A peptides (SEQ ID NO:22); Human relaxin I B peptide (SEQ ID NO:23); Human relaxin I A peptide (SEQ ID NO:24); RLF B peptide (SEQ ID NO:25); RLF A peptide (SEQ ID NO:26); Placentin B peptide (SEQ ID NO:27); Placentin A peptide (SEQ ID NO:28); Bombyxin II B peptide (SEQ ID NO:29); Bombyxin II A peptide (SEQ ID NO:30); MIP I B peptide (SEQ ID NO:31); MIP I A peptide (SEQ ID NO:32); LIRP B peptide (SEQ ID NO:33); LIRP A peptide (SEQ ID NO:34).

FIG. 3. Gene map of Drosophila insulin-like gene cluster region, including location and orientation of coding regions of dIns1, dIns2, dIns3, and dIns4. Units in kbp indicate kilobase pairs of genomic DNA.

FIGS. 4A–4P. Annotated genomic DNA sequence of *D. melangaster* insulin-like gene cluster. Genomic sequence is set forth in SEQ ID NO:7. Coding regions for dIns1, dIns2, dIns4 and dIns3 are set forth in SEQ ID NO:16, SEQ ID NO:17, SEQ ID NO:6 and SEQ ID NO:4, respectively.

FIGS. 5A–5B Annotated sequence of *D. melangaster* insulin-like protein dIns2 and corresponding cDNA. dIns2 protein sequence is set forth in SEQ ID NO:2. dIns2 nucleic acid sequence is set forth in SEQ ID NO:1.

FIGS. 6A–6B Annotated sequence of *D. melangaster* insulin-like protein dIns3 and corresponding cDNA. dIns3 protein sequence is set forth in SEQ ID NO:4. dIns3 nucleic acid sequence is set forth in SEQ ID NO:3.

FIGS. 7A–7B Annotated sequence of *D. melangaster* insulin-like protein dIns4 and corresponding cDNA. dIns4 protein sequence is set forth in SEQ ID NO:6. dIns4 nucleic acid sequence is set forth in SEQ ID NO:5.

FIG. 8. Key structural features for *D. melangaster* Insulin-like protein folding and conserved Cysteine residues in vertebrate superfamily. Numbers shown in parentheses represents the number of residues omitted from the C peptide sequence. Shown sequences for Drosophila dIns1, dIns2, dIns3, dIns4; Invertebrate LIRP, bombyxin 11, MIP I, Ce F13B12; Human insulin, IGF-IA, RelHI are set forth in SEQ ID NOs: 35–45, respectively.

5. DETAILED DESCRIPTION OF THE INVENTION

As described herein, the inventors developed a strategy to search for novel insulin-like genes in the genome of Drosophila. Further, certain aspects of Drosophila insulin-like gene function have now been characterized as described herein. The results of this search have revealed a tightly clustered array of Drosophila insulin-like genes encoding proteins that are much closer in structure to vertebrate insulins than the insulin-like proteins found in the nematode *C. elegans*. Nonetheless, the Drosophila insulin-like proteins exhibit significant sequence diversity. These new insulin-like genes in Drosophila constitute very useful tools for probing the function and regulation of their corresponding pathways. Systematic genetic analysis of signaling pathways involving insulin-like proteins in Drosophila can be expected to lead to the discovery of new drug targets, therapeutic proteins, diagnostics and prognostics useful in the treatment of diseases and clinical problems associated with the function of insulin superfamily hormones in humans and other animals, as well as clinical problems associated with aging and senescence. Furthermore, analysis of these same pathways using Drosophila insulin-like proteins as tools will have utility for identification and validation of pesticide targets in invertebrate pests that are components of these signaling pathways.

Use of Drosophila insulin-like genes for such purposes as disclosed herein, has advantages over manipulation of other known components of the fruit fly InR pathway including InR, Pi3K92E, and chico. First, use of ligand-encoding Drosophila insulin-like genes provides a superior approach for identifying factors that are upstream of the receptor in the signal transduction pathway. Specifically, components involved in the synthesis, activation and turnover of insulin-like proteins may be identified. Furthermore, the discovery of multiple, different insulin-like hormones provides a rational approach to separate components involved in responses to different, specific environmental or regulatory signals. This is less technically feasible with manipulation of downstream components of the pathway found in target tissues. Further, the diversity of different insulin-like hormones provides a means to identify potential new receptor and/or signal transduction systems for insulin superfamily hormones that are structurally different from those that have been characterized to date, in either vertebrates or invertebrates. Still further, use of Drosophila as a system for analyzing the function and regulation of insulin-like genes has great advantages over approaches in other organisms due to the ability to rapidly carry out large-scale, systematic genetic screens as well as the ability to screen small molecules directly on whole organisms for possible therapeutic or pesticide use. Particularly, the Drosophila insulin-like genes described herein are significantly closer in structure to vertebrate insulin hormones than the insulin-like proteins of *C. elegans*; therefore, the fruit fly Drosophila may serve as a better model for vertebrate insulin function and signaling than the nematode *C. elegans* due to this greater structural similarity. Moreover, the fruit fly Drosophila is clearly the preferred genetic model organism for dissecting the function of insulin-like proteins, and validating potential pesticide targets, with respect to other insect pest species.

The present invention thus relates to proteins encoded by and nucleotide sequences of *D. melangaster* insulin-like genes. The invention further relates to fragments and other derivatives and analogs of such insulin-like proteins. Nucleic acids encoding such fragments or derivatives are also within the scope of the invention. Production of the foregoing proteins, e.g., by recombinant methods, is provided.

The invention also relates to insulin-like protein derivatives and analogs which are functionally active, i.e., which are capable of displaying one or more known functional activities associated with a full-length (wild-type) insulin-like protein. Such functional activities include but are not limited to antigenicity (ability to bind, or to compete for binding, to an anti-insulin-like protein antibody), immunogenicity (ability to generate antibody which binds to an insulin-like protein), and ability to bind (or compete for binding) to a receptor for insulin (e.g., that is encoded by the *D. melangaster* insulin receptor-like gene, InR).

The invention further relates to fragments (and derivatives and analogs thereof) of an insulin-like protein which comprise one or more domains of the insulin-like protein.

Antibodies to an insulin-like protein, its derivatives and analogs, are additionally provided.

Methods for genetic analysis of pathways involving insulin superfamily hormones in Drosophila are provided. Such methods may yield results of importance to human disease. For example, systematic identification of participants in intracellular signaling by insulin-like hormones, or components regulating secretion and turnover of insulin-like hormones, provide leads to the identification of drug targets, therapeutic proteins, diagnostics, or prognostics useful for treatment or management of insulin resistance in diabetics.

The invention is illustrated by way of examples set forth in Section 6 below which disclose, inter alia, the cloning and characterization of *D. melangaster* insulin-like genes.

For clarity of disclosure, and not by way of limitation, the detailed description of the invention is divided into the subsections which follow.

5.1. ISOLATION OF *D. MELANOGASTER* INSULIN-LIKE GENES

The invention relates to the nucleotide sequences of *D. melangaster* insulin-like nucleic acids. In specific embodiments, insulin-like nucleic acids comprise the cDNA sequences of SEQ ID NO:1, SEQ ID NO:3, or SEQ ID NO:5 or the coding regions thereof, or nucleic acids encoding an insulin-like protein (e.g., a protein having the sequence of SEQ ID NO:2, SEQ ID NO:4, or SEQ ID NO:6). As used herein, a gene "corresponding" to a cDNA sequence shall be construed to mean the gene that encodes the RNA from which the cDNA is derived. The invention provides purified or isolated nucleic acids consisting of at least 8 nucleotides (i.e., a hybridizable portion) of an insulin-like gene sequence; in other embodiments, the nucleic acids consist of at least 25 (continuous) nucleotides, 50 nucleotides, 100 nucleotides, 150 nucleotides, or 200 nucleotides of an insulin-like sequence, or a full-length insulin-like coding sequence. In another embodiment, the nucleic acids are smaller than 35, 200, or 500 nucleotides in length. Nucleic acids can be single or double stranded. The invention also relates to nucleic acids hybridizable to or complementary to the foregoing sequences or their reverse complements. In specific aspects, nucleic acids are provided which comprise a sequence complementary to at least 10, 25, 50, 100, or 200 nucleotides or the entire coding region of an insulin-like gene.

The invention further relates to the genomic nucleotide sequences of D. melanogaster insulin-like nucleic acids. In specific embodiments, insulin-like nucleic acids comprise the genomic sequences of SEQ ID NO:7 or the coding regions thereof, or nucleic acids encoding an insulin-like protein (e.g., a protein having the sequence of SEQ ID NO:2, SEQ ID NO:4, or SEQ ID NO:6).

In the above or alternative embodiments, the nucleic acids of the invention consist of a nucleotide sequence of not more than 2, 5, 10, 15, or 20 kilobases.

5.1.1. HYBRIDIZATION CONDITIONS

In a specific embodiment, a nucleic acid which is hybridizable to an insulin-like nucleic acid (e.g., having a sequence as set forth in SEQ ID NO:1, SEQ ID NO:3, or SEQ ID NO:5, or to its reverse complement, or to a nucleic acid encoding an insulin-like derivative, or to its reverse complement), under conditions of low stringency is provided. By way of example and not limitation, procedures using such conditions of low stringency are as follows (see also Shilo and Weinberg, 1981, Proc. Natl. Acad. Sci. U.S.A. 78, 6789–6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and re-exposed to film. Other conditions of low stringency which may be used are well known in the art (e.g., as employed for cross-species hybridizations).

In another specific embodiment, a nucleic acid which is hybridizable to an insulin-like nucleic acid, or its reverse complement, under conditions of high stringency is provided. By way of example and not limitation, procedures using such conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C. in prehybridization mixture containing 100 μg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

In another specific embodiment, a nucleic acid which is hybridizable to an insulin-like nucleic acid, or its reverse complement, under conditions of moderate stringency is provided. Selection of appropriate conditions for such stringencies is well known in the art (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, © 1987–1997, Current Protocols, © 1994–1997 John Wiley and Sons, Inc.).

Nucleic acids encoding derivatives and analogs of insulin-like proteins, and insulin-like antisense nucleic acids are additionally provided. As is readily apparent, as used herein, a "nucleic acid encoding a fragment or portion of an insulin-like protein" shall be construed as referring to a nucleic acid encoding only the recited fragment or portion of the insulin-like protein and not the other contiguous portions of the insulin-like protein as a continuous sequence.

Fragments of insulin-like nucleic acids comprising regions conserved between (i.e., with homology to) other insulin-like nucleic acids, of the same or different species, are also provided. Nucleic acids encoding one or more insulin-like domains are provided.

In a preferred specific embodiment, after hybridization, stringency conditions are as follows. Each membrane is washed two times each for 30 minutes each at 45° C. in 40 mM sodium phosphate, pH 7,2, 5% SDS, 1 mM EDTA, 0.5% bovine serum albumin, followed by four washes each for 30 minutes in sodium phosphate, pH 7.2, 1% SDS, 1 mM EDTA, and subsequently each membrane is treated differently as described below for low, medium, or high stringency hybridization conditions. For low stringency hybridization, membranes are not washed further. For medium stringency hybridization, membranes are additionally subjected to four washes each for 30 minutes in 40 mM sodium phosphate, pH 7.2, 1% SDS, 1 mM EDTA at 55° C. For high stringency hybridization, following the washes for low stringency, membranes are additionally subjected to four washes each for 30 minutes in 40 mM sodium phosphate, pH 7.2, 1% SDS, 1 mM EDTA at 55° C., followed by four washes each for 30 minutes in sodium phosphate, pH 7.2, 1% SDS, 1 mM EDTA at 65° C.

5.1.2. CLONING PROCEDURES

Specific embodiments for the cloning of an insulin-like gene follow. For expression cloning (a technique well known in the art), an expression library is constructed by any method known in the art. For example, mRNA is isolated, cDNA is made and ligated into an expression vector (e.g., a bacteriophage derivative) such that it is capable of being expressed by the host cell into which it is then introduced. Various screening assays can then be used to select for the expressed insulin-like product. In one embodiment, anti-insulin-like antibodies can be used for selection.

In another embodiment, polymerase chain reaction (PCR) is used to amplify the desired sequence in a genomic or cDNA library, prior to selection. Oligonucleotide primers representing known insulin-like sequences can be used as primers in PCR. In a preferred aspect, the oligonucleotide primers represent at least part of conserved segments of strong homology between insulin-like genes of different species. The synthetic oligonucleotides may be utilized as primers to amplify sequences from a source (RNA or DNA), preferably a cDNA library, of potential interest. PCR can be carried out, e.g., by use of a Perkin-Elmer Cetus thermal cycler and Taq polymerase (e.g., Gene Amp™). The nucleic acid being amplified can include mRNA or cDNA or genomic DNA from any species. One may synthesize degenerate primers for amplifying homologs from other species in the PCR reactions.

It is also possible to vary the stringency of hybridization conditions used in priming the PCR reactions, to allow for greater or lesser degrees of nucleotide sequence similarity between the known insulin-like nucleotide sequences and a nucleic acid homolog (or ortholog) being isolated. For cross species hybridization, low stringency conditions are preferred. For same species hybridization, moderately stringent conditions are preferred. After successful amplification of a segment of an insulin-like homolog, that segment may be cloned and sequenced by standard techniques, and utilized as a probe to isolate a complete cDNA or genomic clone. This, in turn, permits the determination of the gene's complete nucleotide sequence, the analysis of its expression, and the production of its protein product for functional analysis, as described below. In this fashion, additional genes encoding insulin-like proteins and insulin-like analogs may be identified.

In another embodiment, the organizational characteristics of the insulin-like genes may be used to identify clones containing novel members of the insulin-like gene superfamily. For example, but not by limitation, the insulin-like genes in the silkworm insect *B. mori* (which encode the bombyxin proteins) have been demonstrated to be organized in large multi gene clusters (Kondo, et al., 1996, J. Mol. Biol. 259:926–937). Identification and characterization of the genomic region surrounding a known insulin-like gene could, therefore, be used to identify additional genes that encode insulin-like proteins or insulin-like analogs which are located within these clusters, by methods described above and known in the art.

The above-described methods are not meant to limit the following general description of methods by which clones of insulin-like genes may be obtained.

Any eukaryotic cell potentially can serve as the nucleic acid source for molecular cloning of an insulin-like gene. The nucleic acid sequences encoding insulin-like proteins may be isolated from vertebrate, mammalian, human, porcine, bovine, feline, avian, equine, canine, as well as additional primate sources, insects (e.g., Drosophila), invertebrates, plants, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (see e.g., Sambrook et al., 1989, Molecular Cloning, A Laboratory Manual, 2d Ed., Vol. 1, II, Cold Spring Harbor Laboratory Press, Cold Spring Harbor, N.Y.; Glover, ed., 1985, DNA Cloning: A Practical Approach, MRL Press, Ltd., Oxford, U.K.). Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNase in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if a portion of an insulin-like gene or its specific RNA or a fragment thereof is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene.

Alternatively, the presence of the desired gene may be detected by assays based on the physical, chemical, or immunological properties of its expressed product. For example, cDNA clones, or DNA clones which hybrid-select the proper mRNAs, can be selected and expressed to produce a protein that has, e.g., similar or identical electrophoretic migration, isoelectric focusing behavior, proteolytic digestion maps, hormonal activity, binding activity, or antigenic properties as known for an insulin-like protein. Using an antibody to a known insulin-like protein, other insulin-like proteins may be identified by binding of the labeled antibody to expressed putative insulin-like proteins, e.g., in an ELISA (enzyme-linked immunosorbent assay)-type procedure. Further, using a binding protein specific to a known insulin-like protein, other insulin-like proteins may be identified by binding to such a protein (see e.g., Clemmons, 1993, Mol. Reprod. Dev. 35:368–374; Loddick et al., 1998, Proc. Natl. Acad. Sci. U.S.A. 95:1894–1898).

An insulin-like gene can also be identified by mRNA selection using nucleic acid hybridization followed by in vitro translation. In this procedure, fragments are used to isolate complementary mRNAs by hybridization. Such DNA fragments may represent available, purified insulin-like DNA of another species (e.g., Drosophila, mouse, human). Immunoprecipitation analysis or functional assays (e.g. aggregation ability in vitro, binding to receptor, etc.) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against insulin-like protein. A radiolabeled insulin-like cDNA can be synthesized using the selected mRNA (from the adsorbed polysomes) as a template. The radiolabeled mRNA or cDNA may then be used as a probe to identify the insulin-like DNA fragments from among other genomic DNA fragments.

Alternatives to isolating the insulin-like genomic DNA include, but are not limited to, chemically synthesizing the gene sequence itself from a known sequence or making cDNA to the mRNA which encodes the insulin-like protein. For example, RNA for cDNA cloning of the insulin-like gene can be isolated from cells which express the gene.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives or the Bluescript vector (Stratagene U.S.A., La Jolla, Calif.). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and an insulin-like gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In an additional embodiment, the desired gene may be identified and isolated after insertion into a suitable cloning vector using a strategy that combines a "shot gun" approach with a "directed sequencing" approach. Here, for example, the entire DNA sequence of a specific region of the genome, such as a sequence tagged site (STS), can be obtained using clones that molecularly map in and around the region of interest.

In specific embodiments, transformation of host cells with recombinant DNA molecules that incorporate an isolated insulin-like gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The insulin-like sequences provided by the instant invention include those nucleotide sequences encoding substantially the same amino acid sequences as found in native insulin-like proteins, and those encoded amino acid sequences with functionally equivalent amino acids, as well as those encoding other insulin-like derivatives or analogs, as described in below for insulin-like derivatives and analogs.

5.2. EXPRESSION OF D. MELANOGASTER INSULIN-LIKE GENES

The nucleotide sequence coding for an insulin-like protein or a functionally active analog or fragment or other derivative thereof (see Section 5.6), can be inserted into an appropriate expression vector, i.e., a vector which contains the necessary elements for the transcription and translation of the inserted protein-coding sequence. The necessary transcriptional and translational signals can also be supplied by the native insulin-like gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In yet another embodiment, a fragment of an insulin-like protein comprising one or more domains of the insulin-like protein is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of a nucleic acid sequence encoding an insulin-like protein or peptide fragment may be regulated by a second nucleic acid sequence so that the insulin-like protein or peptide is expressed in a host transformed with the recombinant DNA molecule. For example, expression of an insulin-like protein may be controlled by any promoter/enhancer element known in the art. A promoter/enhancer may be homologous (i.e. native) or herterologous (i.e. not native). Promoters which may be used to control insulin-like gene expression include, but are not limited to, the SV40 early promoter region (Benoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), prokaryotic expression vectors such as the β-lactamase promoter (Villa-Kamaroffet al., 1978, Proc. Natl. Acad. Sci. U.S.A. 75:3727–3731), or the lac promoter (DeBoer et al., 1983, Proc. Natl. Acad. Sci. U.S.A. 80:21–25; Scientific American, 1980, 242:74–94), plant expression vectors comprising the nopaline synthetase promoter region (Herrera-Estrella et al., Nature 303:209–213), the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120), promoter elements from yeast or other fungi such as the Gal4-responsive promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); a gene control region which is active in pancreatic beta cells (Hanahan, 1985, Nature 315:115–122), an immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

In a specific embodiment, a vector is used that comprises a promoter operably linked to an insulin-like gene nucleic acid, one or more origins of replication, and, optionally, one or more selectable markers (e.g., an antibiotic resistance gene).

In a specific embodiment, an expression construct is made by subcloning an insulin-like coding sequence into the EcoRI restriction site of each of the three pGEX vectors (Glutathione S-Transferase expression vectors; Smith and Johnson, 1988, Gene 7:31–40). This allows for the expression of the insulin-like protein product from the subclone in the correct reading frame.

In another specific embodiment, the promoter that is operably linked to the Drosophila insulin-like gene is not the native Drosophila insulin-like gene promoter (i.e. it is a heterologous promoter).

Expression vectors containing insulin-like gene inserts can be identified by three general approaches: (a) nucleic acid hybridization; (b) presence or absence of "marker" gene functions; and (c) expression of inserted sequences. In the first approach, the presence of an insulin-like gene inserted in an expression vector can be detected by nucleic acid hybridization using probes comprising sequences that are homologous to an inserted insulin-like gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of an insulin-like gene in the-vector. For example, if the insulin-like gene is inserted within the marker gene sequence of the vector, recombinants containing the insulin-like insert can be identified by the absence of the marker gene function. In the third approach, recombinant expression vectors can be identified by assaying the insulin-like product expressed by the recombinant. Such assays can be based, for example, on the physical or functional properties of the insulin-like protein in in vitro assay systems, e.g. binding with anti-insulin-like protein antibody.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda phage), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered insulin-like protein may be controlled. Furthermore, different host cells have characteristic and specific mechanisms for the translational and post-translational processing and modification (e.g. glycosylation, phosphorylation of proteins. Appropriate cell lines or host systems can be chosen to ensure the desired modification and processing of the foreign protein expressed. For example, expression in a bacterial system can be used to produce a non-glycosylated core protein product. Expression in yeast will produce a glycosylated product. Expression in animal cells can be used to ensure "native" glycosylation of a heterologous protein. Furthermore, different vector/host expression systems may effect processing reactions to different extents.

In other specific embodiments, the insulin-like protein, fragment, analog, or derivative may be expressed as a fusion, or chimeric protein product (comprising the protein, fragment, analog, or derivative joined via a peptide bond to a heterologous protein sequence (of a different protein)). A chimeric protein may include fusion of the insulin-like protein, fragment, analog, or derivative to a second protein or at least a portion thereof, wherein a portion is one (preferably 10, 15, or 20) or more amino acids of said second protein. The second protein, or one or more amino acid portion thereof, may be from a different Drosophila insulin-like protein or may be from a protein that is not a Drosophila insulin-like protein. Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

5.3. IDENTIFICATION AND PURIFICATION OF GENE PRODUCTS

In particular aspects, the invention provides amino acid sequences of insulin-like proteins and fragments and derivatives thereof which comprise an antigenic determinant (i.e., can be recognized by an antibody) or which are otherwise functionally active, as well as nucleic acid sequences encoding the foregoing. "Functionally active" insulin-like material as used herein refers to that material displaying one or more functional activities associated with a full-length (wild-type) insulin-like protein, e.g., binding to an insulin-like receptor (e.g., InR or insulin-like protein binding partner, antigenicity (binding to an anti-insulin-like protein antibody), immunogenicity, etc.

In specific embodiments, the invention provides fragments of an insulin-like protein consisting of at least 10 amino acids, 20 amino acids, 50 amino acids, or of at least 75 amino acids. In other embodiments, the proteins comprise or consist essentially of an insulin-like B peptide domain, an insulin-like A peptide domain, an insulin-like C peptide domain, or any combination of the foregoing, of an insulin-like protein. Fragments, or proteins comprising fragments, lacking some or all of the foregoing regions of a insulin-like protein are also provided. Nucleic acids encoding the foregoing are provided. In specific embodiments, the foregoing proteins or fragments are not more than 25, 50, or 100 contiguous amino acids.

Once a recombinant which expresses the insulin-like gene sequence is identified, the gene product can be analyzed. This is achieved by assays based on the physical or functional properties of the product, including radioactive labeling of the product followed by analysis by gel electrophoresis, immunoassay, etc.

Once the insulin-like protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay (see Section 5.7).

Alternatively, once an insulin-like protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller et al., 1984, Nature 310:105–111).

In another alternate embodiment, native insulin-like proteins can be purified from natural sources, by standard methods such as those described above (e.g., immunoaffinity purification).

In a specific embodiment of the present invention, such insulin-like proteins, whether produced by recombinant DNA techniques or by chemical synthetic methods or by purification of native proteins, include but are not limited to those containing, as a primary amino acid sequence, all or part of the amino acid sequence substantially as depicted in FIGS. 5–7 (SEQ ID NO:2, SEQ ID NO:4, or SEQ ID NO:6, respectively), as well as fragments and other derivatives, and analogs thereof, including proteins homologous thereto.

5.4. STRUCTURE OF INSULIN-LIKE GENES AND PROTEINS

The structure of insulin-like genes and proteins of the invention can be analyzed by various methods known in the art. Some examples of such methods are described below.

5.4.1. GENETIC ANALYSIS

The cloned DNA or cDNA corresponding to an insulin-like gene can be analyzed by methods including but not limited to Southern hybridization (Southern, 1975, J. Mol. Biol. 98:503–517), Northern hybridization (see e.g., Freeman et al., 1983, Proc. Natl. Acad. Sci. U.S.A. 80:4094–4098), restriction endonuclease mapping (Maniatis, 1982, Molecular Cloning, A Laboratory Manual, Cold Spring Harbor Laboratory Press, Cold Spring Harbor, N.Y.), and DNA sequence analysis. Accordingly, this invention provides nucleic acid probes recognizing an insulin-like gene. For example, polymerase chain reaction (PCR; U.S. Pat. Nos. 4,683,202, 4,683,195 and 4,889,818; Gyllenstein et al., 1988, Proc. Natl. Acad. Sci. U.S.A. 85:7652–7656; Ochman et al., 1988, Genetics 120:621–623; Loh et al., 1989, Science 243:217–220) followed by Southern hybridization with an insulin-like gene-specific probe can allow the detection of an insulin-like gene in DNA from various cell types. Methods of amplification other than PCR are commonly known and can also be employed. In one embodiment, Southern hybridization can be used to determine the genetic linkage of an insulin-like gene. Northern hybridization analysis can be used to determine the expression of an insulin-like gene. Various cell types, at various states of development or activity can be tested for insulin-like gene expression. The stringency of the hybridization conditions for both Southern and Northern hybridization can be manipulated to ensure detection of nucleic acids with the desired degree of relatedness to the specific insulin-like gene probe used. Modifications of these methods and other methods commonly known in the art can be used.

Restriction endonuclease mapping can be used to roughly determine the genetic structure of an insulin-like gene. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499–560), the Sanger dideoxy method (Sanger et al., 1977, Proc. Natl. Acad. Sci. U.S.A. 74:5463), the use of T7 DNA polymerase (Tabor and Richardson, U.S. Pat. No. 4,795,699), or use of an automated DNA sequenator (e.g., Applied Biosystems, Foster City, Calif.).

5.4.2. PROTEIN ANALYSIS

The amino acid sequence of an insulin-like protein can be derived by deduction from the DNA sequence, or alternatively, by direct sequencing of the protein, e.g., with an automated amino acid sequencer.

An insulin-like protein sequence can be further characterized by a hydrophilicity analysis (Hopp and Woods, 1981, Proc. Natl. Acad. Sci. U.S.A. 78:3824). A hydrophilicity profile can be used to identify the hydrophobic and hydrophilic regions of the insulin-like protein and the corresponding regions of the gene sequence which encode such regions.

Structural prediction analysis (Chou and Fasman, 1974, Biochemistry 13:222) can also be done, to identify regions of an insulin-like protein that assume specific secondary structures.

Manipulation, translation, and secondary structure prediction, open reading frame prediction and plotting, as well as determination of sequence homologies, can also be accomplished using computer software programs available in the art.

Other methods of structural analysis can also be employed. These include but are not limited to X-ray crystallography (Engstom, 1974, Biochem. Exp. Biol. 11:7–13), nuclear magnetic resonance spectroscopy (Clore and Gonenbom, 1989, CRC Crit. Rev. Biochem. 24:479–564) and computer modeling (Fletterick and Zoller, 1986, Computer Graphics and Molecular Modeling, in *Current Communications in Molecular Biology*, Cold Spring Harbor Laboratory Press, Cold Spring Harbor, N.Y.).

5.5. ANTIBODIES

According to the invention, insulin-like protein, its fragments or other derivatives, or analogs thereof, may be used as an immunogen to generate antibodies which immunospecifically bind such an immunogen. Such antibodies include but are not limited to polyclonal, monoclonal, chimeric, single chain, Fab fragments, and an Fab expression library. In another embodiment, antibodies to a domain (e.g. an insulin-like receptor binding domain) of an insulin-like protein are produced. In a specific embodiment, fragments of an insulin-like protein identified as hydrophilic are used as immunogens for antibody production.

Various procedures known in the art may be used for the production of polyclonal antibodies to an insulin-like protein or derivative or analog. In a particular embodiment, rabbit polyclonal antibodies to an epitope of an insulin-like protein consisting of the sequence of SEQ ID NO:2, SEQ ID NO:4, or SEQ ID NO:6, or a subsequence thereof, can be obtained. For the production of antibody, various host animals can be immunized by injection with the native insulin-like protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed to an insulin-like protein sequence or analog thereof, any technique which provides for the production of antibody molecules by continuous cell lines in culture may be used. For example, the hybridoma technique originally developed by Kohler and Milstein, (Kohler and Milstein 1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (see e.g., PCT/US90/02545). According to the invention, human antibodies may be used and can be obtained by using human hybridomas (Cole et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for an insulin-like protein together with genes from a human antibody molecule of appropriate biological activity can be used; such antibodies are within the scope of this invention.

According to the invention, techniques described for the production of single chain antibodies (U.S. Pat. No. 4,946,778) can be adapted to produce insulin-like-specific single chain antibodies. An additional embodiment of the invention utilizes the techniques described for the construction of Fab' expression libraries (Huse et al., 1989, Science 246:1275–1281) to allow rapid and easy identification of monoclonal Fab fragments with the desired specificity for insulin-like proteins, derivatives, or analogs.

Antibody fragments which contain the idiotype of the molecule can be generated by known techniques. For example, such fragments include but are not limited to, the $F(ab')_2$ fragment which can be produced by pepsin digestion of the antibody molecule, the Fab' fragments which can be generated by reducing the disulfide bridges of the $F(ab')_2$ fragment, the Fab fragments which can be generated by treating the antibody molecule with papain and a reducing agent, and Fv fragments.

In the production of antibodies, screening for the desired antibody can be accomplished by techniques known in the art (e.g., enzyme-linked immunosorbent assay or ELISA). For example, to select antibodies which recognize a specific domain of a insulin-like protein, one may assay generated hybridomas for a product which binds to a insulin-like fragment containing such domain. For selection of an antibody that specifically binds a first insulin-like homolog but which does not specifically bind a different insulin-like homolog, one can select on the basis of positive binding to the first insulin-like homolog and a lack of binding to the second insulin-like homolog.

Antibodies specific to a domain of an insulin-like protein are also provided. Antibodies specific to an epitope of an insulin-like protein are also provided.

The foregoing antibodies can be used in methods known in the art relating to the localization and activity of the insulin-like protein sequences of the invention, e.g., for imaging these proteins, measuring levels thereof in appropriate physiological samples, in diagnostic methods, etc.

5.6. INSULIN-LIKE PROTEINS, DERIVATIVES AND ANALOGS

The invention further relates to insulin-like proteins, derivatives (including but not limited to fragments), analogs, and molecules of insulin-like proteins. As used herein, a molecule defined by a particular SEQ ID NO, shall be construed to mean that the sequence of that molecule consists of that SEQ ID NO. Nucleic acids encoding insulin-like protein derivatives and protein analogs are also provided. In one embodiment, the insulin-like proteins are encoded by the insulin-like nucleic acids described in Section 5.1 above. In particular aspects, the proteins, derivatives, or analogs are of insulin-like proteins encoded by the sequence of SEQ ID NO:1, SEQ ID NO:3, SEQ ID NO:5, or SEQ ID NO:7.

The production and use of derivatives and analogs related to an insulin-like protein are within the scope of the present invention. In a specific embodiment, the derivative or analog is functionally active, i.e., capable of exhibiting one or more functional activities associated with a full-length, wild-type insulin-like protein. As one example, such derivatives or analogs which have the desired immunogenicity or antigenicity can be used in immunoassays, for immunization, for inhibition of insulin-like activity, etc. As another example, such derivatives or analogs which have the desired binding activity can be used for binding to the InR gene product. As yet another example, such derivatives or analogs which have the desired binding activity can be used for binding to a binding protein specific for a known insulin-like protein (see e.g., Clemmons, 1993, Mol. Reprod. Dev. 35:368–374; Loddick et al., 1998, Proc. Natl. Acad. Sci. U.S.A. 95:1894–1898). Derivatives or analogs that retain, or alternatively lack or inhibit, a desired insulin-like protein property-of-interest (e.g., binding to an insulin-like protein binding partner), can be used as inducers, or inhibitors, respectively, of such property and its physiological correlates. A specific embodiment relates to an insulin-like protein fragment that can be bound by an anti-insulin-like protein antibody. Derivatives or analogs of an insulin-like protein can be tested for the desired activity by procedures known in the art, including but not limited to the assays described in Section (5.10 and 5.11 below)

In particular, insulin-like derivatives can be made by altering insulin-like sequences by substitutions, additions (e.g., insertions) or deletions that provide for functionally equivalent molecules. Due to the degeneracy of nucleotide coding sequences, other DNA sequences which encode substantially the same amino acid sequence as an insulin-like gene may be used in the practice of the present invention. These include but are not limited to nucleotide sequences comprising all or portions of an insulin-like gene which is altered by the substitution of different codons that encode a functionally equivalent amino acid residue within the sequence, thus producing a silent change. Likewise, the insulin-like derivatives of the invention include, but are not limited to, those containing, as a primary amino acid sequence, all or part of the amino acid sequence of an insulin-like protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are generally understood to be conservative substitutions.

In a specific embodiment of the invention, proteins consisting of or comprising a fragment of an insulin-like protein consisting of at least 10 (continuous) amino acids of the insulin-like protein is provided. In other embodiments, the fragment consists of at least 20 or at least 50 amino acids of the insulin-like protein. In specific embodiments, such fragments are not larger than 35, 100 or 200 amino acids.

Derivatives or analogs of insulin-like proteins include but are not limited to those molecules comprising regions that are substantially homologous to an insulin-like protein or fragment thereof (e.g. in various embodiments, at least 60% or 70% or 80% or 90% or 95% identity over an amino acid sequence of identical size or when compared to an aligned sequence in which the alignment is done by a computer homology program known in the art) or whose encoding nucleic acid is capable of hybridizing to a coding insulin-like gene sequence, under high stringency, moderate stringency, or low stringency conditions.

Specifically, by way of example computer programs for determining homology may include but are not limited to TBLASTN, BLASTP, FASTA, TFASTA, and CLUSTALW (Pearson and Lipman, 1988, Proc. Natl. Acad. Sci. USA 85(8):2444–8; Altschul et al., 1990, J. Mol. Biol. 215(3):403–10; Thompson, et al., 1994, Nucleic Acids Res. 22(22):4673–80; Higgins, et al., 1996, Methods Enzymol 266:383–402; Altschul, et al., 1990, J. Mol. Biol. 215(3):403–10).

Specifically, Basic Local Alignment Search Tool (BLAST) (www.ncbi.nlm.nih.gov) (Altschul et al., 1990, J. of Molec. Biol., 215:403–410, "The BLAST Algorithm; Altschul et al., 1997, Nuc. Acids Res. 25:3389–3402) is a heuristic search algorithm tailored to searching for sequence similarity which ascribes significance using the statistical methods of Karlin and Altschul 1990, Proc. Nat'l Acad. Sci. USA, 87:2264–68; 1993, Proc. Nat'l Acad. Sci. USA 90:5873–77. Five specific BLAST programs perform the following tasks: 1) The BLASTP program compares an amino acid query sequence against a protein sequence database; 2) The BLASTN program compares a nucleotide query sequence against a nucleotide sequence database; 3) The BLASTX program compares the six-frame conceptual translation products of a nucleotide query sequence (both strands) against a protein sequence database; 4) The TBLASTN program compares a protein query sequence against a nucleotide sequence database translated in all six reading frames (both strands); 5) The TBLASTX program compares the six-frame translations of a nucleotide query sequence against the six-frame translations of a nucleotide sequence database.

Smith-Waterman (database: European Bioinformatics Institute wwwz.ebi.ac.uk/bic_sw/) (Smith-Waterman, 1981, J. of Molec. Biol., 147:195–197) is a mathematically rigorous algorithm for sequence alignments.

FASTA (see Pearson et al., 1988, Proc. Nat'l Acad. Sci. USA, 85:2444–2448) is a heuristic approximation to the Smith-Waterman algorithm. For a general discussion of the procedure and benefits of the BLAST, Smith-Waterman and FASTA algorithms see Nicholas et al., 1998, "A Tutorial on Searching Sequence Databases and Sequence Scoring Methods" (www.psc.edu) and references cited therein.

The insulin-like derivatives and analogs of the invention can be produced by various methods known in the art. The manipulations which result in their production can occur at the gene or protein level. For example, a cloned insulin-like gene sequence can be modified by any of numerous strategies known in the art (Sambrook et al., 1989, *Molecular Cloning, A Laboratory Manual*, 2d ed., Cold Spring Harbor Laboratory Press, Cold Spring Harbor, N.Y.). The sequence can be cleaved at appropriate sites with restriction endonuclease(s), followed by further enzymatic modification if desired, isolated, and ligated in vitro. In the production of a modified gene encoding a derivative or analog of an insulin-like protein, care should be taken to ensure that the modified gene remains within the same translational reading frame as the native protein, uninterrupted by translational stop signals, in the gene region where the desired insulin-like protein activity is encoded.

Additionally, an insulin-like nucleic acid sequence can be mutated in vitro or in vivo, to create and/or destroy translation, initiation, and/or termination sequences, or to create variations in coding regions and/or to form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson et al., 1978, J. Biol. Chem. 253:6551), use of TAB® linkers (Pharmacia), PCR with primers containing a mutation, etc.

Manipulations of an insulin-like protein sequence may also be made at the protein level. Included within the scope of the invention are insulin-like protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

In addition, analogs and derivatives of an insulin-like protein can be chemically synthesized. For example, a peptide corresponding to a portion of an insulin-like protein which comprises the desired domain, or which mediates the desired activity in vitro, can be synthesized by use of a peptide synthesizer. Furthermore, if desired, nonclassical amino acids or chemical amino acid analogs can be introduced as a substitution or addition into the insulin-like sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, an insulin-like protein derivative is a chimeric or fusion protein comprising an insulin-like protein or fragment thereof (preferably consisting of at least a domain or motif of the insulin-like protein, or at least 10 amino acids of the insulin-like protein) joined at its amino- or carboxy-terminus via a peptide bond to an amino acid sequence of a different protein. In specific embodiments, the amino acid sequence of the different protein is at least 6, 10, 20 or 30 continuous amino acids of the different proteins or a portion of the different protein that is functionally active. In one embodiment, such a chimeric protein is produced by recombinant expression of a nucleic acid encoding the protein (comprising an insulin-like-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art.

Alternatively, such a chimeric product may be made by protein synthetic techniques, e.g., by use of a peptide synthesizer. Chimeric genes comprising portions of an insulin-like gene fused to any heterologous protein-encoding sequences may be constructed. A specific embodiment relates to a chimeric protein comprising a fragment of an insulin-like protein of at least six amino acids, or a fragment that displays one or more functional activities of the insulin-like protein.

In another specific embodiment, the insulin-like derivative is a molecule comprising a region of homology with a insulin-like protein. By way of example, in various embodiments, a first protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region or when compared to an aligned sequence of the second region that has been aligned by a computer homology program known in the art. For example, a molecule can comprise one or more regions homologous to an insulin-like domain (see Section 5.6.1) or a portion thereof.

In a specific embodiment, the invention relates to insulin-like derivatives and analogs, in particular insulin-like fragments and derivatives of such fragments, that comprise, or alternatively consist of, one or more domains of an insulin-like protein, including but not limited to an insulin-like B peptide domain, an insulin-like A peptide domain, or an insulin-like connecting (C) peptide domain.

A specific embodiment relates to molecules comprising specific fragments of an insulin-like protein that are those fragments in the respective insulin-like proteins of the invention most homologous to specific fragments of a human or mouse insulin-like protein. A fragment comprising a domain of an insulin-like homolog can be identified by protein analysis methods well known in the art.

In another specific embodiment, a molecule is provided that comprises one or more domains (or functional portion thereof) of an insulin-like protein but that also lacks one or more domains (or functional portion thereof) of an insulin-like protein. In particular examples, insulin-like protein derivatives are provided that contain either an A peptide domain or a B peptide domain. By way of another example, such a protein may retain such domains separated by a peptide spacer. Such spacer may be the same as or different from an insulin-like connecting (C) peptide. In another embodiment, a molecule is provided that comprises one or more domains (or functional portion(s) thereof) of an insulin-like protein, and that has one or more mutant (e.g., due to deletion or point mutation(s)) domains of an insulin-like protein (e.g., such that the mutant domain has decreased function).

5.7. GENERATION OF MUTANT PHENOTYPES

The present invention provides for methods of creating genetically-engineered fruit flies and laboratory-generated mutant fruit flies.

5.7.1. GENERATION AND GENETIC ANALYSIS OF DROSOPHILA WITH ALTERED INSULIN-LIKE GENES

In a specific embodiment, genetically-engineered fruit flies are made that harbor one or more deletions or insertions in an insulin-like gene or genes. In another embodiment, genetically-engineered fruit flies harbor interfering RNAs derived from such genes. In another embodiment, genetically-engineered fruit flies harbor one or more transgenes for mis-expression of wild-type or mutant forms of such genes. The invention provides for laboratory-generated mutant fruit flies which contain deletions, insertions, rearrangements, or point mutations in an insulin-like gene or genes, or combinations thereof.

The present invention provides a method by which Drosophila strains with laboratory-generated alterations in insulin-like genes may be used for the identification of insulin-like genes that participate in particular biochemical and/or genetic pathways. In a specific embodiment, Drosophila strains with laboratory-generated alterations in one or more insulin-like genes may be used for the identification of insulin-like genes that participate in biochemical and/or genetic pathways that constitute possible pesticide targets, as judged by phenotypes such as non-viability, block of normal development, defective feeding, defective movement, or defective reproduction. That is, development of such a phenotype in a Drosophila containing an alteration in a Drosophila insulin-like gene indicates that the insulin-like gene is a potential pesticide target.

In another embodiment, Drosophila strains with laboratory-generated alterations relate to therapeutic applications associated with the insulin superfamily hormones, such as metabolic control, growth regulation, differentiation, reproduction, and aging.

In another embodiment, Drosophila strains with laboratory-generated alterations relate to large-scale genetic modifier screens aimed at systematic identification of components of genetic and/or biochemical pathways that serve as novel drug targets, diagnostics, prognostics, therapeutic proteins, pesticide targets or protein pesticides.

The invention provides methods for creating and analyzing Drosophila strains having modified expression of insulin-like genes, as described in the Sections below. In one embodiment, expression modification methods include any method known to one skilled in the art. Specific examples include but are not limited to chemical mutagenesis, transposon mutagenesis, antisense RNA interference, and transgene-mediated mis-expression. In the creation of transgenic animals, it is preferred that heterologous (i.e., non-native) promoters be used to drive transgene expression.

5.7.2. GENERATION OF LOSS-OF-FUNCTION MUTATION IN INSULIN-LIKE GENES

The present invention provides methods of testing for preexisting mutations in a *D. melangaster* insulin-like gene. In a specific embodiment, the genomic sequence containing the entire insulin cluster can be used to determine whether an existing mutant Drosophila line corresponds to a mutation in one or more of the insulin-like genes. Specifically, but not by limitation, mutations in genes that map to the same genetic region as the insulin-like gene cluster (chromosomal band 67C-D) are of particular interest. For example, a large number of previously identified mutations have been mapped to the approximate genetic region of the insulin cluster (67C-D), including but not limited to 1(3)67BDa, 1(3)67BDb, 1(3)67BDc, 1(3)67BDd, 1(3)67BDe, 1(3)67BDf, 1(3)67BDg 1(3)67BDh, 1(3)67BDi 1(3)67BDj, 1(3)67BDk, 1(3)67BDl, 1(3)67BDm, 1(3)67BDn, 1(3)67BDp, 1(3)67BDq, 1(3)67BDr (FlyBase: a Drosophila database, Flybase consortium, Harvard University); however, the normal function of these genes has not been determined. To ascertain whether any of these mutations are in an insulin-like gene, a genomic fragment containing the Drosophila insulin gene cluster and potential flanking regulatory regions can be subclone into any appropriate Drosophila transformation vector, such as the Carnegie series of vectors (Rubin and Spradling, 1983, Nucleic Acids Res. 11(18):6341–51), the pCaspeR series of vectors (Thummel, et al., 1988, Gene 74(2):445–56), or the pW8 vector (Klemenz, et al., 1987, Nucleic Acids Res. 15(10):3947–59) and injected into flies along with an appropriate helper plasmid to supply transposase. Resulting transformants are crossed for complementation testing to an existing panel of Drosophila lines containing mutations that have been mapped to the appropriate genomic region (67C-D) as described above (Greenspan, 1997, in Fly pushing: *The Theory and Practice of Drosophila Genetics* Cold Spring Harbor Press, Plainview, N.Y., pp. 3–46). If a mutant line is discovered to be rescued by this genomic fragment, as judged by complementation of the mutant phenotype, progressively smaller subclones or clones containing a single insulin gene can be individually tested until the responsible locus is identified.

5.7.3. GENERATING LOSS-OF-FUNCTION MUTATIONS BY MUTAGENESIS

Further, the invention herein provides a method for generating loss-of-function mutations in a *D. melangaster* insulin-like gene. Mutations can be generated by one of many mutagenesis methods known to investigators skilled in the art (Ashburner, 1989, In *Drosophila: A Laboratory Manual*, Cold Spring Harbor, N.Y., Cold Spring Harbor Laboratory Press: pp. 299–418.; *"Flypushing: The Theory and Practice of Drosophila Genetics"* Cold Spring Harbor Press, Plainview, N.Y.). In a specific embodiment, the mutagens that can be used include but are not restricted to: transposons such as the P or hobo elements; chemical mutagens such as ethylmethane sulfonate (EMS), methylmethane sulfonate (MMS), N-ethyl-N-nitrosourea (ENU), triethylmelamine, diepoxyalkanes, ICR-170, or formaldehyde; and irradiation with X-rays, gamma rays, or ultraviolet radiation.

Mutagenesis by P elements, or marked P elements, is particularly appropriate for isolation of loss-of-function mutations in Drosophila insulin-like genes due to the precise molecular mapping of these genes, the small size of these targets, the availability and proximity of preexisting P element insertions for use as a localized transposon source, and the potential to knock out several of these genes by induction of a small deletion of the locus (Hamilton and Zinn, 1994, Methods in Cell Biology 44:81–94; Wolfler and Goldberg, 1994, Methods in Cell Biology 44:33–80; Clark, et al., 1994, Proc. Natl. Acad. Sci. U.S.A. 91(2):719–22; Kaiser, 1990, Bioessays 12(6):297–301, In *Drosophila melanogaster: Practical Uses in Cell and Molecular Biology*, L. S. B. Goldstein and E. A. Fyrberg, Eds., Academic Press, Inc. San Diego, Calif.). For the purposes of mutagenesis, modified P elements are typically used which contain one or more of the following elements: sequences encoding a dominant visible marker, usually a wild-type white+ or rosy+ eye color gene, to allow detection of animals containing the P element and to screen for transposition events (Rubin and Spradling, 1982, Science 218(4570):348–53; Klemenz, et al., 1987, Nucleic Acids Res. 15(10):3947–59), bacterial plasmid sequences including a selectable marker such as ampicillin resistance to facilitate cloning of genomic sequences adjacent to the insertion site (Steller and Pirrotta, 1985, Embo. J. 4:167–171) and lacZ sequences fused to a weak general promoter to detect the presence of enhancers with a developmental expression pattern of interest (Bellen, et al., 1989, Genes Dev. 3(9): 1288–300; Bier, et al., 1989, Genes Dev. 3(9):1273–87; Wilson, et al., 1989, Genes Dev. 3(9):1301–13). For examples of marked P elements useful for mutagenesis see "FlyBase—A Drosophila Database", Nucleic Acids Research 26:85–88, (http://flybase.bio.indiana.edu).

A preferred method of transposon mutagenesis employs the "local hopping" method (Tower et al., 1993, Genetics 133:347–359). Briefly, an existing mutant Drosophila line containing a P element inserted into chromosomal bands 67C-D, such as 1(3)01859 or any other P element that maps within this region, is crossed to a Drosophila line expressing transposase in order to mobilize the transposon. Transposition of the P element, which contains a marker gene that typically affects eye color, is determined phenotypically on the basis of eye color change in the resulting progeny. Candidate insertion lines are selected for further analysis on the basis of close linkage of the new insertion to the initial insertion site, which can be determined by standard genetic mapping techniques such as high frequency cosegregation of markers. Each new P insertion line can be tested molecularly for transposition of the P element into the insulin-like gene cluster by assays based on PCR amplification. For each reaction, one PCR primer is used that is homologous to sequences contained within the P element and a second primer is homologous to one of the individual insulin genes, in either the coding region or flanking regions of the insulin-like gene. Products of the PCR reactions are detected by agarose gel electrophoresis. The sizes of the resulting DNA fragments are used to map the site of P element insertion.

Alternatively, Southern blotting and restriction mapping using DNA probes derived from genomic DNA or cDNAs of the insulin-like genes can be used to detect transposition events that rearrange the genomic DNA of the insulin-like genes. P transposition events that map to the insulin gene cluster can be assessed for phenotypic effects in heterozygous or homozygous mutant Drosophila, as described in detail below.

5.7.4. GENERATING LOCALIZED DELETIONS IN THE INSULIN GENE CLUSTER

In another embodiment, Drosophila lines carrying P insertions in the insulin gene cluster can be used to generate localized deletions in the insulin-like gene cluster by previously described methods known in the art (Kaiser, 1990, Bioessays 12(6):297–301; Harnessing the power of Drosophila genetics, In *Drosophila melanogaster: Practical Uses in Cell and Molecular Biology*, L. S. B. Goldstein and E. A. Fyrberb, eds., Academic Press, Inc. San Diego, Calif.). This is particularly useful if no P elements transpositions are found that disrupt a particular insulin-like gene of interest. In brief, flies containing P elements inserted into the insulin gene cluster are exposed to a further round of transposase to induce excision of the element. Progeny in which the transposon has excised are typically identified by loss of the eye color marker associated with the transposable element. The resulting progeny will include flies with either precise or imprecise excision of the P element, where the imprecise excision events often result in deletion of genomic DNA neighboring the site of P insertion. Such progeny can be screened by molecular techniques to identify deletion events that remove flanking genomic sequence. Such methods include, but are not limited to: (a) methods of detecting alterations in the genomic DNA based on PCR amplification with primers flanking the insertion site of the P element; (b) methods based on Southern blotting and restriction mapping using DNA probes derived from the P element, DNA probes derived from flanking genomic sequence in the region of the insulin-like genes, or DNA probes derived from cDNAs of insulin-like genes. Deletions generated in this manner that remove one or more of the insulin-like loci can be assessed for phenotypic effects in heterozygous and homozygous mutant Drosophila as described below.

5.7.5. GENERATING LOSS-OF-FUNCTION PHENOTYPES USING METHODS BASED ON RNA-MEDIATED INTERFERENCE WITH GENE EXPRESSION

The invention further provides a method for generating loss-of-function phenotypes using methods based on RNA-mediated interference with gene expression. The function of the Drosophila insulin-like genes identified herein may be characterized and/or determined by generating loss-of-function phenotypes through such RNA-based methods.

In one embodiment, loss-of-function phenotypes are generated by antisense RNA methods (Schubiger and Edgar, 1994, Methods in Cell Biology 44:697–713). One form of the antisense RNA method involves the injection of embryos with an antisense RNA that is partially homologous to the gene-of-interest (in this case an insulin-like gene). Another form of the antisense RNA method involves expression of an antisense RNA partially homologous to the gene-of-interest by operably joining a portion of the gene-of-interest in the antisense orientation to a powerful promoter that can drive the expression of large quantities of antisense RNA, either generally throughout the animal or in specific tissues. Examples of powerful promoters that can be used in this strategy of antisense RNA include heat shock gene promoters or promoters controlled by potent exogenous transcription factors, such as GAL4 and tTA, described in more detail in the following section. Antisense RNA-generated loss-of-function phenotypes have been reported previously for several Drosophila genes including cactus, pecanex, and Krupple (LaBonne, et al., 1989, Dev. Biol. 136(1):1–16; Schuh and Jackle, 1989, Genome 31(1):422–5; Geisler, et al., 1992, Cell 71(4):613–21; see also Section 5.7 below).

In a second embodiment, loss-of-function phenotypes are generated by cosuppression methods (Bingham, 1997, Cell 90(3):385–7; Smyth, 1997, Curr. Biol. 7(12):793–5; Que and Jorgensen, 1998, Dev. Genet. 22(1):100–9). Cosuppression is a phenomenon of reduced gene expression produced by expression or injection of a sense strand RNA corresponding to a partial segment of the gene-of-interest. Cosuppression effects have been employed extensively in plants to generate loss-of-function phenotypes, and there is report of cosuppression in Drosophila where reduced expression of the Adh gene was induced from a white-Adh transgene (Pal-Bhadra, et al., 1997, Cell 90(3):479–90).

In a third embodiment, loss-of-function phenotypes may be generated by double-stranded RNA interference. This method is based on the interfering properties of double-stranded RNA derived from the coding regions of genes. Termed dsRNAi, this method has proven to be of great utility in genetic studies of the nematode C. elegans (see Fire et al., 1998, Nature 391:806–811). In a preferred embodiment of this method, complementary sense and antisense RNAs derived from a substantial portion of a gene-of-interest, such as an insulin-like gene, are synthesized in vitro. Phagemid DNA templates containing cDNA clones of the gene-of-interest are inserted between opposing promoters for T3 and T7 phage RNA polymerases. Alternatively, one can use PCR products amplified from coding regions of insulin-like genes, where the primers used for the PCR reactions are modified by the addition of phage T3 and T7 promoters. The resulting sense and antisense RNAs are annealed in an injection buffer, and the double-stranded RNA injected or otherwise introduced into animals. Progeny of the injected animals are then inspected for phenotypes-of-interest.

5.7.6. ANTISENSE REGULATION OF GENE EXPRESSION

The invention provides for antisense uses of *D. melangaster* insulin-like genes. In a specific embodiment, an insulin-like protein function is inhibited by use of insulin-like antisense nucleic acids. The present invention provides for use of nucleic acids of at least six nucleotides that are antisense to a gene or cDNA encoding an insulin-like protein or a portion thereof. An insulin-like "antisense" nucleic acid as used herein refers to a nucleic acid capable of hybridizing to a sequence-specific (i.e. non-poly A) portion of an insulin-like RNA (preferably mRNA) by virtue of some sequence complementarily. Antisense nucleic acids may also be referred to as inverse complement nucleic acids. The antisense nucleic acid may be complementary to a coding and/or noncoding region of an insulin-like mRNA. Such antisense nucleic acids have utility in inhibiting an insulin-like protein function. For example, such antisense nucleic acids may be useful as pesticides to eradicate parasites in plants, or in animals such as dogs, horses, and cattle.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous introduced sequences. In a preferred embodiment, the antisense nucleic acids of the invention are double-stranded RNA mentioned previously (see Fire et al., 1998, Nature 391:806–811).

The insulin-like antisense nucleic acids of the invention are preferably oligonucleotides (ranging from 6 to about 50 oligonucleotides). In specific aspects, an oligonucleotide is at least 10 nucleotides, at least 15 nucleotides, at least 100 nucleotides, or at least 200 nucleotides in length. The oligonucleotide can be DNA or RNA or chimeric mixtures or derivatives or modified versions thereof, or single-stranded or double-stranded. The oligonucleotide can be modified at the base moiety, sugar moiety, or phosphate backbone. The oligonucleotide may include other appending groups such as peptides, or agents facilitating transport across the cell membrane (see e.g., Letsinger et al., 1989, Proc. Natl. Acad. Sci. U.S.A. 86:6553–6556; Lemaitre et al., 1987, Proc. Natl. Acad. Sci. U.S.A. 84:648–652; PCT Publication No. WO 88/09810, published Dec. 15, 1988) or the blood-brain barrier (see e.g., PCT Publication No. WO 89/10134, published Apr. 25, 1988), hybridization-triggered cleavage agents (see e.g., Krol et al., 1988, BioTechniques 6:958–976) or intercalating agents (see e.g., Zon, 1988, Pharm. Res. 5:539–549).

In a preferred aspect of the invention, an insulin-like antisense oligonucleotide is provided as single-stranded DNA. In another preferred aspect, such an oligonucleotide comprises a sequence antisense to the sequence encoding a B peptide domain or an A peptide domain of an insulin-like protein. The oligonucleotide may be modified at any position on its structure with substituents generally known in the art.

The insulin-like antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an a-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide may be conjugated to another molecule, e.g., a peptide, a hybridization-triggered cross-linking agent, a transport agent, a hybridization-triggered cleavage agent, etc.

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (Stein et al., 1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

In a specific embodiment, an insulin-like antisense oligonucleotide comprises catalytic RNA, or a ribozyme (see e.g., PCT Publication WO 90/11364, published Oct. 4, 1990; Sarver et al., 1990, Science 247:1222–1225). In another embodiment, the oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

In an alternative embodiment, the insulin-like antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the insulin-like antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the insulin-like antisense RNA can be by any promoter known in the art. Such promoters can be inducible or constitutive. Such promoters include but are not limited to: the SV40 early promoter region (Benoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

The antisense nucleic acids of the invention comprise a sequence complementary to at least a sequence-specific portion of an RNA transcript of an insulin-like gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded insulin-like antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an insulin-like RNA it may contain and still form a stable duplex (or triplex, as the case may be). One skilled in the art can ascertain a tolerable degree of mismatch by use of standard procedures to determine, e.g., the melting point of the hybridized complex.

5.7.7. GENERATING GAIN-OF-FUNCTION PHENOTYPES BY ECTOPIC EXPRESSION OF INSULIN-LIKE GENES

The current invention provides methods for generating gain-of-function phenotypes by ectopic expression of insulin-like genes. Ectopic expression, including misexpression or overexpression, of wild type or altered Drosophila insulin-like genes in transgenic animals is another useful method for the analysis of gene function (Brand, et al., 1994, Methods in Cell Biology 44:635–654, Ectopic expression in Drosophila; Hay, et al., 1997, Proc. Natl. Acad. Sci. U.S.A. 94(10):5195–200). Such transgenic Drosophila may be created that contain gene fusions of the coding regions of insulin-like genes (from either genomic DNA or cDNA) operably joined to a specific promoter and transcriptional enhancer whose regulation has preferably been well characterized, preferably heterologous promoters/enhancers that do not normally drive the expression of the insulin-like genes. Examples of promoters/enhancers that can be used to drive such misexpression of insulin-like genes include, but are not limited to, the heat shock promoters/enhancers from the hsp70 and hsp83 genes, useful for temperature induced expression; tissue specific promoters/enhancers such as the sevenless promoter/enhancer (Bowtell, et al., 1988, Genes Dev. 2(6):620–34), the eyeless promoter/enhancer (Bowtell, et al., 1991, Proc. Natl. Acad. Sci. U.S.A. 88(15):6853–7), and glass-responsive promoters/enhancers (Quiring, et al., 1994, Science 265:785–9) useful for expression in the eye; enhancers/promoters derived from the dpp or vetigal genes useful for expression in the wing (Staehling-Hampton, et al., 1994, Cell Growth Differ. 5(6):585–93; Kim, et al., 1996, Nature 382:133–8) and binary control systems employing exogenous DNA regulatory elements and exogenous transcriptional activator proteins, useful for testing the misexpression of genes in a wide variety of developmental stage-specific and tissue-specific patterns. Two examples of binary exogenous regulatory systems include the UAS/GAL4 system from yeast (Hay, et al., 1997, Proc. Natl. Acad. Sci. U.S.A. 94(10):5195–200; Ellis, et al., 1993, Development 119(3):855–65) and the "Tet system" derived from *E. coli*, which are described below. It is readily apparent to those skilled in the art that additional binary systems can be used which are based on other sets of exogenous transcriptional activators and cognate DNA regulatory elements in a manner similar to that for the UAS/GAL4 system and the Tet system.

In a specific embodiment, the UAS/GAL4 system is used. This system is a well-established and powerful method of mis-expression in Drosophila which employs the $UAS_G$ upstream regulatory sequence for control of promoters by the yeast GAL4 transcriptional activator protein (Brand and Perrimon, 1993, Development 11 8(2):401–15). In this approach, transgenic Drosophila, termed "target" lines, are generated where the gene-of-interest (e.g. an insulin-like gene) to be mis-expressed is operably fused to an appropriate promoter controlled by $UAS_G$. Other transgenic Drosophila strains, termed "driver" lines, are generated where the GAL4 coding region is operably fused to promoters/enhancers that direct the expression of the GAL4 activator protein in specific tissues, such as the eye, wing, nervous system, gut, or musculature. The gene-of-interest is not expressed in the so-called target lines for lack of a transcriptional activator to "drive" transcription from the promoter joined to the gene-of-interest. However, when the UAS-target line is crossed with a GAL4 driver line, mis-expression of the gene-of-interest is induced in resulting progeny in a specific pattern that is characteristic for that GAL4 line. The technical simplicity of this approach makes it possible to sample the effects of directed mis-expression of the gene-of-interest in a wide variety of tissues by generating one transgenic target line with the gene-of-interest, and crossing that target line with a panel of pre-existing driver lines. A very large number of specific GAL4 driver lines have been generated previously and are available for use with this system.

In a second embodiment, a related method of directed mis-expression in Drosophila is used, that makes use of a tetracycline-regulated gene expression from *E. coli*, referred to as the "Tet system". In this case, transgenic Drosophila driver lines are generated where the coding region for a tetracycline-controlled transcriptional activator (tTA) is operably fused to promoters/enhancers that direct the expression of tTA in a tissue-specific and/or developmental stage-specific manner. Also, transgenic Drosophila target lines are generated where the coding region for the gene-of-interest to be mis-expressed (e.g. an insulin-like gene) is operably fused to a promoter that possesses a tTA-responsive regulatory element. Here again, mis-expression of the gene-of-interest can be induced in progeny from a cross of the target line with any driver line of interest; moreover, the use of the Tet system as a binary control mechanism allows for an additional level of tight control in the resulting progeny of this cross. When Drosophila food is supplemented with a sufficient amount of tetracycline, it completely blocks expression of the gene-of-interest in the resulting progeny. Expression of the gene-of-interest can be induced at will simply by removal of tetracycline from the food. Also, the level of expression of the gene-of-interest can be adjusted by varying the level of tetracycline in the food. Thus, the use of the Tet system as a binary control mechanism for mis-expression has the advantage of providing a means to control the amplitude and timing of mis-expression of the gene-of-interest, in addition to spatial control. Consequently, if a gene-of-interest (e.g. an insulin-like gene) has lethal or deleterious effects when mis-expressed at an early stage in development, such as the embryonic or larval stages, the function of the gene-of-interest in the adult can still be assessed using the Tet system, by adding tetracycline to the food during early stages of development and removing tetracycline later so as to induce mis-expression only at the adult stage.

5.8. ANALYSIS OF MUTANT PHENOTYPES

After isolation of fruit flies carrying mutated or mis-expressed insulin-like genes, or inhibitory RNAs, animals are carefully examined for phenotypes-of-interest. For the situations involving deletions, insertions, point mutations, or mis-expression of insulin-like genes, fruit flies are generated that are homozygous and heterozygous for the altered insulin-like genes.

Examples of specific phenotypes that may be investigated include but are not limited to: altered body shape, altered body size, lethality, sterility, reduced brood size, increased brood size, altered life span, defective locomotion, alterted body plan, altered cell size, increased cell division, decreased cell division, altered feeding, slowed development, increased development, altered metabolism, (such as altered glycogen synthesis, storage, or degradation; altered lipid synthesis, storage or degradation; altered levels of carbohydrate in the hemolymph; and altered levels of lipid in the hemolymph), and altered morphogenesis of specific organs and tissues such as gonad, nervous system, fat body, hemocytes, peripheral sensory organs, bristles, imaginal discs, eye, wing, leg, antennae, gut, or musculature. For example, it is of particular interest to identify the ligand or ligands responsible for activating InR (or DIR), a Drosophila homologue of the insulin receptor. A likely phenotype of a loss-of-function mutation in the ligand for the InR receptor might resemble one or more of the identified loss of function phenotypes for the receptor itself, including reduced body size and weight, reduced female fertility, increased developmental time, and/or defective embryonic neurogenesis.

Methods for creation and analysis of transgenic Drosophila strains having modified expression of genes are well known to those skilled in the art (Brand, et al., 1994, Methods in Cell Biology 44:635–654; Hay, et al., 1997, Proc. Natl. Acad. Sci. USA 94(10):5195–200). cDNAs or genomic regions encoding normal or mutant insulin-like genes can be operably fused to a desired promoter, as described above, and the promoter-insulin-like gene fusion inserted into any appropriate Drosophila transformation vector for the generation of transgenic flies. Typically, such transformation vectors are based on a well-characterized transposable elements, for example the P element (Rubin and Spradling, 1982, Science 218:348–53), the hobo element (Blackman, et al., 1989, Embo J. 8(l):211–7), mariner element (Lidholn, et al., 1993, Genetics 134(3):859–68), the hermes element (O'Brochta, et al., 1996, Genetics 142(3):907–14), Minos (Loukeris, et al., 1995, Proc. Natl. Acad. Sci. USA 92(21):9485–9), or the PiggyBac element (Handler, et al., 1998, Proc. Natl. Acad. Sci. USA 95(13):7520–5), where the terminal repeat sequences of the transposon that are required for transposition are incorporated into the transformation vector and arranged such that the terminal repeat sequences flank the transgene of interest (in this case a promoter-insulin-like gene fusion) as well as a marker gene used to identify transgenic animals. Most often, marker genes are used that affect the eye color of Drosophila, such as derivatives of the Drosophila white or rosy genes; however, in principle, any gene can be used as a marker that causes a reliable and easily scored phenotypic change in transgenic animals, and examples of other marker genes used for transformation include the $Adh^+$ gene used as a selectable marker for the transformation of $Adh^-$ strains, $Ddc+$ gene used to transform $Ddc^{ts2}$ mutant strains, the lacZ gene of *E. coli*, and the $neomycin^R$ gene from the *E. coli* transposon Tn5. Plasmid constructs for introduction of the desired transgene are coinjected into Drosophila embryos having an appropriate genetic background, along with a helper plasmid that expresses the specific transposase need to mobilized the transgene into the genomic DNA. Animals arising from the injected embryos (G0 adults) are selected, or screened manually, for transgenic mosaic animals based on expression of the marker gene phenotype and are subsequently crossed to generate fully transgenic animals (G1 and subsequent generations) that will stably carry one or more copies of the transgene of interest. Such stable transgenic animals are inspected for mutant phenotypes, such as abnormal development, morphology, metabolism, growth, longevity, reproduction, viability, or behavior, in order to determine a function for the insulin-like gene created by ectopic expression or overexpression of the insulin-like gene, or by expression of mutant insulin-like genes.

Generation of an overexpression/mis-expression phenotype is likely to result from either activation or inhibition of a receptor-linked signaling pathway. If such an overexpression/mis-expression phenotype is defined for an insulin-like gene, clonal analysis can then be used to determine whether this phenotype is restricted to cells expressing the insulin-like gene (i.e. whether the phenotype is cell autonomous or cell non-autonomous). Methods of mitotic recombination of chromosomes in heterozygous flies can be used to generate mitotic clones of genetically homozygous cells that are well known to those skilled in the art, which include the use of X-rays or preferably FLP/FRT mediated recombination (Xu and Harrison, 1994, Methods in Cell Biology 44:655–681; Greenspan, 1979, In *Fly Pushing: The Theory and Practice of Drosophila Genetics*. Plainview, N.Y., Cold Spring Harbor Laboratory Press: pp. 103–124). These mitotic recombination techniques result in patches of cells, mitotic clones, that contain 2 or no copies of the gene-of-interest. Production of the overexpression/mis-expression phenotype within cells in a clone having no copies of the gene-of-interest indicates that the effect is not cell autonomous, and is therefore likely to be the effect of a secreted molecule, as might be expected for insulin-like molecules.

5.9. IDENTIFICATION OF COMPOUNDS WITH BINDING CAPACITY

This invention provides screening methodologies useful in the identification of proteins and other compounds which bind to, or otherwise directly interact with, the *D. melanogaster* insulin-like genes and proteins. Screening methodologies are well known in the art (see e.g., PCT International Publication No. WO 96/34099, published Oct. 31, 1996, which is incorporated by reference herein in its entirety). The proteins and compounds include endogenous cellular components which interact with the identified genes and proteins in vivo and which, therefore, may provide new targets for pharmaceutical and therapeutic interventions, as well as recombinant, synthetic, and otherwise exogenous compounds which may have binding capacity and, therefore, may be candidates for pharmaceutical agents. Thus, in one series of embodiments, cell lysates or tissue homogenates may be screened for proteins or other compounds which bind to one of the normal or mutant *D. melangaster* insulin-like genes and proteins.

Alternatively, any of a variety of exogenous compounds, both naturally occurring and/or synthetic (e.g., libraries of small molecules or peptides), may be screened for binding capacity.

As will be apparent to one of ordinary skill in the art, there are numerous other methods of screening individual proteins or other compounds, as well as large libraries of proteins or other compounds (e.g., phage display libraries) to identify molecules which bind to *D. melangaster* insulin-like proteins. All of these methods comprise the step of mixing a *D. melangaster* insulin-like protein or fragment with test compounds, allowing time for any binding to occur, and assaying for any bound complexes. All such methods are enabled by the present disclosure of substantially pure *D. melanogaster* insulin-like proteins, substantially pure functional domain fragments, fusion proteins, antibodies, and methods of making and using the same.

5.9.1. PROTEINS WHICH INTERACT WITH INSULIN-LIKE PROTEINS

The present invention further provides methods of identifying or screening for proteins which interact with *D. melangaster* insulin-like proteins, or derivatives, fragments or analogs thereof. In specific embodiments, the method of identifying a molecule that binds to a ligand comprises contacting the ligand with a plurality of molecules under conditions conducive to binding between the ligand and the molecules; and identifying a molecule within the plurality that binds to the ligand. The ligand or protein in the method can either be a purified or non-purified form. Preferably, the method of identifying or screening is a yeast two-hybrid assay system or a variation thereof, as further described below. In this regard, the yeast two-hybrid method has been used to analyze IGF-1-receptor interactions (see Zhu and Kahn, 1997, Proc. Natl. Acad. Sci. U.S.A. 94:13063–13068). Derivatives (e.g., fragments) and analogs of a protein can also be assayed for binding to a binding partner by any method known in the art, for example, immunoprecipitation with an antibody that binds to the protein in a complex followed by analysis by size fractionation of the immunoprecipitated proteins (e.g., by denaturing or nondenaturing polyacrylamide gel electrophoresis), Western analysis, non-denaturing gel electrophoresis, etc.

One aspect of the present invention provides methods for assaying and screening fragments, derivatives and analogs of *D. melangaster* insulin-like proteins for interacting proteins (for binding to a *D. melangaster* insulin-like peptide). Derivatives, analogs and fragments of proteins that interact with a *D. melangaster* insulin-like protein care preferably identified by means of a yeast two hybrid assay system (Fields and Song, 1989, Nature 340:245–246; U.S. Pat. No. 5,283,173). Because the interactions are screened for in yeast, the intermolecular protein interactions detected in this system occur under physiological conditions that mimic the conditions in eukaryotic cells, including vertebrates or invertebrates (Chien et al., 1991, Proc. Natl. Acad. Sci. U.S.A. 88:9578–9581). This feature facilitates identification of proteins capable of interaction with a *D. melanogaster* insulin-like protein from species other than *D. melanogaster*.

Identification of interacting proteins by the improved yeast two-hybrid system is based upon the detection of expression of a reporter gene, the transcription of which is dependent upon the reconstitution of a transcriptional regulator by the interaction of two proteins, each fused to one half of the transcriptional regulator. The "bait" (i.e., *D. melanogaster* insulin-like protein or derivative or analog thereof) and "prey" (proteins to be tested for ability to interact with the bait) proteins are expressed as fusion proteins to a DNA binding domain, and to a transcriptional regulatory domain, respectively, or vice versa. In various specific embodiments, the prey has a complexity of at least about 50, about 100, about 500, about 1,000, about 5,000, about 10,000, or about 50,000; or has a complexity in the range of about 25 to about 100,000, about 100 to about 100,000, about 50,000 to about 100,000, or about 100,000 to about 500,000. For example, the prey population can be one or more nucleic acids encoding mutants of a protein (e.g., as generated by site-directed mutagenesis or another method of making mutations in a nucleotide sequence). Preferably, the prey populations are proteins encoded by DNA, e.g., cDNA or genomic DNA or synthetically-generated DNA. For example, the populations can be expressed from chimeric genes comprising cDNA sequences from an un-characterized sample of a population of cDNA from mRNA.

One characteristic of the yeast two-hybrid system is that proteins examined in this system are expressed as cytoplasmic proteins, and therefore do not pass through the secretory pathway. The insulin-like proteins of the present invention are predicted to be secreted proteins which normally undergo protein processing during trafficking leading to the removal of certain domains such as the C-domain and the signal peptide, and therefore expression of precursor forms of Drosophila insulin-like proteins in the yeast two-hybrid system does not lead to the removal of such domains. However, several methods are incorporated in the present invention to examine derivatives of insulin-like proteins that mimic processed forms of these proteins. By way of example, but not limitation, in one embodiment, the insulin-like protein that is examined in the yeast two-hybrid system is expressed as a modified form containing the C-peptide but lacking the signal peptide (Zhu and Kahn, 1997, Proc. Natl. Acad. Sci. U.S.A. 94(24):13063–68). In a second example and embodiment, the insulin-like protein that is examined in the yeast two-hybrid system is a modified "mini-insulin" that lacks both the signal peptide and the C-peptide domains where the C peptide is replaced with a short sequence, such as a reverse turn, which promotes proper folding and activity of the mini-insulin (Chang, et al., 1998, Biochem J. 329:631–5).

In a specific embodiment, recombinant biological libraries expressing random peptides can be used as the source of prey nucleic acids.

In another embodiment, the invention provides methods of screening for inhibitors or enhancers of the protein interactants identified herein. Briefly, the protein-protein interaction assay can be carried out as described herein, except that it is done in the presence of one or more candidate molecules. An increase or decrease in reporter gene activity relative to that present when the one or more candidate molecules are absent indicates that the candidate molecule has an effect on the interacting pair. In a preferred method, inhibition of the interaction is selected for (i.e., inhibition of the interaction is necessary for the cells to survive), for example, where the interaction activates the URA3 gene, causing yeast to die in medium containing the chemical 5-fluoroorotic acid (Rothstein, 1983, Meth. Enzymol. 101:167–180). The identification of inhibitors of such interactions can also be accomplished, for example, but not by way of limitation, using competitive inhibitor assays, as described above.

In general, proteins of the bait and prey populations are provided as fusion (chimeric) proteins (preferably by recombinant expression of a chimeric coding sequence) comprising each protein contiguous to a pre-selected sequence. For one population, the pre-selected sequence is a DNA binding domain. The DNA binding domain can be any DNA binding domain, as long as it specifically recognizes a DNA sequence within a promoter. For example, the DNA binding domain is of a transcriptional activator or inhibitor. For the other population, the pre-selected sequence is an activator or inhibitor domain of a transcriptional activator or inhibitor, respectively. The regulatory domain alone (not as a fusion to a protein sequence) and the DNA-binding domain alone (not as a fusion to a protein sequence) preferably do not detectably interact (so as to avoid false positives in the assay). The assay system further includes a reporter gene operably linked to a promoter that contains a binding site for the DNA binding domain of the transcriptional activator (or inhibitor).

Accordingly, in the present method of the invention, binding of a D. melanogaster insulin-like fusion protein to a prey fusion protein leads to reconstitution of a transcriptional activator (or inhibitor) which activates (or inhibits) expression of the reporter gene. The activation (or inhibition) of transcription of the reporter gene occurs intracellularly, e.g., in prokaryotic or eukaryotic cells, preferably in cell culture.

The promoter that is operably linked to the reporter gene nucleotide sequence can be a native or non-native promoter of the nucleotide sequence, and the DNA binding site(s) that are recognized by the DNA binding domain portion of the fusion protein can be native to the promoter (if the promoter normally contains such binding site(s)) or non-native to the promoter. Thus, for example, one or more tandem copies (e.g. four or five copies) of the appropriate DNA binding site can be introduced upstream of the TATA box in the desired promoter (e.g., in the area of about position –100 to about –400). In a preferred aspect, 4 or 5 tandem copies of the 17 bp UAS (GAL4 DNA binding site) are introduced upstream of the TATA box in the desired promoter, which is upstream of the desired coding sequence for a selectable or detectable marker. In a preferred embodiment, the GAL1–10 promoter is operably fused to the desired nucleotide sequence; the GAL1–10 promoter already contains 4 binding sites for GAL4.

Alternatively, the transcriptional activation binding site of the desired gene(s) can be deleted and replaced with GAL4 binding sites cartel et al., 1993, BioTechniques 14:920–924; Chasman et al., 1989, Mol. Cell. Biol. 9:4746–4749). The reporter gene preferably contains the sequence encoding a detectable or selectable marker, the expression of which is regulated by the transcriptional activator, such that the marker is either turned on or off in the cell in response to the presence of a specific interaction. Preferably, the assay is carried out in the absence of background levels of the transcriptional activator (e.g., in a cell that is mutant or otherwise lacking in the transcriptional activator).

In one embodiment, more than one reporter gene is used to detect transcriptional activation, e g., one reporter gene encoding a detectable marker and one or more reporter genes encoding different selectable markers. The detectable marker can be any molecule that can give rise to a detectable signal, e.g. a fluorescent protein or a protein that can be readily visualized or that is recognizable by a specific antibody. The selectable marker can be any protein molecule that confers the ability to grow under conditions that do not support the growth of cells not expressing the selectable marker, e.g., the selectable marker is an enzyme that provides an essential nutrient and the cell in which the interaction assay occurs is deficient in the enzyme and the selection medium lacks such nutrient. The reporter gene can either be under the control of the native promoter that naturally contains a binding site for the DNA binding protein, or under the control of a heterologous or synthetic promoter.

The activation domain and DNA binding domain used in the assay can be from a wide variety of transcriptional activator proteins, as long as these transcriptional activators have separable binding and transcriptional activation domains. For example, the GAL4 protein of S. cerevisiae (Ma et al., 1987, Cell 48:847–853), the GCN4 protein of S. cerevisiae (Hope and Struhl, 1986, Cell 46:885–894), the ARD1 protein of S. cerevisiae (Thukral et al., 1989, Mol. Cell. Biol. 9:2360–2369), and the human estrogen receptor (Kumar et al., 1987, Cell 51:941–951), have separable DNA binding and activation domains. The DNA binding domain and activation domain that are employed in the fusion proteins need not be from the same transcriptional activator. In a specific embodiment, a GAL4 or LEXA DNA binding domain is employed. In another specific embodiment, a GAL4 or herpes simplex virus VP16 (Triezenberg et al., 1988, Genes Dev. 2:730–742) activation domain is employed. In a specific embodiment, amino acids 1–147 of GAL4 (Ma et al., 1987, Cell 48:847–853; Ptashne et al., 1990, Nature 346:329–331) is the DNA binding domain, and amino acids 411–455 of VP16 (Triezenberg et al., 1988, Genes Dev. 2:730–742; Cress et al., 1991, Science 251:87–90) comprise the activation domain.

In a preferred embodiment, the yeast transcription factor GAL4 is reconstituted by protein-protein interaction and the host strain is mutant for GAL4. In another embodiment, the DNA-binding domain is Ace1N and/or the activation domain is Ace1, the DNA binding and activation domains of the Ace1 protein, respectively. Ace1 is a yeast protein that activates transcription from the CUP1 operon in the presence of divalent copper. CUP1 encodes metallothionein, which chelates copper, and the expression of CUP1 protein allows growth in the presence of copper, which is otherwise toxic to the host cells. The reporter gene can also be a CUP1-lacZ fusion that expresses the enzyme beta-galactosidase (detectable by routine chromogenic assay) upon binding of a reconstituted Ace1N transcriptional activator (see Chaudhuri et al., 1995, FEBS Letters 357:221–226). In another specific embodiment, the DNA binding domain of the human estrogen receptor is used, with a reporter gene driven by one or three estrogen receptor response elements (Le Douarin et al., 1995, Nucl. Acids. Res. 23:876–878).

The DNA binding domain and the transcriptional activator/inhibitor domain each preferably has a nuclear localization signal (see Ylikomi et al., 1992, EMBO J. 11:3681–3694; Dingwall and Laskey, 1991, TIBS 16:479–481) functional in the cell in which the fusion proteins are to be expressed.

To facilitate isolation of the encoded proteins, the fusion constructs can further contain sequences encoding affinity tags such as glutathione-S-transferase or maltose-binding protein or an epitope of an available antibody, for affinity purification (e.g., binding to glutathione, maltose, or a particular antibody specific for the epitope, respectively) (Allen et al., 1995, TIBS 20:511–516). In another embodiment, the fusion constructs further comprise bacterial promoter sequences for recombinant production of the fusion protein in bacterial cells.

The host cell in which the interaction assay occurs can be any cell, prokaryotic or eukaryotic, in which transcription of the reporter gene can occur and be detected, including, but not limited to, mammalian (e.g., monkey, mouse, rat, human, bovine), chicken, bacterial, or insect cells, and is preferably a yeast cell. Expression constructs encoding and capable of expressing the binding domain fusion proteins, the transcriptional activation domain fusion proteins, and the reporter gene product(s) are provided within the host cell, by mating of cells containing the expression constructs, or by cell fusion, transformation, electroporation, microinjection, etc. In a specific embodiment in which the assay is carried out in mammalian cells (e.g., hamster cells, HeLa cells), the DNA binding domain is the GAL4 DNA binding domain, the activation domain is the herpes simplex virus VP16 transcriptional activation domain, and the reporter gene contains the desired coding sequence operably linked to a minimal promoter element from the adenovirus E1B gene driven by several GAL4 DNA binding sites (see Fearon et al., 1992, Proc. Natl. Acad. Sci. U.S.A. 89:7958–7962). The host cell used should not express an endogenous transcription factor that binds to the same DNA site as that recognized by the DNA binding domain fusion population. Also, preferably, the host cell is mutant or otherwise lacking in an endogenous, functional form of the reporter gene(s) used in the assay. Various vectors and host strains for expression of the two fusion protein populations in yeast are known and can be used (see e.g., U.S. Pat. No. 5,1468,614; Bartel et al., 1993, "Using the two-hybrid system to detect protein-protein interactions" In *Cellular Interactions in Development*, Hartley, ed., Practical Approach Series xviii, IRL Press at Oxford University Press, New York, N.Y., pp. 153–179; Fields and Sternglanz, 1994, Trends In Genetics 10:286–292). By way of example but not limitation, yeast strains or derivative strains made therefrom, which can be used are N105, N106, N1051, N1061, and YULH. Other exemplary strains that can be used in the assay of the invention also include, but are not limited to, the following:

Y190: MATa, ura3-52, his3-200, lys2-801, ade2-101, trp1-901, leu2-3,112, gal4α, gal80α, cyh$^r$2, LYS2::GAL1$_{UAS}$-HIS3$_{TATA}$HIS3, URA3::GAL1$_{UAS}$-GAL1$_{TATA}$-lacZ; Harper et al., 1993, Cell 75:805–816, available from Clontech, Palo Alto, Calif. Y190 contains HIS3 and lacZ reporter genes driven by GAL4 binding sites.

CG-1945: MATa, ura3-52, his3-200, lys2-801, ade2-101, trp1-901, leu2-3,112, gal4-542, gal80-538, cyh$^r$2, LYS2::GAL1$_{UAS}$-HIS3$_{TATA}$HIS3, URA3::GAL1$_{UAS17mers(×3)}$-CYC1$_{TATA}$-lacZ, available from Clontech, Palo Alto, Calif. CG-1945 contains HIS3 and lacZ reporter genes driven by GAL4 binding sites.

Y187: MAT-α, ura3-52, his3-200, ade2-101, trp1-901, leu2-3,112, gal4α, gal80α, URA3::GAL1$_{UAS}$-GAL1$_{TATA}$-lacZ, available from Clontech, Palo Alto, Calif. Y187 contains a lacZ reporter gene driven by GAL4 binding sites.

SFY526: MATa, ura3-52, his3-200, lys2-801, ade2-101, trp1-901, leu2-3,112, gal4-542, gal80-538, can$^r$, URA3::GAL1-lacZ, available from Clontech, Palo Alto, Calif. SFY526 contains HIS3 and lacZ reporter genes driven by GAL4 binding sites.

HF7c: MATa, ura3-52, his3-200, lys2-801, ade2-101, trp1-901, leu2-3,112, gal4-542, gal80-538, LYS2::GAL1-HIS3, URA3:: GAL1$_{UAS17MERS(×3)}$-CYC1-laCZ, available from Clontech, Palo Alto, Calif. HF7c contains HIS3 and lacZ reporter genes driven by GAL4 binding sites.

YRG-2: MATa, ura3–52, his3–200, lys2–801, ade2–101, trp1-901, leu2-3,112, gal4-542, gal80-538, LYS2::GAL1$_{UAS}$-GAL1$_{TATA}$-HIS3, URA3::GAL1$_{UAS17mers(×3)}$-CYC1-lacZ, available from Stratagene, La Jolla, Calif. YRG-2 contains HIS3 and lacZ reporter genes driven by GAL4 binding sites. Many other strains commonly known and available in the art can be used.

If not already lacking in endogenous reporter gene activity, cells mutant in the reporter gene may be selected by known methods, or the cells can be made mutant in the target reporter gene by known gene-disruption methods prior to introducing the reporter gene (Rothstein, 1983, Meth. Enzymol. 101:202–211).

In a specific embodiment, plasmids encoding the different fusion protein populations can be introduced simultaneously into a single host cell (e.g., a haploid yeast cell) containing one or more reporter genes, by co-transformation, to conduct the assay for protein-protein interactions. Or, preferably, the two fusion protein populations are introduced into a single cell either by mating (e.g., for yeast cells) or cell fusions (e.g., of mammalian cells). In a mating type assay, conjugation of haploid yeast cells of opposite mating type that have been transformed with a binding domain fusion expression construct (preferably a plasmid) and an activation (or inhibitor) domain fusion expression construct (preferably a plasmid), respectively, will deliver both constructs into the same diploid cell. The mating type of a yeast strain may be manipulated by transformation with the HO gene (Herskowitz and Jensen, 1991, Meth. Enzymol. 194:132–146).

In a preferred embodiment, a yeast interaction mating assay is employed using two different types of host cells, strain-type a and alpha of the yeast *Saccharomyces cerevisiae*. The host cell preferably contains at least two reporter genes, each with one or more binding sites for the DNA-binding domain (e.g., of a transcriptional activator). The activator domain and DNA binding domain are each parts of chimeric proteins formed from the two respective populations of proteins. One strain of host cells, for example the a strain, contains fusions of the library of nucleotide sequences with the DNA-binding domain of a transcriptional activator, such as GAL4. The hybrid proteins expressed in this set of host cells are capable of recognizing the DNA-binding site in the promoter or enhancer region in the reporter gene construct. The second set of yeast host cells, for example, the alpha strain, contains nucleotide sequences encoding fusions of a library of DNA sequences fused to the activation domain of a transcriptional activator.

In a preferred embodiment, the fusion protein constructs are introduced into the host cell as a set of plasmids. These plasmids are preferably capable of autonomous replication in a host yeast cell and preferably can also be propagated in *E. coli*. The plasmid contains a promoter directing the transcription of the DNA binding or activation domain fusion genes, and a transcriptional termination signal. The plasmid also preferably contains a selectable marker gene, permitting selection of cells containing the plasmid. The plasmid can be single-copy or multi-copy. Single-copy yeast plasmids that have the yeast centromere may also be used to express the activation and DNA binding domain fusions (Elledge et al., 1988, Gene 70:303–312).

In another embodiment, the fusion constructs are introduced directly into the yeast chromosome via homologous recombination. The homologous recombination for these purposes is mediated through yeast sequences that are not essential for vegetative growth of yeast, e.g., the MER2, MER1, ZIPI, REC102, or ME14 gene.

Bacteriophage vectors can also be used to express the DNA binding domain and/or activation domain fusion proteins. Libraries can generally be prepared faster and more easily from bacteriophage vectors than from plasmid vectors.

In a specific embodiment, the present invention provides a method of detecting one or more protein-protein interactions comprising (a) recombinantly expressing a *D. melangaster* insulin-like protein or a derivative or analog thereof in a first population of yeast cells being of a first mating type and comprising a first fusion protein containing the *D. melangaster* insulin-like sequence and a DNA binding domain, wherein said first population of yeast cells contains a first nucleotide sequence operably linked to a promoter driven by one or more DNA binding sites recognized by said DNA binding domain such that an interaction of said first fusion protein with a second fusion protein, said second fusion protein comprising a transcriptional activation domain, results in increased transcription of said first nucleotide sequence; (b) recombinantly expressing in a second population of yeast cells of a second mating type different from said first mating type, a plurality of said second fusion proteins, each second fusion protein comprising a sequence of a fragment, derivative or analog of a protein and an activation domain of a transcriptional activator, in which the activation domain is the same in each said second fusion protein; (c) mating said first population of yeast cells with said second population of yeast cells to form a third population of diploid yeast cells, wherein said third population of diploid yeast cells contains a second nucleotide sequence operably linked to a promoter driven by a DNA binding site recognized by said DNA binding domain such that an interaction of a first fusion protein with a second fusion protein results in increased transcription of said second nucleotide sequence, in which the first and second nucleotide sequences can be the same or different; and (d) detecting said increased transcription of said first and/or second nucleotide sequence, thereby detecting an interaction between a first fusion protein and a second fusion protein. In a preferred aspect, between step (a) and (b), a step is carried out of negatively selecting to eliminate those yeast cells in said first population which said increased transcription of said first nucleotide sequence occurs in the absence of said second fusion protein (see e.g. PCT International Publication No. WO97/47763, published Dec. 18, 1997, which is incorporated by reference herein in its entirety).

In a preferred embodiment, the bait *D. melangaster* insulin-like sequence and the prey library of chimeric genes are combined by mating the two yeast strains on solid media, such that the resulting diploids contain both kinds of chimeric genes, i.e., the DNA-binding domain fusion and the activation domain fusion.

Preferred reporter genes include the URA3, HIS3 and/or the lacZ genes (see e.g., Rose and Botstein, 1983, Meth. Enzymol. 101:167–180) operably linked to GAL4 DNA-binding domain recognition elements. Other reporter genes include but are not limited to, Green Fluorescent Protein (GFP) (Cubitt et al., 1995, Trends Biochem. Sci. 20:448–455), luciferase, LEU2, LYS2, ADE2, TRP1, CAN1, CYH2, GUS, CUP1 or chloramphenicol acetyl transferase (CAT). Expression of the reporter genes can be detected by techniques known in the art (see e.g. PCT International Publication No. WO97/47763, published Dec. 18, 1997, which is incorporated by reference herein in its entirety).

In a specific embodiment, transcription of the reporter gene is detected by a linked replication assay. For example, as described by Vasavada et al., 1991, Proc. Natl. Acad. Sci. U.S.A. 88:10686–10690, expression of SV40 large T antigen is under the control of the E1B promoter responsive to GAL4 binding sites. The replication of a plasmid containing the SV40 origin of replication, indicates a protein-protein interaction. Alternatively, a polyoma virus replicon can be used (Vasavada et al., 1991, Proc. Natl. Acad. Sci. U.S.A. 88:10686–90).

In another embodiment, the expression of reporter genes that encode proteins can be detected by immunoassay, i.e., by detecting the immunospecific binding of an antibody to such protein, which antibody can be labeled, or incubated with a labeled binding partner to the antibody, to yield a detectable signal. Alam and Cook disclose non-limiting examples of detectable marker genes that can be operably linked to a transcriptional regulatory region responsive to a reconstituted transcriptional activator, and thus used as reporter genes (Alam and Cook, 1990, Anal. Biochem. 188:245–254).

The activation of reporter genes like URA3 or HIS3 enables the cells to grow in the absence of uracil or histidine, respectively, and hence serves as a selectable marker. Thus, after mating, the cells exhibiting protein-protein interactions are selected by the ability to grow in media lacking a nutritional component, such as uracil or histidine (see Le Douarin et al., 1995, Nucl. Acids Res. 23:876–878; Durfee et al., 1993, Genes Dev. 7:555–569; Pierrat et al., 1992, Gene 119:237–245; Wolcott et al., 1966, Biochem. Biophys. Acta 122:532–534). In other embodiments of the present invention, the activities of the reporter genes like GFP or lacZ are monitored by measuring a detectable signal (e.g., fluorescent or chromogenic, respectively) that results from the activation of these reporter genes. LacZ transcription, for example, can be monitored by incubation in the presence of a substrate, such as X-gal (5-bromo-4-chloro-3-indolyl-β-D-galactoside), of its encoded enzyme, β-galactosidase. The pool of all interacting proteins isolated by this manner from mating the *D. melangaster* insulin-like sequence product and the library identifies the "insulin-like interactive population".

In a preferred embodiment of the present invention, false positives arising from transcriptional activation by the DNA binding domain fusion proteins in the absence of a transcriptional activator domain fusion protein are prevented or reduced by negative selection prior to exposure to the activation domain fusion population (see e.g. PCT International Publication No. WO97/47763, published Dec. 18, 1997, which is incorporated by reference herein in its entirety). By way of example, if such cell contains URA3 as a reporter gene, negative selection is carried out by incubating the cell in the presence of 5-fluoroorotic acid (5-FOA, which kills URA+ cells (Rothstein, 1983, Meth. Enzymol. 101:167–180). Hence, the metabolism of 5-FOA will lead to cell death of self-activating DNA-binding domain hybrids.

In a preferred aspect, negative selection involving a selectable marker as a reporter gene can be combined with the use of a toxic or growth inhibitory agent to allow a higher rate of processing than other methods. Negative selection can also be carried out on the activation domain fusion population prior to interaction with the DNA binding domain fusion population, by similar methods, either alone or in addition to negative selection of the DNA binding fusion population. Negative selection can be carried out on the recovered protein-protein complex by known methods (see e.g., Bartel et al., 1993, BioTechniques 14:920–924; PCT International Publication No. WO97/47763, published Dec. 18, 1997).

In a preferred embodiment of the invention the DNA sequences encoding the pairs of interactive proteins are isolated by a method wherein either the DNA-binding domain hybrids or the activation domain hybrids are amplified, in separate respective reactions. Preferably, the amplification is carried out by polymerase chain reaction (PCR) (see U.S. Pat. Nos. 4,683,202; 4,683,195; and 4,889,818; Gyllenstein et al., 1988, Proc. Natl. Acad. Sci. U.S.A. 85:7652–7656; Ochman et al., 1988, Genetics 120:621–623; Loh et al., 1989, Science 243:217–220; Innis et al., 1990, *PCR Protocols*, Academic Press, Inc., San Diego, Calif.) using pairs of oligonucleotide primers specific for either the DNA-binding domain hybrids or the activation domain hybrids. Other amplification methods known in the art can be used, including but not limited to ligase chain reaction (see EP 320,308), use of Qβ replicase, or methods listed in Kricka et al., 1995, *Molecular Probing, Blotting, and Sequencing*, Academic Press, New York, Chapter 1 and Table IX.

The plasmids encoding the DNA-binding domain hybrid and the activation domain hybrid proteins can also be isolated and cloned by any of the methods well known in the art. For example, but not by way of limitation, if a shuttle (yeast to *E. coli*) vector is used to express the fusion proteins, the genes can be recovered by transforming the yeast DNA into *E. coli* and recovering the plasmids from *E. coli* (see e.g., Hoffinan et al., 1987, Gene 57:267–272). Alternatively, the yeast vector can be isolated, and the insert encoding the fusion protein subcloned into a bacterial expression vector, for growth of the plasmid in *E. coli*.

5.10. BIOCHEMICAL ASSAYS USING INSULIN-LIKE PROTEINS

The present invention provides for biochemical assays using the insulin-like proteins. In one embodiment, Drosophila insulin-like proteins are useful for biochemical assays aimed at the identification and characterization of the ligand(s) for the known Drosophila insulin receptor encoded by the InR (DIR) gene (Nishida, et al., 1986, Biochem. Biophys. Res. Commun. 141(2):474–81; Petruzzelli, et al., 1986, Proc. Natl. Acad. Sci. U.S.A. 83(13):4710–4; Fernandez-Almonacid and Rosen, 1987, Mol. Cell Biol. 7(8):2718–27), or the identification of ligands for new insulin-like receptor proteins that are discovered. The cDNAs encoding the insulin-like proteins can be individually subclone into any of a large variety of eukaryotic expression vectors permitting expression in insect and mammalian cells, described above. The resulting genetically engineered cell lines expressing insulin-like proteins can be assayed for production, processing, and secretion of the mature insulin-like proteins, which lack the secretory signal peptide and connecting C peptide regions, for example with antibodies to Drosophila insulin-like proteins and Western blotting assays or ELISA assays. For assays of specific receptor binding and functional activation of receptor proteins, one can employ either crude culture medium or extracts containing secreted protein from genetically engineered cells (devoid of other insulin proteins), or partially purified culture medium or extracts, or preferably highly purified Drosophila insulin-like protein fractionated, for example, by chromatographic methods. Alternatively, mature Drosophila insulin-like protein can be synthesized using chemical methods (Nagata, et al., 1992, peptides 13(4):653–62).

Specific protein binding of Drosophila insulin-like proteins to the Drosophila InR receptor can be assayed as follows, for example, following the procedures of Yamaguchi et al. (Yamaguchi et al., 1995, Biochemistry 34:4962–4968). Chinese hamster ovary cells, COS cells, or any other suitable cell line, can be transiently transfected or stably transformed with expression constructs that direct the production of the Drosophila insulin receptor InR. Direct binding of a Drosophila insulin-like protein to such InR-expressing cells can be measured using a "labeled" purified Drosophila insulin-like protein derivative, where the label is typically a chemical or protein moiety covalently attached to the insulin-like polypeptide which permits the experimental monitoring and quantitation of the labeled Drosophila insulin-like protein in a complex mixture.

Specifically, the label attached to the insulin-like protein can be a radioactive substituent such as an $^{125}$I-moiety or $^{32}$P-phosphate moiety, a fluorescent chemical moiety, or labels which allow for indirect methods of detection such as a biotin-moiety for binding by avidin or streptavidin, an epitope-tag such as a Myc- or FLAG-tag, or a protein fusion domain which allows for direct or indirect enzymatic detection such as an alkaline phosphatase-fusion or Fc-fusion domain. Such labeled Drosophila insulin-like proteins can be used to test for direct and specific binding to InR-expressing cells by incubating the labeled Drosophila insulin-like protein with the InR-expressing cells in serum-free medium, washing the cells with ice-cold phosphate buffered saline to remove unbound insulin-like protein, lysing the cells in buffer with an appropriate detergent, and measuring label in the lysates to determine the amount of bound insulin-like protein. Alternatively, in place of whole cells, membrane fractions obtained from InR-expressing cells may also be used. Also, instead of a direct binding assay, a competition binding assay may be used. For example, crude extracts or purified Drosophila insulin-like protein can be used as a competitor for binding of labeled purified bovine or porcine insulin to InR-expressing cells, by adding increasing concentrations of Drosophila insulin-like protein to the mixture. The specificity and affinity of binding of Drosophila insulin-like proteins can be judged by comparison with other insulin superfamily proteins tested in the same assay, for example vertebrate insulin, vertebrate IGF-I, vertebrate IGF-IH, vertebrate relaxin, or silkmoth bombyxin.

5.10.1. IDENTIFICATION OF ADDITIONAL RECEPTORS OR INSULIN-LIKE BINDING PROTEINS

The invention described herein provides for methods in which Drosophila insulin-like proteins are used for the identification of novel insulin receptor proteins, other than Drosophila InR, using biochemical methods well known to those skilled in the art for detecting specific protein-protein interactions (Current Protocols in Protein Science, 1998, Coligan et al., eds., John Wiley & Sons, Inc., Somerset, N.J.). Given the sequence diversity of the Drosophila insulin-like proteins detailed herein, the identification to date of only a single insulin receptor gene in Drosophila, InR, points to the possibility that some Drosophila insulin-like proteins may bind to other receptors. In particular, it is possible that some Drosophila insulin-like proteins interact with receptor types that have not yet been discovered in vertebrates, for example the relaxin receptor, or receptor types that are specific to invertebrates. The identification of either novel receptor types or invertebrate-specific receptor types is of great interest with respect to human therapeutic applications, or pesticide applications, respectively. Assuming some Drosophila insulin-like proteins do not exhibit specific protein binding to the known InR protein in the binding assays described above, then the novel cognate receptors for these insulin-like proteins can be investigated and identified as follows. Labeled Drosophila insulin-like proteins can be used for binding assays in situ to identify tissues and cells possessing cognate receptors, for example as described elsewhere (Gorczyca et al., 1993, J. Neurosci. 13:3692–3704). Also, labeled Drosophila insulin-like proteins can be used to identify specific binding proteins including receptor proteins by affinity chromatography of Drosophila protein extracts using resins, beads, or chips with bound Drosophila insulin-like protein (Formosa, et al., 1991, Methods Enzymol 208:24–45; Formosa, et al., 1983, Proc. Natl. Acad. Sci. USA 80(9):2442–6). Further, specific insulin-binding proteins can be identified by cross-linking of radioactively-labeled or epitope-tagged insulin-like protein to specific binding proteins in lysates, followed by electrophoresis to identify and isolate the cross-linked protein species (Ransone, 1995, Methods Enzymol 254:491–7). Still further, molecular cloning methods can be used to identify novel receptors and binding proteins for Drosophila insulin-like proteins including expression cloning of specific receptors using Drosophila cDNA expression libraries transfected into mammalian cells (Section 5.8), expression cloning of specific binding proteins using Drosophila cDNA libraries expressed in *E. coli* (Cheng and Flanagan, 1994, Cell 79(1):157–68), and yeast two-hybrid methods (as described above) using a Drosophila insulin-like protein fusion as a "bait" for screening activation-domain fusion libraries derived from Drosophila cDNA (Young and Davis, 1983, Science 15 222(4625):778–82; Young and Davis, 1983, Proc. Natl. Acad. Sci. USA 80(5):1194–8; Sikela and Hahn, 1987, Proc. Natl. Acad. Sci. USA 84(9):3038–42; Takemoto, et al., 1997, DNA Cell Biol 16(6):797–9).

5.10.2. ASSAYS OF INSULIN-LIKE PROTEINS

The functional activity of insulin-like proteins, derivatives and analogs can be assayed by various methods known to one skilled in the art.

For example, in one embodiment, where one is assaying for the ability to bind to or compete with a wild-type insulin-like protein for binding to an anti-insulin-like protein antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (e.g., using colloidal gold, enzyme or radioisotope labels), western blots, precipitation reactions, agglutination assays (e.g. gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. In another embodiment, where an insulin-like-binding protein is identified, the binding can be assayed, e.g. by means well-known in the art. In another embodiment, physiological correlates of insulin-like protein binding to its substrates and/or receptors (e.g., signal transduction) can be assayed.

In another embodiment, in insect (e.g., Sf9 cells), fly (e.g., *D. melanogaster*), or other model systems, genetic studies can be done to study the phenotypic effect of an insulin-like gene mutant that is a derivative or analog of a wild-type insulin-like gene. Other such methods will be readily apparent to the skilled artisan and are within the scope of the invention.

5.10.3. OTHER FUNCTIONAL ASSAYS

For functional assays of Drosophila insulin-like protein, beyond receptor binding, the following activities can be investigated using InR-expressing cells after exposing said cells to crude or purified fractions of Drosophila insulin-like protein and comparing these results with those obtained with other insulin superfamily proteins described above (Yamaguchi et al., 1995, Biochemistry 34:4962–4968). Assayable functional activities include stimulation of cell proliferation; stimulation of overall tyrosine kinase activity by immunoblotting of cell extracts with an anti-phosphotyrosine antibody; stimulation of phosphorylation of specific substrate proteins such as InR or IRS-1 using $^{32}$p-labeling and immunoprecipitation with antibodies that specifically recognize the substrate protein; and stimulation of other enzymatic activities linked to the insulin signaling pathway including assays of MAP kinase, Mek kinase, Akt kinase, and PI3-kinase activities.

5.11. IDENTIFYING SIGNALING PATHWAYS AND PHENOTYPES

This invention provides animal models which may be used in the identification and characterization of *D. melan-*

*gaster* insulin-like protein signaling pathways, and/or phenotypes associated with the mutation or abnormal expression of a *D. melanogaster* insulin-like protein. Methods of producing such animal models using novel genes and proteins are well known in the art (see e.g., PCT International Publication No. WO 96/34099, published Oct. 31, 1996, which is incorporated by reference herein in its entirety). Such models include but are not limited to the following embodiments. Additional specific examples of animal models and their use are described in Section 6 below.

First, animals are provided in which a normal *D. melangaster* insulin-like gene has been recombinantly introduced into the genome of the animal as an additional gene, under the regulation of either an exogenous or an endogenous promoter element, and as either a minigene or a large genomic fragment. Animals are also provided in which a normal gene has been recombinantly substituted for one or both copies of the animal's homologous gene by homologous recombination or gene targeting.

Second, animals are provided in which a mutant *D. melangaster* insulin-like gene has been recombinantly introduced into the genome of the animal as an additional gene, under the regulation of either an exogenous or an endogenous promoter element, and as either a minigene or a large genomic fragment. Animals are also provided in which a mutant gene has been recombinantly substituted for one or both copies of the animal's homologous gene by homologous recombination or gene targeting.

Third, animals are provided in which a mutant version of one of that animal's own genes (bearing, for example, a specific mutation corresponding to, or similar to, a pathogenic mutation of an insulin-like gene from another species) has been recombinantly introduced into the genome of the animal as an additional gene, under the regulation of either an exogenous or an endogenous promoter element, and as either a minigene or a large genomic fragment.

Finally, equivalents of transgenic animals, including animals with mutated or inactivated genes, may be produced using chemical or x-ray mutagenesis. Using the isolated nucleic acids disclosed or otherwise enabled herein, one of ordinary skill may more rapidly screen the resulting offspring by, for example, direct sequencing, restriction fragment length polymorphism (RFLP) analysis, PCR, or hybridization analysis to detect mutants, or Southern blotting to demonstrate loss of one allele.

Such animal models may be used to identify a *D. melangaster* insulin-like protein signaling pathway by various methods. In one embodiment, this invention provides a method of identifying a *D. melangaster* insulin-like protein signaling pathway comprising: (a) disrupting a *D. melangaster* insulin-like gene; and (b) identifying the effect of the gene disrupted in step (a) in an assay selected from the group consisting of a developmental assay, an energy metabolism assay, a growth rate assay and a reproductive capacity assay, lethality, sterility, reduced brood size, increased brood size, altered life span, defective locomotion, altered body shape, altered body plan, altered body size, altered bristles, altered body weight, altered cell size, increased cell division, decreased cell division, altered feeding, slowed development, increased development, decreased metabolism (including but not limited to alterations in glycogen synthesis, storage, and/or degradation, alterations in lipid synthesis, storage and/or degradation, alterations in levels of carbohydrate in hemolymph, alterations in levels of lipid in hemolymph), alterations in morphogenesis (including but not limited to organs or tissues of the gonad, nervous system, fat body, hemacytes, peripheral sensory organs, imaginal discs, eye, wing, leg, antennae, bristle, gut or musculature). Such assays are well known to those skilled in the art. In one embodiment, results of the assay may be compared to known mutant phenotypes to determine the signaling pathway involved. In one embodiment, the gene is disrupted using chemical mutagenesis. Ia another embodiment, the gene is disrupted using transposon mutagenesis. In a further embodiment, the gene is disrupted by radiation mutagenesis. Examples of such mutagenesis are set forth in Section 6 below.

Further, this invention provides a method of identifying a phenotype associated with mutation or abnormal expression of a *D. melangaster* insulin-like protein comprising identifying the effect of a mutated or abnormally expressed *D. melanogaster* insulin-like gene in a *D. melangaster* animal. In one embodiment, the effect is determined by an assay selected from the group consisting of a developmental assay, an energy metabolism assay, a growth rate assay and a reproductive capacity assay, lethality, sterility, reduced brood size, increased brood size, altered life span, defective locomotion, altered body shape, altered body plan, altered body size, altered body weight, altered cell size, increased cell division, decreased cell division, altered feeding, slowed development, increased development, decreased metabolism (including but not limited to alterations in glycogen synthesis, storage, and/or degradation, alterations in lipid synthesis, storage and/or degradation, alterations in levels of carbohydrate in hemolymph, alterations in levels of lipid in hemolymph), alterations in morphogenesis (including but not limited to organs or tissues of the gonad, nervous system, fat body, hemacytes, peripheral sensory organs, imaginal discs, eye, wing, leg, antennae, bristle, gut or musculature). Still further, this invention provides a method of identifying a phenotype associated with mutation or abnormal expression of a *D. melangaster* insulin-like protein comprising: (a) mutating or abnormally expressing a *D. melangaster* insulin-like gene in a *D. melangaster* animal; and (b) identifying the effect of the gene mutated or abnormally expressed. In one embodiment, the effect is determined by an assay selected from the group consisting of a developmental assay, an energy metabolism assay, a growth rate assay and a reproductive capacity assay, lethality, sterility, reduced brood size, increased brood size, altered life span, defective locomotion, altered body shape, altered body plan, altered body size, altered body weight, altered cell size, increased cell division, decreased cell division, altered feeding, slowed development, increased development, decreased metabolism (including but not limited to alterations in glycogen synthesis, storage, and/or degradation, alterations in lipid synthesis, storage, and/or degradation, alterations in levels of carbohydrate in hemolymph, alterations in levels of lipid in hemolymph), alterations in morphogenesis (including but not limited to organs or tissues of the gonad, nervous system, fat body, hemacytes, peripheral sensory organs, imaginal discs, eye, wing, leg, antennae, bristle, gut or musculature). In another embodiment, the gene is mutated or abnormally expressed using a technique selected from the group consisting of chemical mutagenesis, radiation mutagenesis, transposon mutagenesis, antisense and double-stranded RNA interference. Abnormal (i.e. ectopic) expression can be overexpression, underexpression (e.g., due to inactivation), expression at a developmental time different from wild-type animals, or expression in a cell type different from in wild-type animals.

5.11.1. ANALYSIS OF GENETIC INTERACTIONS AND MULTIPLE MUTANTS

Yet another approach that may be used to probe the biological function of the insulin-like genes identified herein is by using tests for genetic interactions with other genes that may participate in the same, related, interacting, or modifying genetic or biochemical pathways. In particular, since it is evident that there are multiple insulin-like genes in the Drosophila genome, this raises the possibility of functional redundancy of one or more genes. Consequently, it is of interest to investigate the phenotypes of fruit flies containing mutations that eliminate the function of more than one insulin-like gene. Such strains carrying mutations in multiple genes can be generated by cross breeding animals carrying the individual mutations, followed by selection of recombinant progeny that carry the desired multiple mutations.

One specific question-of-interest is genetic analysis of interactions of insulin-like genes with other well-characterized Drosophila genes and pathways. Thus, double mutant fruit flies may be constructed that carry mutations in an insulin-like gene and another gene-of-interest.

It is of particular interest to test the interaction of the insulin-like genes with other genes implicated in insulin signaling, especially those that exhibit homology to insulin signaling components in vertebrates. For example, fruit flies carrying mutations in insulin-like genes and either a loss-of-function mutation of InR, chico, Pi3K92, Akt1, 14-3-3z, csw, Lar, Pk61C, Glut3, Ide, shaggy, s6k, Ras85D, drk, Sos, rl, or Dsor1 (FlyBase 1998, "FlyBase—A Drosophila Database", Nucleic Acids Research 26:85–88; http://flybase.bio.indiana.edu), would be of use in investigating the involvement of different insulin-like genes in the signaling pathway where these genes participate. Similarly, transgenic animals mis-expressing insulin-like genes which further carry mutations in InR, chico, Pi3K92, Akt1, 14-3-3z, csw, Lar, Pk61C, Glut3, Ide, shaggy, s6k, Ras85D, drk, Sos, rl, or Dsor1 (FlyBase 1998, "FlyBase—A Drosophila Database", Nucleic Acids Research 26:85–88; http://flybase.bio.indiana.edu) are of also of interest. Other genetic interactions may be tested based on the actual phenotypes observed for alterations of the insulin-like genes alone.

5.11.2. GENETIC MODIFIER SCREENS

The initial characterization of phenotypes created by mutations in single or multiple insulin-like genes is expected to lead to the identification of Drosophila strains that exhibit mutant phenotypes suitable for large scale genetic modifier screens aimed at discovering other components of the same pathway. The procedures involved in typical genetic modifier screens to define other components of a genetic/biochemical pathway are well known to those skilled in the art and have been described elsewhere (Wolfaer and Goldberg, 1994, Methods in Cell Biology 44:33–80; Karim et al., 1996, Genetics 143:315–329). Such genetic modifier screens are based on the identification of mutations in other genes that modify an initial mutant phenotype, by isolating either suppressor mutations that return the mutant phenotype toward normal, or enhancer mutations that make the initial mutant phenotype more severe.

5.11.3. STANDARD GENETIC MODIFIER SCREENS

Genetic modifier screens differ depending upon the precise nature of the mutant allele being modified. If the mutant allele is genetically recessive, as is commonly the situation for a loss-of-function allele, then most typically males, or in some cases females, which carry one copy of the mutant allele are exposed to an effective mutagen, such as EMS, MMS, ENU, triethylamine, diepoxyalkanes, ICR-170, formaldehyde, X-rays, gamma rays, or ultraviolet radiation. The mutagenized animals are crossed to animals of the opposite sex that also carrying the mutant allele to be modified, and the resulting progeny are scored for rare events that result in a suppressed or enhanced version of the original mutant phenotype. In the case where the mutant allele being modified is genetically dominant, as is commonly the situation for ectopically expressed genes, wild type males are mutagenized and crossed to females carrying the mutant allele to be modified. Any new mutations identified as modifiers (i.e. suppressors or enhancers) are candidates for genes that participate in the same phenotype-generating pathway.

In a pilot-scale genetic modifier screen, 10,000 or fewer mutagenized progeny are inspected; in a moderate size screen, 10,000 to 50,000 mutagenized progeny are inspected; and in a large scale screen, over 50,000 mutagenized progeny are inspected. Progeny exhibiting either enhancement or suppression of the original phenotype are immediately crossed to adults containing balancer chromosomes and used as founders of a stable genetic line. In addition, progeny of the founder adult are retested under the original screening conditions to ensure stability and reproducibility of the phenotype. Additional secondary screens may be employed, as appropriate, to confirm the suitability of each new modifier mutant line for further analysis. For example, newly identified modifier mutations can be tested directly for interaction with other genes of interest known to be involved or implicated in insulin signaling pathways (InR, chico, Pi3K92, Atk1, 14-3-3z, csw, Lar, Pk61C, Glut3, Ide, shaggy, s6k, Ras85D, drk, Sos, rl, Dsor1, mutations in other insulin-like genes, or other modifier genes obtained from different genetic screens of the insulin signaling pathway), using methods described above. Also, the new modifier mutations can be tested for interactions with genes in other pathways thought to be unrelated or distantly related to insulin signaling, such as genes in the Notch signaling pathway. New modifier mutations that exhibit specific genetic interactions with other genes implicated in insulin signaling, but not interactions with genes in unrelated pathways, are of particular interest. Additionally, strains can be generated that carry the new modifier mutations of interest in the absence of the original insulin-like gene mutation (i.e. a strain wild type for the mutant allele being suppressed or enhanced) to determine whether the new modifier mutation exhibits an intrinsic phenotype, independent of the mutation in the insulin-like gene, which might provide further clues as to the normal function of the new modifier gene.

Each newly-identified modifier mutation can be crossed to other modifier mutations identified in the same screen to place them into complementation groups, which typically correspond to individual genes (Greenspan, 1997, In *Fly Pushing: The Theory and Practice of Drosophila Genetics*, Plainview, N.Y., Cold Spring Harbor Laboratory Press: pp. 23–46). Two modifier mutations are said to fall within the same complementation group if animals carrying both mutations in trans exhibit essentially the same phenotype as animals that are homozygous for each mutation individually.

5.11.4. GAIN-OF-FUNCTION MODIFIER SCREENS

Although the genetic modifier screens described above are quite powerful and sensitive, some genes that participate in an insulin-like pathway may be missed in this approach, particularly if there is functional redundancy of those genes. This is because the vast majority of the mutations generated in the standard mutagenesis methods described above will be loss-of-function mutations, whereas gain-of-function mutations that could reveal genes with functional redundancy will be relatively rare. Another method of genetic screening in Drosophila has been developed that focuses specifically on systematic gain-of-function genetic screens (Rorth, et al., 1998, Development 125:1049–1057). This method is based on a modular mis-expression system utilizing components of the GAL4/UAS system (which were defined above). In this case a modified P element, termed an EP element, is genetically engineered to contain a GAL4-responsive UAS element and promoter, and this engineered transposon is used to randomly tag genes by insertional mutagenesis (similar to the method of P mutagenesis described above). Thousands of transgenic Drosophila strains, termed EP lines, can thus be generated each containing a specific UAS-tagged gene. This approach takes advantage of a well-recognized insertional preference of P elements, where it has been found that P elements have a strong tendency to insert at the 5'-ends of genes. Consequently, many of the genes that have been tagged by insertion of EP elements become operably fused to a GAL4-regulated promoter, and increased expression or mis-expression of the randomly tagged gene can be induced by crossing in a GAL4 driver gene (similar that described above).

Thus, systematic gain-of-function genetic screens for modifiers of phenotypes induced by mutation or mis-expression of an insulin-like gene can be performed as follows. A large battery of thousands of Drosophila EP lines can be crossed into a genetic background containing a mutant or mis-expressed insulin-like gene, and further containing an appropriate GAL4 driver transgene. The progeny of this cross can be inspected for enhancement or suppression of the original phenotype induced by mutation/mis-expression of the insulin-like gene. Progeny that exhibit an enhanced or suppressed phenotype can be crossed further to verify the reproducibility and specificity of this genetic interaction with the insulin-like gene. EP insertions that demonstrate a specific genetic interaction with a mutant or mis-expressed insulin-like gene, have therefore physically tagged a new gene that genetically interacts with the insulin-like. The new modifier gene can be identified and sequenced using PCR or hybridization screening methods that allow the isolation of the genomic DNA adjacent to the position of the EP element insertion.

5.12. ASSAYS FOR CHANGES IN GENE EXPRESSION

This invention provides assays for detecting changes in the expression of the D. melangaster insulin-like genes and proteins. Assays for changes in gene expression are well known in the art (see e.g., PCT Publication No. WO 96/34099, published Oct. 31, 1996, which is incorporated by reference herein in its entirety). Such assays may be performed in vitro using transformed cell lines, immortalized cell lines, or recombinant cell lines, or in vivo using animal models.

In particular, the assays may detect the presence of increased or decreased expression of a D. melangaster insulin-like gene or protein on the basis of increased or decreased mRNA expression (using, e.g., nucleic acid probes), increased or decreased levels of related protein products (using, e.g., the antibodies disclosed herein), or increased or decreased levels of expression of a marker gene (e.g., β-galactosidase or luciferase) operably linked to a 5' regulatory region in a recombinant construct.

In yet another series of embodiments, various expression analysis techniques may be used to identify genes which are differentially expressed between two conditions, such as a cell line or animal expressing a normal D. melangaster insulin-like gene compared to another cell line or animal expressing a mutant D. melangaster insulin-like gene. Such techniques comprise any expression analysis technique known to one skilled in the art, including but not limited to differential display, serial analysis of gene expression (SAGE), nucleic acid array technology, subtractive hybridization, proteome analysis and mass-spectrometry of two-dimensional protein gels. In a specific embodiment, nucleic acid array technology (i.e., gene chips) may be used to determine a global (i.e., genome-wide) gene expression pattern in a normal D. melangaster animal for comparison with an animal having a mutation in one or more D. melangaster insulin-like genes.

To elaborate further, the various methods of gene expression profiling mentioned above can be used to identify other genes (or proteins) that may have a functional relation to (e.g., may participate in a signaling pathway with) a D. melanogaster insulin-like gene. Gene identification of such other genes is made by detecting changes in their expression levels following mutation, i.e., insertion, deletion or substitution in, or overexpression, underexpression, mis-expression or knock-out, of a D. melanogaster insulin-like gene, as described herein. Expression profiling methods thus provide a powerful approach for analyzing the effects of mutation in a D. melangaster insulin-like gene.

Methods of gene expression profiling are well-known in the art, as exemplified by the following references describing subtractive hybridization (Wang and Brown, 1991, Proc. Natl. Acad. Sci. U.S.A. 88:11505–11509), differential display (Liang and Pardee, 1992, Science 257:967–971), SAGE (Velculescu et al., 1995, Science 270:484–487), proteome analysis (Humphery-Smith et al., 1997, Electrophoresis 18:1217–1242; Dainese et al., 1997, Electrophoresis 18:432–442), and hybridization-based methods employing nucleic acid arrays (Heller et al., 1997, Proc. Natl. Acad. Sci. U.S.A. 94:215014 2155; Lashkari et al., 1997, Proc. Natl. Acad. Sci. U.S.A. 94:13057–13062; Wodicka et al., 1997, Nature Biotechnol. 15:1259–1267).

5.13. INSULIN-LIKE GENE REGULATORY ELEMENTS

This invention provides methods for using insulin-like gene regulatory DNA elements to identify tissues, cells, genes and factors that specifically control insulin-like protein production. In one embodiment, regulatory DNA elements, such as enhancers/promoters, from Drosophila insulin-like genes are useful for identifying and manipulating specific cells and tissues that synthesize an insulin-like protein. Such hormone secreting cells and tissues are of considerable interest since they are likely to have an important regulatory function within the animal in sensing and controlling growth, development, reproduction, and/or metabolism. Analyzing components that are specific to insulin-like protein secreting cells is likely to lead to an understanding of how to manipulate these regulatory processes, either for therapeutic applications or pesticide applications, as well as an understanding of how to diagnose dysfunction in these processes. For example, it is of specific interest to investigate whether there are neuroendocrine tissues in Drosophila that might have a function related to that of the mammalian pancreas in sensing and controlling metabolic activity through the production of an insulin-like protein. Regulatory DNA elements derived from insulin-like genes provide a means to mark and manipulate such cells, and further, identify regulatory genes and proteins, as described below.

5.13.1. GENE FUSIONS WITH INSULIN-LIKE GENE REGULATORY DNA ELEMENTS

In a specific embodiment, gene fusions with the insulin-like regulatory elements can be made. For compact genes that have relatively few and small intervening sequences, such as the insulin-like genes described here, it is typically the case that the regulatory elements that control spatial and temporal expression patterns are found in the DNA immediately upstream of the coding region, extending to the nearest neighboring gene. Thus, putative regulatory DNA regions can be defined for the dIns2, dIns3, and dIns4 genes based on the sequence information provided in FIG. 4. As shown in FIG. 4, the putative promoters ("PUT PROMOTER" or "PUT PROM") of the insulin-like genes are indicated with heavy lines below the respective sequences. Regulatory regions can be used to construct gene fusions where the regulatory DNAs are operably fused to a coding region for a reporter protein whose expression is easily detected, and these constructs are introduced as transgenes into Drosophila. An entire regulatory DNA region can be used, or the regulatory region can be divided into smaller segments to identify subelements that might be specific for controlling expression a given cell type or stage of development. Examples of reporter proteins that can be used for construction of these gene fusions include, but are not limited to, E. coli beta-galactosidase or the fluorescent GFP protein whose products can be detected readily in situ and which are useful for histological studies (O'Kane and Gehring, 1987, Proc. Natl. Acad. Sci. U.S.A. 84(24) :9123–7; Chalfie, et al., 1994, Science 263:802–805) and sorting of specific cells that express insulin-like proteins (Cumberledge and Krasnow, 1994, Methods in Cell Biology 44:143–159); the cre or FLP recombinase proteins that can be used to control the presence and expression of other genes in the same cells through site-specific recombination (Golic and Lindquist, 1989, Cell 59(3):499–509; White, et al., 1996, Science 271:805–7); toxic proteins such as the reaper and hid cell death proteins which are useful to specifically ablate cells that normally express insulin-like proteins in order to assess the physiological function of this tissue (Kingston, 1998, In *Current Protocols in Molecular Biology*. Ausubel et al., John Wiley & Sons, Inc. sections 12.0.3–12.10) or any other protein where it is desired to examine the function this particular protein specifically in cells that synthesize and secrete insulin-like proteins (as described in the mis-expression analysis above).

Alternatively, a binary reporter system can be used, similar to that described above, where the insulin-like regulatory element is operably fused to the coding region of an exogenous transcriptional activator protein, such as the GAL4 or tTA activators described above, to create an insulin-like regulatory element "driver gene". For the other half of the binary system the exogenous activator controls a separate "target gene" containing a coding region of a reporter protein operably fused to a cognate regulatory element for the exogenous activator protein, such as $UAS_G$ or a tTA-response element, respectively. An advantage of a binary system is that a single driver gene construct can be used to activate transcription from preconstructed target genes encoding different reporter proteins, each with its own uses as delineated above.

The insulin-like regulatory element-reporter gene fusions described in the preceding paragraph are also useful for tests of genetic interactions, where the objective is to identify those genes that have a specific role in controlling the expression of insulin-like genes, or promoting the growth and differentiation of the tissues that expresses the insulin-like protein. Transgenic Drosophila carrying an insulin-like regulatory element-reporter gene fusion can be crossed with another Drosophila strain carrying a mutation-of-interest and the resulting progeny examined. For example, the mutation-or-interest might be a modifier mutation arising from a genetic modifier screen as described in a preceding section. If no change of expression of the reporter gene in the resulting progeny is observed, this is indicative of a lack of involvement of the gene altered by the mutation-of-interest in controlling insulin-like protein expression; by contrast, if a significant increase, decrease, loss, or mis-expression of the reporter protein in the resulting progeny is observed, this is indicative of a regulatory role for the gene altered by the mutation-of-interest in cells expressing the insulin-like protein.

5.13.2. PROTEIN-DNA BINDING ASSAYS

In a third embodiment, insulin-like gene regulatory DNA elements are also useful in protein-DNA binding assays to identify gene regulatory proteins that control the expression of insulin-like genes. Such gene regulatory proteins can be detected using a variety of methods that probe specific protein-DNA interactions well known to those skilled in the art (Kingston, 1998, In *Current Protocols in Molecular Biology*, Ausubel et al, John Wiley & Sons, Inc., sections 12.0.3–12.10) including in vivo footprinting assays based on protection of DNA sequences from chemical and enzymatic modification within living or permeabilized cells, in vitro footprinting assays based on protection of DNA sequences from chemical or enzymatic modification using protein extracts nitrocellulose filter-binding assays and gel electrophoresis mobility shift assays using radioactively labeled regulatory DNA elements mixed with protein extracts. In particular, it is of interest to identify those DNA binding proteins whose presence or absence is specific to insulin-like protein expressing tissue, as judged by comparison of the DNA-binding assays described above using cells/extracts from an insulin-like gene expressing tissue versus other cells/extracts from tissues that do not express insulin-like genes. For example, a DNA-binding activity that is specifically present in cells that normally express an insulin-like protein might function as a transcriptional activator of the insulin-like gene; conversely, a DNA-binding activity that is specifically absent in cells that normally express an insulin-like protein might function as a transcriptional repressor of the insulin-like gene. Having identified candidate insulin-like gene regulatory proteins using the above DNA-binding assays, these regulatory proteins can themselves by purified using a combination of conventional and DNA-affinity purification techniques. In this case, the DNA-affinity resins/beads are generated by covalent attachment to the resin of a small synthetic double stranded oligonucleotide corresponding to the recognition site of the DNA binding activity, or a small DNA fragment corresponding to the recognition site of the DNA binding activity, or a DNA segment containing tandemly iterated versions of the recognition site of the DNA binding activity. Alternatively, molecular cloning strategies can be used to identify proteins that specifically bind insulin-like gene regulatory DNA elements. For example, a Drosophila cDNA library in an *E. coli* expression vector, such as the lambda-gt11 vector, can be screened for Drosophila cDNAs that encode insulin-like gene regulatory element DNA-binding activity by probing the library with a labeled DNA fragment, or synthetic oligonucleotide, derived from the insulin-like gene regulatory DNA, preferably using a DNA region where specific protein binding has already been demonstrated with a protein-DNA binding assay described above (Singh et al., 1989, Biotechniques 7:252–61). Similarly, the yeast "one-hybrid" system can be used as another molecular cloning strategy (Li and Herskowitz, 1993, Science 262:1870–4; Luo, et al., 1996, Biotechniques 20(4):564–8; Vidal, et al., 1996, Proc. Natl.

Acad. Sci. U.S.A. 93(19):10315–20). In this case, the insulin-like gene regulatory DNA element is operably fused as an upstream activating sequence (UAS) to one, or typically more, yeast reporter genes such as the lacZ gene, the URA3 gene, the LEU2 gene, the HIS3 gene, or the LYS2 gene, and the reporter gene fusion construct(s) inserted into an appropriate yeast host strain. It is expected that in the engineered yeast host strain the reporter genes will not be transcriptionally active, for lack of a transcriptional activator protein to bind the UAS derived from the Drosophila insulin-like gene regulatory DNA. The engineered yeast host strain can be transformed with a library of Drosophila cDNAs inserted in a yeast activation domain fusion protein expression vector, e.g. pGAD, where the coding regions of the Drosophila cDNA inserts are fused to a functional yeast activation domain coding segment, such as those derived from the GAL4 or VP16 activators. Transformed yeast cells that acquire Drosophila cDNAs that encode proteins that bind the Drosophila insulin-like gene regulatory element can be identified based on the concerted activation the reporter genes, either by genetic selection for prototrophy (e.g. LEU2, HIS3, or LYS2 reporters) or by screening with chromogenic substrates (lacZ reporter) by methods known in the art.

5.14. USE OF DROSOPHILA INSULIN-LIKE PROTEINS AS A MEDIA SUPPLEMENT FOR GROWTH AND MAINTENANCE OF INSECT CELLS IN CULTURE

Examples of culture media that are commonly used to maintain Drosophila and other insect cell lines include Schneider's medium (Schneider, 1964, J. Exp. Zool. 156:91–103), D-22 (Echalier and Ohanessian, 1970, In Vitro 6:162–172), M3 (Shields and Sang, 1977, Drosophila Information Service 52:161), and commercially available media such as HyQ-CCM3 (HyClone Laboratories, Inc., Logan, Utah), Sf-900 II (Life Technologies, Inc., Rockville, Md.), Grace's insect medium Life Technologies, Inc., Rockville, Md., IPL-41 insect medium Life Technologies, Inc., Rockville, Md., TC-100 insect medium (Life Technologies, Inc., Rockville, Md.), Ex-Cell 401 (JRH Biosciences, Lenexa, Kans.), and TMN-FH (PharMingen, San Diego, Calif.). However, not all insect cells can be propagated effectively in available media and furthermore it is difficult and time consuming to wean cells onto serum-free media for large scale protein production.

As mentioned in Section 2.4.2, one of the earliest indications of the possible existence of insulin-like hormones in Drosophila came from experiments aimed at the in vitro culture of Drosophila cells, where mammalian insulin was found to exhibit profound and useful effects. Seecof and Dewhurst first noted that addition of bovine insulin to the medium facilitated the initiation of continuous cell lines from primary cultures from Drosophila (Seecof and Dewhurst, 1974, Cell Differ. 3(1):63–70). Subsequently, Mosna and Barigozzi similarly showed that supplementing the medium with purified bovine insulin greatly increased the ability to obtain continuous cell lines from primary cultures of Drosophila embryos (Mosna and Barigozzi, 1976, Experientia 32(7):855–6). Strikingly, Mosna later showed that crystalline bovine insulin could completely replace fetal calf serum as a necessary growth/survival factor(s) for propagation of Drosophila cell lines in vitro (Mosna, 1981, Experientia 37(5):466–7).

More recently, Wyss demonstrated that addition of bovine insulin to the medium at concentrations of 1 $\mu$g/ml to 10 $\mu$g/ml permitted 70% survival of embryonic cells in culture, compared to less than 1% survival in the absence of insulin (Wyss, 1982, Exp Cell Res 139(2):297–307). In the same study it was found that aside from promoting cell growth and/or survival, bovine insulin could stimulate differentiation of embryonic cells into various cell types, mostly nerve, muscle, and fat body cells. These results are in keeping with the well-characterized and useful effects of mammalian insulin and IGFs as growth and differentiation factors for the propagation of mammalian cells in culture.

The present invention provides for the use of Drosophila homologs of insulin-like proteins, as media additive for growth and maintenance of cells in culture. Moreover, given that the Drosophila insulin-like proteins are the authentic endogenous protein hormones for Drosophila cells, and are likely to be more structurally and functionally similar to the authentic endogenous insulin-like hormones for other insect species, it is expected that Drosophila insulin-like hormones will exhibit superior properties in promoting growth and differentiation of insect cells in culture compared to the effects found for mammalian insulins on insect cells.

In a specific embodiment, the Drosophila insulin-like proteins are used for the in vitro cultivation of Drosophila or other insect cells. Insect cell lines are widely used for basic research on the cell and molecular biology of insects. Also, Drosophila and other insect cell lines have application as a preferred system for developing cell-based assays for insecticide targets, particularly those that might be amenable to high throughput screening methods (U.S. Pat. No. 5,767,261; U.S. Pat. No. 5,487,986; U.S. Pat. No. 5,641,652; U.S. Pat. No. 5,593,862; U.S. Pat. No. 5,593,864; U.S. Pat. No. 5,550,049; U.S. Pat. No. 5,514,578).

In another embodiment, the Drosophila insulin-like proteins are employed for the in vitro cultivation of Drosophila and other insect cell lines used as host cells for the economical production of recombinant proteins on laboratory, pilot, or commercial scales (Johansen, et al., 1989, Genes Dev. 3(6):882–9; Culp, et al., 1991, Biotechnology 9(2):173–7; Kirkpatrick, et al., 1995, J. Biol. Chem. 270(34):19800–5; Griffiths and Page, 1997, Methods Mol. Biol. 75:427–40; McCarroll and King, 1997, Curr. Opin. Biotechnol 8(5):590–4; Merrington, et al., 1997, Mol. Biotechnol. 8(3):283–97; Possee, 1997, C Opin. Biotechnol. 8(5):569–72). Further, the Drosophila and other insect cell lines can be used as hosts for the large-scale growth in vitro of viruses or bacteria that can be used as commercial insect control agents (Zhou, et al., 1998, Proc. R. Soc. Lond. B. Biol. Sci. 265:509–15; Miltenburger, 1980, Dev. Biol. Stand. 46:295–300; Miltenburger and Reimann, 1980, Dev. Biol. Stand. 46:217–22; Shuler, et al., 1990, Ann. N.Y. Acad. Sci. 589:399–422).

Although fetal calf serum has been traditionally used as a media additive for the growth of insect cells in culture, it has a number of serious disadvantages. First, fetal calf serum is expensive, and is often used in large amounts at concentrations typically between 5% to 15%. Occasionally, fetal calf serum is not available commercially. Also, there are batch-to-batch variations in the activity of fetal calf serum in stimulating cell growth, and some batches have been found to be toxic to insect cells in culture. Thus, there is a need for substitutes for fetal calf serum in growth media for insect cells in culture, and the use of Drosophila insulin-like proteins for this purpose is expected to help fulfill this need.

Accordingly, Drosophila insulin-like proteins described herein can be used as an additive to insect cell growth media at concentrations preferably ranging from 5 ng/L to 0.5 g/L, and as a substitute for either fetal calf serum or mammalian insulin, for the following purposes (a) promoting the propagation of continuous insect cell lines from primary cultures; (b) promoting the differentiation and maintenance of specific insect cell types in culture such as nerve cells, muscle cells, or fat body cells; (c) promoting the propagation of insect cell lines in vitro for use in cell-based pesticide screening assays; (d) promoting the propagation of insect cell lines in vitro for use in large-scale production of recombinant proteins, natural protein products, or other natural products; and (e) promoting the propagation of insect cells for the large-scale production of viruses and bacteria which use insect cells as a host.

5.15. AGRICULTURAL USES OF DROSOPHILA INSULIN-LIKE GENES

In another embodiment of the invention, Drosophila insulin-like genes may be used in controlling agriculturally important pest species. For example, the proteins disclosed herein, or analogs or derivatives thereof, may have activity in modifying the growth, feeding and/or reproduction of crop-damaging insects, or insect pests of farm animals or of other animals. In general, effective pesticides exert a disabling activity on the target pest such as lethality, sterility, paralysis, blocked development, or cessation of feeding. Such pests include but are not limited to egg, larval, juvenile and adult forms of flies, mosquitos, fleas, moths, beetles, cicadia, grasshoppers, and crickets.

Tests for such activities can be any method known in the art. Pesticides comprising the nucleic acids of the Drosophila insulin like proteins may be prepared in a suitable vector for delivery to a plant or animal. Such vectors include but are not limited to *Agrobacterium tumefaciens* Ti plasmid-based vectors for the generation of transgenic plants (Horsch et al., 1984, Science 233:496–89; Fraley et al., 1983, Proc. Natl. Acad. Sci. USA 80: 4803) or recombinant cauliflower mosaic virus for theincoulation of plant cells or plants (Hohn et al., 1982, In Molecular Biology of Plant Tumors, Academic Press, New York, pp 549–560; Howell U.S. Pat. No. 4,407,956); retrovirus based vectors for the introduction of genes into vertebrate animals (Burns et al., 1993, Proc. Natl. Acad. Sci. USA 90:8033–37); and vectors based on transposable elements such a P (Rubin and Spradling, 1982, Science 218:348–53), minos (Loukeris et al., 1995, Proc. Natl. Acad. Sci. USA 92:9485–89), Hermes (O'Brochta et al., 1996, Genetics 142: 907–14), mariner (Coates et al., 1998, Proc. Natl. Acad. Sci. USA 95:3748–51), or PiggyBac (Handler et al., 1998, Proc. Natl. Acad. Sci. USA 95:7520–25) for the introduction of genes into insects. For example, transgenic insects can be generated using a transgene comprising an insulin-like gene operably fused to an appropriate inducible promoter. For example, a tTA-responsive promoter may be used (see Section 5.7.7) in order to direct expression of the insulin-like protein at an appropriate time in the life cycle of the insect. In this way, one may test efficacy as an insecticide in, for example, the larval phase of the life cycle (i.e. when feeding does the greatest damage to crops).

Further, recombinant or synthetic insulin-like proteins, analogs, or derivatives can be assayed for insecticidal activity by injection of solutions of insulin-like proteins into the hemolymph of insect larvae (Blackburn, et al., 1998, Appl. Environ. Microbiol. 64(8):3036–41; Bowen and Ensign, 1998, Appl. Environ. Microbiol. 64(8):3029–35). Still further, transgenic plants that express insulin-like proteins can be tested for activity against insect pests (Estruch, et al., 1997, Nat. Biotechnol. 15(2):137–41).

In a preferred embodiment, insulin-like genes can be tested as insect control agents in the form of recombinant viruses that direct the expression of an insulin-like gene in the target pest. Suitable recombinant virus systems for expression of proteins in infected insect cells include but are not limited to recombinant Semliki Forest virus (DiCiommo and Bremner, 1998, J. Biol. Chem. 273:18060–66), recombinant sindbis virus (Higgs et al., 1995, Insect Mol. Biol. 4:97–103; Seabaugh et al., 1998, Virology 243:99–112), recombinant pantropic retrovirus (Matsubara et al., 1996, Proc. Natl. Acad. Sci. USA 93:6181–85; Jordan et al., 1998, Insect Mol. Biol. 7:215–22), and most preferably recombinant baculovirus. Use of recombinant baculoviruses as a means to engineer expression of toxic proteins in insects, and as insect control agents, is well known in the art. This approach has a number of specific advantages including host specificity, environmental safety, the availability of easily manipulable vector systems, and the potential use of the recombinant virus directly as a pesticide without the need for purification or formulation of the insulin-like protein (Cory and Bishop, 1997, Mol. Biotechnol. 7(3):303–13; U.S. Pat. No. 5,470,735; U.S. Pat. No. 5,352,451; U.S. Pat. No. 5, 770, 192; U.S. Pat. No. 5,759,809; U.S. Pat. No. 5,665,349; U.S. Pat. No. 5,554,592). Thus, recombinant baculoviruses that direct the expression of insulin-like genes can be used for both testing the pesticidal activity of insulin-like proteins under controlled laboratory conditions, and as insect control agents in the field. One disadvantage of wild type baculoviruses as insect control agents can be the amount of time between application of the virus and death of the target insect, typically one to two weeks. During this period, the insect larvae continue to feed and damage crops. Consequently, there is a need to develop improved baculovirus-derived insect control agents which result in a rapid cessation of feeding of infected target insects. The well-known metabolic regulatory role of insulins in vertebrates raises the possibility that expression of insulin-like proteins from recombinant baculovirus in infected insects may have a desirable effect in controlling metabolism and limiting feeding of insect pests.

Mutational anaylsis of insulin-like genes may also be used in connection with the control of agriculturally-important pests. In this regard, mutational analysis of genes encoding insulin-like hormones in Drosophila provides a rational approach to determine the precise biological function of this class of hormones in invertebrates. Further, mutational analysis provides a means to validate potential pesticide targets that are constituents of these signaling pathways.

Drosophila insulin-like genes, proteins or derivatives thereof may be formulated with any carrier suitable for agricultural use, such as water, organic solvents and/or inorganic solvents. The pesticide composition may be in the form of a solid or liquid composition and may be prepared by fundamental formulation processes including but not limited to dissolving, mixing, milling, granulating, and dispersing.

The present invention encompasses compositions containing a Drosophila insulin-like protein or gene in a mixture with agriculturally acceptable excipients known in the art, including but not limited to vehicles, carriers, binders, UV blockers, adhesives, hemecants, thickeners, dispersing agents, preservatives and insect attractants. Thus the compositions of the invention may, for example, be formulated as a solid comprising the active agent and a finely divided solid carrier. Alternatively, the active agent may be contained in liquid compositions including dispersions, emulsions and suspensions thereof. Any suitable final formulation may be used, including for example, granules, powder, bait pellets (a solid composition containing the active agent and an insect attractant or food substance), microcapsules, water dispersible granules, emulsions and emulsified concentrates.

Examples of adjuvant or carriers suitable for use with the present invention include but are not limited to water, organic solvent, inorganic solvent, talc, pyrophyllite, synthetic fine silica, attapugus clay, kieselguhr chalk, diatomaceous earth, lime, calcium carbonate, bontonite, fuller's earth, cottonseed hulls, wheat flour, soybean flour, pumice, tripoli, wood flour, walnut shell flour, redwood flour, and lignin.

The compositions of the present invention may also include conventional insecticidal agents and/or may be applied in conjunction with conventional insecticidal agents.

6. EXAMPLES

The following examples are provided merely as illustrative of various aspects of the invention and shall not be construed to limit the invention in any way.

6.1. IDENTIFICATION OF D. MELANOGASTER INSULIN-LIKE GENES

A family of insulin-like genes has been identified in the model organism *D. melanogaster* (i.e., the fly *Drosophila melanogaster*). This invention provides the following examples of identification of three Drosophila insulin-like genes as illustrated in the alignment of FIG. 8 and described in detail below.

6.2. IDENTIFICATION OF DROSOPHILA INSULIN-LIKE GENES IN GENOMIC SEQUENCE

A Drosophila cDNA encoding an insulin-like protein, termed dIns1, was identified by random sequencing of cDNAs in a library enriched for sequences expressed in U.S. patent application Ser. No. 09/201,226, now U.S. Pat. No. 6,135,942 Issued Oct. 24, 2000 (Attorney Docket No. 7326-077) entitled "NUCLEIC ACID AND PROTEIN OF *D. MELANOGASTER* INSULIN-LIKE GENE AND USES THEREOF" by Maria Leptin). We reasoned that other members of the insulin-like gene family in Drosophila could be identified by isolation and characterization of the genomic region surrounding the dINS1 gene.

Sequence database searches using the BLAST algorithm (Altschul, et al., 1990, J. Mol. Biol. 215(3):403–10; Altschul, et al., 1997, Nucleic Acids Res. 25(17):3389–402) revealed that the dIns1 cDNA was identical over a 217 bp region to Dm3500, a sequence tagged site (STS) mapped by the Berkeley Drosophila Genome Project to chromosome 3, band 67C-D. Several P1 clones of genomic DNA had been molecularly mapped into a contig containing this STS, DS00060. Bacterial colonies containing P1 clones that molecularly map in and around DS00060 were obtained from Genome Systems, Inc. (St. Louis, Mo.). DNA from each of bacterial culture was screened for the presence of the dIns1 gene using a PCR-based assay. A small sample from each colony was picked with the end of a toothpick and transferred directly into 15 µl of PCR reaction buffer (supplied by the manufacturer, Perkin Elmer) containing 0.75 units Perkin Elmer Taq DNA polymerase, 2.5 mM MgCl$_2$, and 2.5 µM each of the following DNA primers:

LepEco5: CTA GGA ATT CGA TCG AGC AGG ATG AG (SEQ ID NO:8)

LepXba3: CAC TTC TAG ATC ATC AGG CGC AGT AG (SEQ ID NO:9)

Thermocycling conditions used were as follows (where 0:00 indicates time in minutes:seconds): an initial denaturation of 94° C., 4:00 followed by 35 cycles of 95° C., 0:30; 55° C., 1:00; and 72° C., 0:45. Products of the PCR reactions were analyzed by agarose gel electrophoresis. One of the PI clones from this library, DS05250 (well L11, plate 14), was confirmed to produce a PCR product of the expected size for dINS1 and was selected for DNA sequencing.

The bacterial culture containing the DS05250 P1 clone was spread on an LB agar plate containing 25 µg/ml kanamycin, incubated overnight at 37° C., and a single colony was picked and used to inoculate 250 ml of Luria broth containing 25 µg/ml kanamycin. The culture was incubated with shaking at 37° C. for 16 hours, bacterial cells were collected by centrifugation, and DNA was purified with a Qiagen Maxi-Prep System kit (QIAGEN, Inc., Valencia, Calif.). The entire DNA sequence of the DS05250 P1 insert was obtained using a strategy that combined shotgun and directed sequencing of a small insert plasmid DNA library derived from the DS05250 P1 DNA (Ruddy DA, et al. Genome Research, 1997, 7:441–456). All DNA sequencing reactions were performed using standard protocols for the BigDye sequencing reagents (Applied Biosystems, Inc. Foster City, Calif.) and products were analyzed using ABI 377 DNA sequencers. Trace data obtained from the ABI 377 DNA sequencers was analyzed and assembled into contigs comprising the complete P1 insert sequence using the phred-phrap computational package (Phil Green, U. of Washington).

6.3. COMPUTATIONAL STRATEGY

The complete DNA sequence of the DS05250 P1 clone was analyzed by computational methods to identify insulin-like genes and other genes that might reside on this clone. The TBLASTN computer program (Altschul, et al., 1990, J. Mol. Biol. 215(3):403–10; Altschul, et al., 1997, Nucleic Acids Res. 25(17):3389–402) was employed with the dIns1 predicted protein sequence as a query to identify other insulin-like genes in this region. The results revealed that DS05250 contained part of the dIns1 coding region, as well as three other putative insulin-like genes in adjacent sequences (named dIns2, dIns3, and dIns4; see FIG. 3). The GeneFinder (Phil Green, University of Washington) and GenScan programs (Burge and Karlin, 1997, J. Mol. Biol. 268(1):78–94) were used to predict coding regions, splice junctions, promoters, and poly(A) addition sites for each of the new insulin-like genes.

The presence of other gene sequences was investigated using the GeneFinder program, and also by analysis with the BLAST family of programs using the DS05250 sequence as a query against public and proprietary DNA and protein sequence databases. This analysis indicated that the DS05250 DNA contained additional genes distal to the dIns4 coding region with respect to the other insulin-like genes (FIG. 3); one region exhibited perfect homology to an uncharacterized Drosophila EST, and a second region exhibited a high degree of coding sequence homology with vertebrate anion channel proteins. Thus, we operationally defined the domain of the insulin-like multigene cluster in the DS05250 sequence as an 10,149 bp region that extends from the dIns1 end of the DNA insert to the start of the region homologous with the uncharacterized EST.

Since it was determined that the DS05250 P1 clone insert ended within the dIns1 gene and did not contain the complete cluster of insulin-like genes, a pooling strategy was employed using the remaining PI clones mapped to this region in an effort to extend the sequence of the dIns1 end of this cluster. Accordingly, the following P1 clones were picked, pooled, and DNA prepared from bacterial cultures for DNA sequencing as described above for the DS05250 P1 clone: DS04166, DS07104, DS01000, DS06457, DS00683, DS00010, and DS00833. The same DNA sequencing strategy of combined shotgun and directed sequencing was employed on the pooled P1 clone DNA as that described above for the isolated DS0520 DNA. Individual sequence reads from the P1 pool were assembled with the DS05250 sequence contig using the phred-phrap computational package. The P1 pool strategy as successful in extending the sequence of the insulin-like gene cluster by 4.77 kbp beyond the end of the DS05250 sequence. Computational analysis of this additional sequence using the TBLASTN, GeneFinder, and GenScan programs, as above, revealed that the additional sequence from the P1 pool contained the N-terminal coding region of the dIns1 gene, an intergenic region, and an adjacent gene exhibiting homology to an uncharacteried Drosophila EST (see FIG. 3). Thus, we could define the limits of the cluster of repeated insulin-like genes in this genomic location as an 10,781 bp segment extending from the end of the sequences containing a predicted open reading frame with homology to the uncharacterized EST on the dIns1 end of the cluster to the uncharacterized EST on the dIns3 end of the cluster (FIG. 4). An annotated sequence of the insulin multigene cluster in the DS05250 is presented in FIG. 4.

6.4. ISOLATION AND SEQUENCE CHARACTERIZATION OF cDNAs CORRESPONDING TO THE DROSOPHILA INSULIN-LIKE GENES

The structure and expression of each new insulin-like gene predicted in the DS05250 genomic clone (dIns2, dIns3, and dIns4) was confirmed by either PCR amplification of inserts in Drosophila cDNA libraries, or reverse transcription of Drosophila mRNA and PCR amplification of the resulting cDNA (RT-PCR), as described below. For each gene, PCR primers were designed such that one primer annealed upstream of the predicted ATG codon, and the second primer annealed downstream of the predicted stop codon.

6.4.1. dIns2

The template source was a Canton S adult, oligo-dT- and random-primed cDNA library in the UniZap vector, purchased from Stratagene (Stratagene USA, La Jolla, Calif.). Library DNA was diluted to a concentration of approximately 2 ng/µl before use. dIns2 cDNA was amplified by PCR, using a ClonTech Advantage cDNA PCR kit (CLONETECH Laboratories, Inc., Palo Alto, Calif.) and the following primers:

fins2U70: CTTCATCACTCATGGGCATCGAG (SEQ ID NO:10)

fins2L515: TGGGTTAATAGGTTTACGAGGTT (SEQ ID NO:11)

The PCR reaction contained 1 µl 10×KlenTaq buffer, 1 µl dNTPs, and 1 µl KlenTaq enzyme mix, all as supplied by the manufacturer; to which was added 1 µl (2 ng) template DNA, and primers to a final concentration of 0.2 µM. Reaction conditions were as follows (where 0:00 indicates time in minutes:seconds): 95° C., 4:00, followed by 30 cycles of 95° C., 0:30; 55° C., 1:00; 68° C., 0:45.

Reaction products were analyzed by agarose gel electrophoresis, and a single major species was observed whose size matched that expected for the dIns2 cDNA (468 bp). The PCR product was isolated by electrophoresis in a 2% low melting point agarose gel stained with ethidium bromide, and the region of the gel containing the DNA was excised with a razor blade. Agarose was removed by digestion of the gel slice with β-agarase as follows: incubation at 65° C. for 10 min, addition of approximately 1/10 vol. 10×β-agarase buffer, brief incubation at 40° C., addition of 5 units β-agarase, and incubation for 1 h at 40° C. The sample was quickly frozen in a dry ice/ethanol bath, and the remaining agarose removed by centrifugation in a microcentrifuge for 15 min. The supernatant was decanted and DNA precipitated by addition of sodium acetate to 0.3 M final concentration, a small amount of glycogen as carrier, and 2 volumes isopropanol. The mixture was left at −20° C. for 30 min, and DNA collected by centrifugation in a microcentrifuge for 15 minutes. The resulting DNA pellet was dried and suspended in 10 µl TE buffer (10 mM Tris-HCl, pH 8.0, 1 mM EDTA).

The purified dIns2 cDNA PCR product was cloned by ligation into the vector pCRII using the InVitrogen TA Cloning Kit (Invitrogen Corp., Carlsbad, Calif.; Brun, et al., 1991, DNA Seq. 1(5):285–9) with subsequent transformation of E. coli, following the manufacturers directions. Individual transformant colonies were screened for the presence of the desired insert using a PCR assay with the dIns2-specific PCR primers (i.e. SEQ ID NO:10 and SEQ ID NO:1 1) described above. Plasmid DNA was isolated from the resulting colonies using an alkaline lysis method, and the insert DNA was sequenced using the BigDye sequencing kit (Applied Biosystems, Inc. Foster City, Calif.) with universal M13 forward and reverse sequencing primers. The resulting sequence obtained for dIns2 cDNA (FIG. 5) was in agreement with that predicted from the DS05250 genomic sequence. Shown in FIG. 5 is the annotated sequence of dIns2, which contains a signal sequence followed by a B peptide, C peptide, and A peptide, as indicated by the heavy lines below the respective sequences.

6.4.2. dIns3

The template source was freshly synthesized first strand cDNA generated using oligo-dT purified mRNA from 5 day old third instar larvae. cDNA synthesis was primed with oligo-dT primer containing a NotI site obtained from LifeTechnologies. The single stranded cDNA was amplified by PCR, using the ClonTech Advantage cDNA PCR kit and the following primers designed from the predicted dIns3 genomic sequence:

fins3OU16: GCTTCCGATTTAGTGGTATAAA (SEQ ID NO:12)

fins3OL584: TTCGTATGTATGTATGTATGTG (SEQ ID NO:13)

The PCR reaction contained 1 µl 10×KlenTaq buffer, 1 µl dNTPs, and 1 µl KlenTaq enzyme mix, all as supplied by the manufacturer; to which was added 0.5 µl template DNA and primers at a final concentration of 0.2 µM. Reaction conditions were as follows (where 0:00 indicates time in minutes:seconds): 95° C., 4:00, followed by 30 cycles of 95° C., 0:30; 55° C., 1:00; 68° C., 0:45.

The reaction products were analyzed by gel electrophoresis and a single major species of the size expected for dIns3 was observed. The dIns3 cDNA product was cloned into the vector pCRII as described above for dIns2.

The dIns3 cDNA inserts in pCRII clones were sequenced by PCR amplification of the insert DNA with either M13 forward and reverse primers, or fins3OU16 and fins3OL584 primers, followed by cycle-sequencing of the amplification products. The sequence determined for the dIns3 cDNA clones (FIG. 6) was in agreement with that predicted from the genomic sequence derived from the DS05250 P1 clone. Shown in FIG. 6 is the annotated sequence of dIns3, which contains a signal sequence followed by a B peptide, C peptide, and A peptide, as indicated by the heavy lines below the respective sequences.

6.4.3. dIns4

Reverse transcription and PCR amplification were used to obtain dIns4 cDNA clones as described above for dIns3 except that the following primers were used:

fins4U5: TAAACCCATAACCATGAGCAAGC (SEQ ID NO:14)

fins4L516: TCAGTTGGGGTCAATGATTTTCG (SEQ ID NO:15)

A single major product of the expected size was observed following agarose gel electrophoresis and the resulting dIns4 cDNA was purified, cloned and sequenced as described above for dIns2. The sequence determined for the dIns4 cDNA clone (FIG. 7) was in agreement with that predicted from the genomic sequence derived from the DS05250 P1 clone. Shown in FIG. 7 is the annotated sequence of dIns4, which contains a signal sequence followed by a B peptide, C peptide, and A peptide, as indicated by the heavy lines below the respective sequences.

6.5. STRUCTURAL FEATURES OF DROSOPHILA INSULIN-LIKE GENES AND PROTEINS

The genomic organization of Drosophila insulin-like genes revealed in the DS05250 sequence can be viewed as two pairs of genes, dIns1/dIns2 and dIns3/dIns4, where the genes in each pair are arranged in tandem and oriented in the same direction, but where each pair of genes is oriented in the opposite direction and transcribed convergently (see FIG. 3). This implies that during the evolution of this multigene cluster an inversion occurred to create this arrangement, as opposed to the simplest model for the generation of a multigene array resulting solely from unequal cross-over, which would produce tandem genes all oriented in the same direction (Kondo, et al., 1996, J. Mol. Biol. 259:926–937; Smit, et al., 1998, Prog. Neurobiol. 54:35–54).

The sequence of the genomic region of DS05250 also reveals that three of the four Drosophila insulin-like genes, dIns1, dIns2, and dIns4, have intervening sequences that disrupt coding regions. It is notable that the position of the intervening sequence is at essentially the same location in each of these genes: within the C peptide coding sequences very near the junction with the B peptide coding sequences (FIG. 4). This same approximate position of an intervening sequence is also frequently found in vertebrate insulin-like genes, supporting an evolutionary relationship between Drosophila and vertebrate members of the insulin superfamily (Murray-Rust, et al., 1992, BioEssays 14:325–331; McRory and Sherwood, 1997, DNA and Cell Biology 16:939–949). The dIns3 gene does not appear to have an intervening sequence that disrupts the coding region of this gene. There is precedent for this situation in the form of the bombyxin genes of Lepidoptera, which all lack intervening sequences (Kondo, et al., 1996, J. Mol. Biol. 259:926–937).

Alignment of the predicted sequences of the Drosophila insulin-like proteins with other vertebrate and invertebrate members of the insulin superfamily demonstrates that the Drosophila proteins all contain the key structural features known to be important for promoting proper folding and processing of these preprohormones (FIG. 8). It is particularly notable that each of the Drosophila insulin-like proteins (dIns1, dIns2, dIns3 and dIns4) possesses a large C peptide of more than 30 amino acids flanked by dibasic residues, which are recognized by prohormone convertases during removal of the C peptide from the prohormone. Also, none of the Drosophila insulin-like proteins have a large C-terminal extension, such as found in the E peptide region of IGFs. Consequently, the overall organization of the Drosophila insulin-like proteins is similar to that of vertebrate insulins rather than that of vertebrate IGFs, although the possibility remains that one or more Drosophila insulin-like proteins might have a growth-promoting function similar to that of vertebrate IGFs. This is of interest since it remains uncertain when the structure and function of IGFs diverged from insulins during metazoan evolution (McRory and Sherwood, 1997, DNA and Cell Biology 16:939–949). Also, the Drosophila insulin-like receptor InR exhibits a ligand-specificity with a preference for insulins as opposed to IGFs, even though InR appears to mediate growth-promoting activities in vivo.

All of the Drosophila insulin-like proteins possess exactly the same number (six) and spacing of Cys residues as found in vertebrate insulin superfamily proteins (boxed in FIG. 8), indicating that the disulfide bonding pattern stabilizing the folded structure of these proteins would also be identical. This contrasts with the situation for some other invertebrate insulin-like proteins which have been found to have unusual disulfide features including an extra pair of Cys residues (represented in FIG. 8 by MIP-I from freshwater snail, and F13B12 from the nematode C. elegans) or which may lack the conserved Cys residues (Brousseau, et al., 1998, Early 1998 East Coast Worm Meeting, abstract 20; Duret, et al., 1998, Genome Res. 8(4):348–53; Wisotzkey and Liu, 1998, Early 1998 East Coast Worm Meeting, abstract 206; Pierce and Ruvkun, 1998, Early 1998 East Coast Worm Meeting, abstract 150), or have altered spacing between Cys residues in the A or B chains (found in some C. elegans insulin-like proteins, (Kondo, et al., 1996, J. Mol. Biol. 259:926–937; Smit, et al., 1998, Prog. Neurobiol. 54:35–54). It is also evident that all of the Drosophila insulin-like proteins have hydrophobic residues in positions that normally contribute to stabilizing the core structure at the interface between the A and B peptides in the folded protein (shaded in FIG. 8). Given the presence of these conserved structural features in each of the Drosophila insulin-like proteins it is expected that they will adopt a secondary and tertiary structure very similar to that found in their vertebrate and invertebrate counterparts, specifically a long central helix in the B peptide and two short antiparallel helices in the A peptide joined by a loop.

Despite the presence of such conserved structural features, phylogenetic analyses indicate that the Drosophila insulin-like proteins are rather diverse at the primary sequence level, particularly at positions expected to be exposed on the surface of the mature hormones. This is all the more surprising given that these Drosophila genes are located immediately next to one another in the genome, and might therefore be expected to have evolved relatively recently from each other. By contrast, the very large family of known bombyxin proteins in Lepidoptera exhibits considerably less sequence divergence than the family of four Drosophila insulin-like proteins discussed here. Similarly, the family of five insulin-like proteins found in the freshwater snail, the MIPS, are also less diverse at the protein sequence level than the four Drosophila insulin-like proteins. Indeed, the Drosophila insulin-like proteins are more divergent from each other than the degree of sequence divergence observed between vertebrate insulins and IGFs. Accordingly, this sequence divergence amoung the Drosophila insulin-like proteins suggests the possibility that they may serve distinctly different functions and/or act by binding through different receptor proteins.

6.6. CROSS-HYBRIDIZATION EXPERIMENT FOR dIns1, dIns2, dIns3 and dIns4

Sequence alignments of the four Drosophila insulin-like proteins revealed diversity among these family members at the amino acid level (see FIG. 8). Computational comparisons of the nucleic acid sequences using BLASTN and dot plot programs provided further evidence of sequence divergence in both coding and non-coding regions. As an experimental demonstration of the sequence divergence of the dIns1 genes, a Southern blotting experiment was performed where the dIns1 cDNA was used as probe to test cross-hybridization with the other Drosophila insulin-like genes, and a C. elegans insulin-like gene (F13B12), under conditions of low, medium, and high stringency, as described below.

Plasmid DNAs (0.5 μg) containing inserts of each insulin-like cDNA were digested with an appropriate restriction enzyme to liberate the cDNA insert from the vector as follows: pcDNA3.1-dInS1, PmeI; pBS+-dIns2, EcoRI, pBS+-dIns3, EcoRI, pBS+-dIns4, EcoRI; and pcDNA3.1-F13B12, PmeI. The restriction enzyme digestions were divided into thirds (for testing low, medium and high stringency hybridization), arranged in three identical sets, and the products were separated by electrophoresis in a 1% agarose gel along with DNA size markers. DNA fragments were visualized by staining with ethidium bromide, UV transillumination, and photography. The results demonstrated complete digestion of each plasmid DNA, and importantly showed that approximately the same amount of each insulin-like cDNA fragment was present in the gel. DNAs in the gel were denatured by treatment with a 0.4 N NaOH solution, blotted to a Hybond N+ membrane (Amersham) by transfer in the same solution, and the membrane neutralized by washing in a buffer containing 0.5 M Tris-HCl, pH 7.2, 1 M NaCl. The membrane was cut into thirds, each containing an identical set of the different insulin-like cDNAS, and the membranes were pretreated in a hybridization buffer (0.5 M sodium phosphate. pH 7.2, 7% SDS, 1 mM EDTA, and 1% bovine serum albumin) which also contained 100 μg/ml sheared, denatured salmon sperm DNA. A DNA probe was prepared by digestion of a plasmid vector containing dIns1 cDNA with EcoRI to release the insert, separation of the dIns1 cDNA from the vector by agarose gel electrophoresis, and radiolabelling using α-$^{32}$P-dCTP with an Amersham Rediprime DNA labelling kit following the manufacturers directions (final incorporation of radioactivity into the probe was 30 μCi). Hybridization of the probe to membranes was carried out by incubating each membrane in the hybridization buffer above along with 10 μCi of $^{32}$P-labeled dIns1 cDNA probe overnight at 45° C. After hybridization, each membrane was washed two times each for 30 minutes each at 45 ° C. in wash buffer #1 (40 mM sodium phosphate, pH 7,2, 5% SDS, 1 mM EDTA, 0.5% bovine serum albumin), followed by four washes each for 30 minutes in wash buffer #2 (40 mM sodium phosphate, pH 7.2, 1% SDS, 1 mM EDTA), and subsequently each membrane was treated differently as described below for low, medium, or high stringency hybridization conditions. For low stringency hybridization, one membrane was not washed further. For medium stringency hybridization, a second membrane was subjected to four washes each for 30 minutes in wash buffer #2 at 55 ° C. For high stringency hybridization, a third membrane was subjected to four washes each for 30minutes in wash buffer #2 at 55 ° C., followed by four washes each for 30 minutes in wash buffer #2 at 65° C. The membranes were dried and radioactivity detected by autoradiography using X-ray film and an intensifying screen. Hybridization of the $^{32}$P-labeled dIns1 cDNA probe to the homologous dIns1 cDNA on the membranes was readily detected after only 15 minutes of autoradiography under all three hybridization conditions, and increasing the time of autoradiography to 2.5 hours revealed no detectable cross-hybridization of dIns1 probe to the dIns2, dIns3, dIns4, or F13B12 cDNAs on the membranes under any hybridization condition. After 2.5 hours of autoradiography, very weak hybridization of the probe could be detected to pBS+ vector fragments and marker DNA fragments, which was most evident on the low and medium stringency membranes (presumably due to weak nonspecific hybridization). Thus, these results clearly demonstrate that there is no significant cross-hybridization of dIns1 cDNA to any of the other Drosophila insulin-like cDNAs, dIns2, dIns3, and dIns4, under conditions of either low, medium or high stringency. Furthermore, these results provide clear experimental evidence of the significant sequence divergence of these genes.

The present invention is not to be limited in scope by the specific embodiments described herein. Indeed, various modifications of the invention in addition to those described herein will become apparent to those skilled in the art from the foregoing description and accompanying drawings. Such modifications are intended to fall within the scope of the appended claims.

Various references are cited herein above, including patent applications, patents, and publications, the disclosures of which are hereby incorporated by reference in their entireties.

What is claimed is:

1. An isolated nucleic acid comprising a nucleotide sequence as depicted in FIG. 7 (SEQ ID NO:5).

2. An isolated nucleic acid comprising a nucleotide sequence encoding an amino acid sequence as depicted in FIG. 7 (SEQ ID NO:6), wherein said nucleic acid is less than 15 kilobases.

3. An isolated RNA molecule comprising a nucleotide sequence as depicted in FIG. 7 (SEQ ID NO:5), wherein the base U (uracil) is substituted for the base T (thymine) of said sequence.

4. An isolated RNA molecule comprising a nucleotide sequence encoding an amino acid sequence as depicted in FIG. 7 (SEQ ID NO:6).

5. An isolated nucleic acid comprising a nucleotide sequence that is the reverse complement of a nucleotide sequence encoding an amino acid sequence as depicted in FIG. 7 (SEQ ID NO:6).

6. A method of producing a protein comprising:
   (a) growing a cultured cell containing a nucleic acid comprising a recombinant nucleotide sequence as depicted in FIG. 7 (SEQ ID NO:5), such that the protein encoded by said nucleotide sequence is expressed by the cell; and
   (b) recovering the expressed protein.

7. A method of producing a protein comprising:
   (a) growing a cultured cell containing a nucleic acid comprising a recombinant nucleotide sequence of less than 15 kilobases encoding a protein comprising an amino acid sequence as depicted in FIG. 7 (SEQ ID NO:6), such that the encoded protein is expressed by the cell; and
   (b) recovering the expressed protein.

8. A cultured cell containing a recombinant nucleic acid vector comprising a nucleotide sequence as depicted in FIG. 7 (SEQ ID NO:5).

9. A vector comprising (a) a nucleotide sequence as depicted in FIG. 7 (SEQ ID NO:5) and (b) an origin of replication.

10. The vector of claim 9 in which the nucleotide sequence is operably linked to a heterologous promoter.

11. A purified genomic nucleic acid consisting of a nucleotide sequence as depicted in FIG. 4 (SEQ ID NO:7).

12. A purified genomic nucleic acid consisting of a nucleotide sequence of less than 15 kilobases and comprising nucleotide numbers 1583 to 11120 as depicted in FIG. 4 (SEQ ID NO:7).

* * * * *